(12) United States Patent
Lee et al.

(10) Patent No.: US 8,492,374 B2
(45) Date of Patent: Jul. 23, 2013

(54) AZAAZULENE COMPOUNDS

(75) Inventors: On Lee, Hsinchu (TW); Chih-Hung Chen, Xinying (TW); Chi-Y Hung, Hsinchu (TW); Yow-Lone Chang, Hsinchu (TW); Ting-Shou Chen, Yangmei (TW)

(73) Assignee: Industrial Technology Research Institute (TW)

( * ) Notice: Subject to any disclaimer, the term of this patent is extended or adjusted under 35 U.S.C. 154(b) by 14 days.

(21) Appl. No.: 12/768,869

(22) Filed: Apr. 28, 2010

(65) Prior Publication Data

US 2010/0280012 A1 Nov. 4, 2010

Related U.S. Application Data

(60) Provisional application No. 61/173,883, filed on Apr. 29, 2009.

(51) Int. Cl.
| | | |
|---|---|---|
| *C07D 401/04* | (2006.01) | |
| *C07D 401/14* | (2006.01) | |
| *C07D 473/34* | (2006.01) | |
| *C07D 487/04* | (2006.01) | |
| *C07D 407/14* | (2006.01) | |
| *A61K 31/435* | (2006.01) | |
| *A61K 31/437* | (2006.01) | |
| *A61K 31/40* | (2006.01) | |
| *A61K 31/403* | (2006.01) | |
| *A61K 31/407* | (2006.01) | |
| *A61K 31/52* | (2006.01) | |
| *A61P 35/00* | (2006.01) | |

(52) U.S. Cl.
USPC ............. 514/218; 514/253.01; 514/254.02; 514/263.2; 514/259.1; 514/300; 514/303; 514/393; 540/575; 544/264; 544/281; 544/360; 544/361; 544/370; 546/118; 546/121; 548/302.1; 548/305.1

(58) Field of Classification Search
USPC ............. 514/218, 253.01, 254.02, 263.2, 514/259.1, 300, 303, 393; 540/575; 544/264, 544/281, 360, 361, 370; 546/118, 121; 548/302.1, 305.1
See application file for complete search history.

(56) References Cited

U.S. PATENT DOCUMENTS

| | | | |
|---|---|---|---|
| 3,113,950 A | 12/1963 | Sunagawa et al. | |
| 3,230,234 A | 1/1966 | Sunagawa et al. | |
| 3,311,641 A | 3/1967 | Sunagawa et al. | |
| 4,337,265 A | 6/1982 | Treasurywala et al. | |
| 5,013,736 A | 5/1991 | Nagahara et al. | |
| RE34,918 E | 4/1995 | Nagahara et al. | |
| 6,306,874 B1 | 10/2001 | Fraley et al. | |
| 6,479,512 B1 | 11/2002 | Fraley et al. | |
| 2003/0207883 A1 | 11/2003 | Renhowe et al. | |
| 2008/0125590 A1* | 5/2008 | Lee et al. ................. 544/373 |
| 2008/0274107 A1 | 11/2008 | Fraley et al. | |
| 2010/0222547 A1 | 9/2010 | Rajagopalan et al. | |

FOREIGN PATENT DOCUMENTS

| | | |
|---|---|---|
| CA | 2006743 | 6/1990 |
| EP | 0376223 | 7/1990 |
| EP | 0376233 | 7/1990 |
| EP | 1 918 277 | 5/2008 |
| WO | WO0129025 | 4/2001 |
| WO | WO0157018 | 8/2001 |
| WO | WO0222598 | 3/2002 |
| WO | WO2004018419 | 3/2004 |
| WO | WO2005082340 | 9/2005 |
| WO | WO2006015191 | 2/2006 |
| WO | WO2006124413 | 11/2006 |
| WO | WO2008112509 | 9/2008 |
| WO | WO2008/150899 | 12/2008 |

OTHER PUBLICATIONS

Abe et al. (Bulletin of the Chemical Society of Japan (1990), 63(5), 1543-5).*
Yamauchi, Noriko, et al., "Facile Synthesis of (2-Benzimidazolyl)-1-Azaazulenes, (2-Benzothiazolyl)-1-Azaazulenes, and Related Compounds and Evaluation of Their Anticancer in Vitro Activity", Heterocycles, 2008, Vo. 76, No. 1, pp. 617-634, compound 5, compound 2b, compound 2c.
Search Report from corresponding application No. PCT/CN2010/072342.
Abe, Norkita, et al., "Reaction of 2-Chlorocyclohepta[b]pyrrole-3-carbaldehyde with o-Phenylenediamine", Bull. Chem. Soc. Jpn., 1990, vol. 63, pp. 1543-1545.
Fraley, Mark E., et al., "Optimization of the indolyl quinolinone class of KDR(CEGFR-2) kinase inhibitors: effects of 5-amido- and 5-sulphonamido-indolyl groups on pharmacokinetics and hERG binding", Bioorganic & Medicinal Chemistry Letters, 2001, vol. 14.
Sepp-Lorenzino, Laura, et al., "A Novel Orally Bioavailable Inhibitor of Kinase Insert Domain-Containing Receptor Induces Antiangiogenic Effects and Prevent Tumor Growth in Vivo", Cancer Research, 2004, vol. 64, pp. 751-756.
Somwar, Romel, et al., "A dominant-negative p38 MAPK mutant and novel selective inhibitors of p38 MAPK reduce insulin-stimulated glucose uptake in 3T3-L1 adipocytes without affecting GLUT4 translocation.", The Journal of Biological Chemistry, vol. 277, No. 52, Issue of Dec. 27, pp. 50386-50395.
Nagahara Michiko, et al., "Synthesis and antiallergic activity of novel azaazulene derivatives", Chemical & pharmaceutical bulletin, 1994, vol. 42(12), pp. 2491-2499.

*Primary Examiner* — Bruck Kifle
(74) *Attorney, Agent, or Firm* — Lowe Hauptman Ham & Berner, LLP

(57) ABSTRACT

An azaazulene compound is provided. The azaazulene compound has formula (I) shown below. Each variable in formula (I) is defined in the specification. The compound can be used to treat cancer. The invention also provides a method for treating cancer. The method includes administering to a subject in need thereof an effective amount of one or more azaazulene compounds of formula (I).

13 Claims, 1 Drawing Sheet

OTHER PUBLICATIONS

Renhowe, Paul A., et al., "Design, structure-activity relationships and in vivo characterization of 4-Amino-3-benzimidazol-2-ylhdroquinolin-2-ones: a novel class of receptor tyrosine kinase inhibitors.", J. Med. Chem., 2009, vol. 52, pp. 278-292.

Payack, Joseph F., et al., "A concise synthesis of a novel antiangiogenic tyrosine kinase inhibitor.", J. Org. Chem. 2005, 70, 175-178.

Foster, Kelly A., et al.,"Attenuation of edema and infarct volume following focal cerebral ischemia by early but not delayed administration of a novel samall molecule KDR kinase inhibitor." Neuroscience Research, 2008, doi:10.1016/j.neures.2008.09.007.

European Search Report dated Dec. 12, 2012 from corresponding application No. 10769337.6-2101/2491025 PCT/CN2010072342.

* cited by examiner

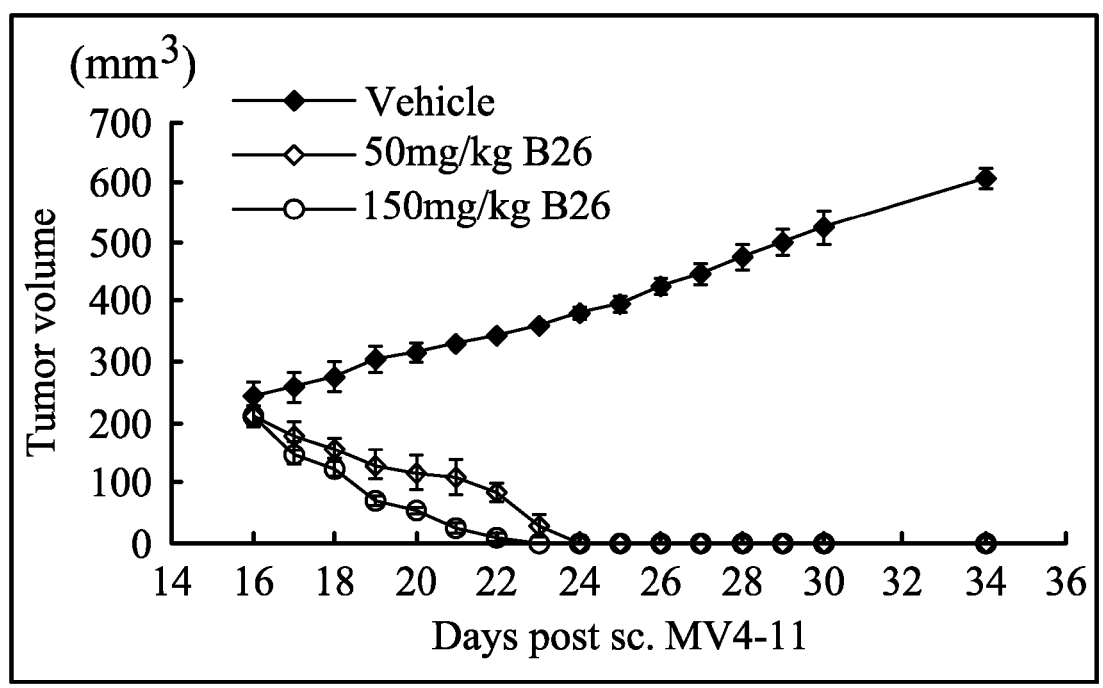

AZAAZULENE COMPOUNDS

CROSS-REFERENCE TO RELATED APPLICATIONS

This Application claims priority of U.S. provisional patent application Ser. No. 61/173,883, filed Apr. 29, 2009 and entitled "Novel Azaazulene Compounds With Multiple-Kinase Inhibitory Activities", the entirety of which is incorporated by reference herein.

BACKGROUND OF THE INVENTION

1. Field of the Invention

The invention relates to a medicine, and in particular to azaazulene compounds which modulate the protein kinases (PKs) activity and/or treat cancer.

2. Description of the Related Art

Protein kinases (PKs) are enzymes which catalyze the phosphorylation of specific tyrosine, serine, or threonine residues in cellular proteins. The PKs mediate cellular signal transduction in regulating cellular function such as proliferation, differentiation, growth, cell cycle, cell metabolism, cell survival, cell apoptosis, DNA damage repair, cell motility, and response to the microenvironment. Disregulated PKs activity is a frequent cause of disease such as angiogenesis, cancer, tumor growth, tumor metastasis, atherosclerosis, age related macular degeneration, diabetic retinopathy, inflammatory diseases and/or parasitical disease.

The PKs can be divided into two classes: the protein tyrosine kinases (PTKs) and the serine/threonine kinases (STKs). PTKs, which catalyze the transfer of the gamma-phosphate of ATP to tyrosine residues in protein substrates is one of the key covalent modifications that occurs in multicellular organisms as a result of intercellular communication during embryogenesis and maintenance of adult tissues. Phosphorylation of tyrosine residues modulates enzymatic activity of PTKs and the recruitment of downstream signaling proteins. Two classes of PTKs are present in cells: the transmembrane receptor PTKs and the nonreceptor PTKs. PTKs are critical components of cellular signaling pathways, their catalytic activity is strictly regulated. Unregulated activation of these enzymes, through mechanisms such as point mutations or over-expression, can lead to various forms of cancer as well as benign proliferative conditions. The importance of PTKs in health and disease is further underscored by the existence of aberrations in PTK signaling occurring in inflammatory diseases and diabetes. The growth factor receptors with PTK activity are known as receptor tyrosine kinases ("RTKs"). They comprise a large family of transmembrane receptors with diverse biological activity. The intracellular kinase domains of RTKs can be divided into two classes: those containing a stretch of amino acids separating the kinase domain and those in which the kinase domain is continuous. Activation of the kinase is achieved by ligand binding to the extracellular domain, which induces dimerization or oligomerization of the receptors. Receptors thus activated are able to autophosphorylate tyrosine residues outside the catalytic domain via cross-phosphorylation. The results of this auto-phosphorylation are stabilization of the active receptor conformation and the creation of phosphotyrosine docking sites for proteins which transduce signals within the cell. Signaling proteins which bind to the intracellular domain of receptor tyrosine kinases in a phosphotyrosine-dependent manner include RasGAP, PI3-kinase, phospholipase C phosphotyrosine phosphatase SHP and adaptor proteins such as Shc, Grb2 and Crk.

The EGFR, epidermal growth factor receptor, belongs to a family of receptor tyrosine kinases in mammals which is composed of four members: EGFR (ErB1), ErB2, ErB3, and ErB4. EGFR is an 1186 amino acid residue transmembrane glycoprotein. It consists of an extracellular ligand binding domain, an intracellular tyrosine kinase domain, and a COOH terminal region that contains autophosphorylation sites. The binding of specific ligands, such as EGF, transforming growth factor-beta, betacellulin, heparin-binding EGF, epiregulin, or amphiregulin, results in phosphorylation of multiple tyrosine residues in the COOH-terminal tail, triggering the cellular signaling pathway that regulates fundamental cellular processes such as proliferation, migration, differentiation and survival. EGFR is over expressed in many types of tumor cells, such as bladder, lung, gastric, breast, brain, head & neck, cervix, ovary, endometrium, etc. Abnormally high EGFR activity can be characteristic of non-small-cell lung cancers, breast cancers, ovarian cancers, bladder cancers, prostate cancers, salivary gland cancers, pancreatic cancers, endometrial cancers, colorectal cancers, kidney cancers, head and neck cancers, and glioblastoma multiforme. A tyrosine kinase inhibitor targeted to EGFR can be used for the treatment of cancers having abnormally high EGFR kinase activity and EFGR kinase disorder diseases.

One of RTK subfamily is referred to as the platelet derived growth factor receptor ("PDGFR") group, which includes PDGFR.alpha., PDGFR.beta., CSFIR, c-KIT and c-fms. These receptors consist of glycosylated extracellular domains composed of variable numbers of immunoglobin-like loops and an intracellular domain wherein the tyrosine kinase domain is interrupted by unrelated amino acid sequences. PDGFR signals induce expression of pro-angiogenic signals (including VEGF) in endothelial cells, further stimulating tumor angiogenesis. The PDGFR signaling pathway may play an important role in cell proliferation, cell migration, and angiogenesis, and may mediate the high interstitial fluid pressure of tumors.

Another group which, because of its similarity to the PDGFR subfamily, is sometimes subsumed into the later group is the fetus liver kinase ("flk") receptor subfamily. This group is believed to be made up of kinase insert domain-receptor fetal liver kinase-1 (KDR/FLK-1, VEGF-R2), flk-1R, flk-4 and fms-like tyrosine kinase 1 (flt-1). Abnormally high PDGFR activity can be characteristic of gastrointestinal stromal tumor, small cell lung cancer, glioblastoma multiforme, and prostate cancer. A tyrosine kinase inhibitor targeted to PDGFR can be used for the treatment of cancers having abnormally high PDGFR kinase activity and PDGFR kinase disorder diseases.

FLT-3 (FMS-like tyrosine kinase 3) is a class III RTK structurally related to PDGFR, and colony stimulating factor 1 (CSF1). These RTK contain five immunoglobulin-like domains in the extracellular region and an intracellular tyrosine kinase domain split in two by a specific hydrophilic insertion (kinase insert). FLT-3 expression was described on bone marrow CD34-positive cells, corresponding to multipotential, myeloid and B-lymphoid progenitor cells, and on monocytic cells. FLT3 expression is restricted to cells of the fetal liver expressing high levels of CD34. FLT3 receptor function can be defined by the activity of its ligand (FL). FL is an early acting factor and supports the survival, proliferation and differentiation of primitive hemopoietic progenitor cells. Ligand binding to FLT3 promotes receptor dimerization and subsequent signaling through phosphorylation of multiple cytoplasmatic proteins, including SHC, SHP-2, SHIP, Cbl, Cbl-b, Gab1 and Gab2, as well as the activation of several downstream signalling pathways, such as the Ras/

Raf/MAPK and PI3 kinase cascades. Internal tandem duplications (ITD) and/or insertions and, rarely, deletions in the FLT3-gene are implicated in 20-25% of all acute myeloid leukemias (AML). The duplicated sequence belongs to exon 11 but sometimes involves intron 11 and exon 12. The most frequently used nomenclature is FLT3-ITD. Because of the very heterogeneous molecular structure the term FLT3-LM (length mutation) seems to be more adequate. It was also described to be involved in 5-10% myelodysplastic syndromes (MDS) refractory anemia with excess of blasts (RAEB 1 and RAEB 2) and rare cases with acute lymphoblastic leukemia (ALL). A tyrosine kinase inhibitor targeted to FLT-3 can be used for the treatment of cancers having abnormally high FLT-3 kinase activity and FLT3 kinase disorder diseases.

C-KIT, SCFR (Stem Cell Factor Receptor), is known as type III receptor tyrosine kinase, structurally related to CSF-1R, PDGFR, and FLT-3, containing an extracellular domains with 5 Ig-like loops, a highly hydrophobic transmembrane domain, and an intracellular domain with tyrosine kinase activity split by a kinase insert (KI) in an ATP-binding region and in the phosphotransferase domain. C-Kit is expressed on the cell plasma membrane in the hematopoietic stem cells, mast cells, melanocytes, and germ-cell lineages. SCF/MGF receptor with PTK activity, binding of ligand (SCF) induces receptor dimerization, autophosphorylation and signal transduction via molecules containing SH2-domains. With the abnormal activity expression, mast cell hyperplasia in the bone marrow, liver, spleen, lymph nodes, gastrointestinal tract and skin, gain of function mutations are detected in most patients. It is recognized as clinical features of malignant hematopoietic cell growth are influenced by the time, the location of c-kit mutative events, and the number of associated lesions. A tyrosine kinase inhibitor targeted to c-Kit can be used for the treatment of cancers having abnormally high c-Kit kinase activity and c-Kit kinase disorder diseases.

Another member of the tyrosine kinase growth factor receptor family is the vascular endothelial growth factor receptor (VEGFR) subgroup. VEGFR is a dimeric glycoprotein similar to PDGFR but has different biological functions and target cell specificity in vivo. In particular, VEGFR is presently thought to play an essential role is vasculogenesis and angiogenesis. Angiogenesis is essential for tumor growth and survival. There are 3 distinct VEGF receptors-VEGFR-1, -2, and -3. Each of them contributes separately to the angiogenic process. VEGFR-1 is thought to play a role in regulating VEGF binding to VEGFR-2 during angiogenesis. VEGFR-2 (KDR) stimulates the proliferation, migration, and survival of endothelial cells during angiogenesis and is recognized as a critical VEGF receptor for angiogenesis. VEGFR-3 stimulates the proliferation, migration, and survival of endothelial cells during lymphangiogenesis, which in turn facilitates metastases. Despite these seemingly distinct roles, all VEGFRs overlap to some degree in their function, leading to significant redundancy. Therefore, inhibition of all identified VEGF receptors may ensure more complete inhibition of angiogenesis. A tyrosine kinase inhibitor targeted to VEGFR can be used for the treatment of solid tumors and vascular disorder diseases.

c-Met (hepatocyte growth factor receptor), is the high affinity receptor for HGF/SF, a multifunctional cytokine. Upon ligand binding, MET dimerizes and transphosphorylates tyrosine residues in the C-terminal domain, which then interacts with members of a variety of signaling pathways. These include Grb-2 associated binder 1, phosphoinositide 3' kinase and c-Src. Under physiological conditions, MET-HGF/SF signaling has been shown to affect a wide range of biological activities depending on the cell target. These activities vary from cell proliferation (mitogenesis) to cellular shaping (morphogenesis) and motility (motogenesis). The coordination of these diverse activities constitutes a genetic program of invasive growth that allows branched morphogenesis (the formation of epithelial tubular structures), myoblast migration and neurite branching. MET/HGF cell targets comprise epithelial and mesenchymal cells, hematopoietic cells, myoblasts, spinal motor neurons. MET-HGF/SF signaling is also essential for normal development: mouse embryos carrying null mutations in both HGF alleles die in midgestation and show impaired liver formation. MET and its ligand hepatocyte growth factor/scatter factor (HGF/SF) are expressed in numerous tissues although predominantly in cells of epithelial and mesenchymal origin, respectively. MET is amplified and overexpressed in many types of tumors, including tumors of the kidney, thyroid, pancreas and osteosarcoma. A tyrosine kinase inhibitor targeted to c-Met can be used for the treatment of cancers having abnormally high c-Met kinase activity and c-Met kinase disorder diseases.

RET is a tyrosine kinase receptor whose ligands are neurotrophic factors of the glial-cell line derived neurotrophic factor (GDNF) family, including GDNF, neurturin, artemin and persefin. RET activation is mediated via different glycosyl phosphatidylinositol-linked GRF receptors. 3 main isoforms of RET is detected in human, such as long isoform (RET51): 1114 amino acids, middle isoform (RET 43): 1106 amino acids and short isoform (RET 9): 1072 amino acids. RET is mainly expressed in tumors of neural crest origin: medullary thyroid carcinoma, pheochromocytoma and neuroblastoma. In human embryos, RET is expressed in a cranial population of neural crest cells, and in the developing nervous and urogenital systems. RET expression is found in several crest-derived cell lines, spleen, thymus, lymph nodes, salivary glands, spermatogonia, and recently in normal thyroid tissue, thyroid adenoma and both papillary and follicular thyroid cell neoplasias. A tyrosine kinase inhibitor targeted to RET can be used for the treatment of cancers having abnormally high RET kinase activity and RET kinase disorder diseases.

c-ABL (v-abl Abelson murine leukemia viral oncogene homolog) exhibit a permanent nuclear and cytoplasmic shuttling activity, driven by 3 nuclear localization signals (NLS) and a single nuclear export signal (NES) close to the C-terminal region. BCR/ABL has a cytoplasmic localization role and all three BCR-ABL fusion proteins have been shown to exhibit oncogenic potential. All three hybrid proteins have increased protein kinase activity compared to ABL: 3BP1 (binding protein) binds normal ABL on SH3 domain, which prevents SHI activation. Nuclear and cytoplasmic ABL may have different functions. 1-Nuclear c-ABL plays a major role in the regulation of cell death after DNA damage. All DNA damage inducing agents activate nuclear c-ABL kinase in an ATM-dependent manner and in the presence of the p53-homolog p73 protein. The latter is physically associated with c-ABL after DNA damage through the SH3 domain of c-ABL. DNA damage also activates simultaneously p53 pathway, leading to the activation of Rb which induces growth arrest and protects cells from apoptosis. The exact mechanisms of apoptosis induced by c-ABL are unknown. The nuclear entrapment of BCR-ABL has also been shown to induce apoptosis in leukemic cells. 2-Cytoplasmic c-ABL: possible function in adhesion signaling as an efflux of c-ABL from nucleus to the cytoplasm is found in fibroblasts after adhesion. A tyrosine kinase inhibitor targeted to c-ABL can be used for the treatment of cancers having abnormally high c-ABL kinase activity and c-ABL kinase disorder diseases.

TIE (tyrosine kinase with immunoglobulin-like and EGF-like domains) can be defined into two subgroups. TIE-1 (tyrosine kinase with Ig and EGF homology domains 1) and TIE-2/Tek comprise a receptor tyrosine kinase (RTK) subfamily with unique structural characteristics: two immunoglobulin-like domains flanking three epidermal growth factor (EGF)-like domains and followed by three fibronectin type III-like repeats in the extracellular region and a split tyrosine kinase domain in the cytoplasmic region. These receptors are expressed primarily on endothelial and hematopoietic progenitor cells and play critical roles in angiogenesis, vasculogenesis and hematopoiesis. Human TIE-1 cDNA encodes a 1124 amino acid (aa) residue precursor protein with an 18 residue putative signal peptide, a 727 residue extracellular domain and a 354 residue cytoplasmic domain. Two ligands, angiopoietin-1 (Ang1) and angiopoietin-2 (Ang2), which bind TIE-1 with high affinity, have been identified. Ang2 has been reported to act as an antagonist for Ang1. A tyrosine kinase inhibitor targeted to TIE can be used for the treatment of solid tumors and vascular disorder diseases.

FGFR (fibroblast growth factor receptors) consist of an extracellular ligand domain comprised of three immunoglobulin-like domains, a single transmembrane helix domain, and an intracellular domain with tyrosine kinase activity. The fibroblast growth factors are the largest family of growth factor ligands comprising of 23 members. FGFRs share a similar sequence structure, characterized by three extracellular immunoglobulin-like domains (IgI, IgII, and IgIII), a single-pass transmembrane segment, and a split tyrosine kinase (TK1/TK2) domain. The great majority of pathogenic FGFR mutations are missense, and all confer gain of function to the mutated protein. Some mutations are highly recurrent. The gain-of-function mechanisms identified for FGFR2 mutations are (a) selectively enhanced FGF-binding affinity, (b) illegitimate FGF-binding specificity, (c) FGF-independent covalent dimerization, and (d) ectopic spliceoform expression. These mechanisms account for the dominant inheritance of all the associated phenotypes. A tyrosine kinase inhibitor targeted to FGFR can be used for the treatment of cancers having abnormally high FGFR kinase activity and FGFR kinase disorder diseases.

Insulin-like growth factor 1 (IGF1) was considered a potential candidate for the treatment of heart failure. However, some animal studies and clinical trials have questioned whether elevating IGF1 chronically is beneficial. Secondary effects of increased serum IGF1 levels on other tissues may explain these unfavorable results. The aim of the current study was to examine the role of IGF1 in cardiac myocytes in the absence of secondary effects, and to elucidate downstream signaling pathways and transcriptional regulatory effects of the IGF1 receptor (IGF1R). Activation of the IGF-1 receptor is survival and proliferation in mitosis-competent cells, and growth (hypertrophy) in tissues such as skeletal muscle and cardiac muscle. The IGFR signaling pathway is of critical importance during normal development of mammary gland tissue during pregnancy and lactation. Several growth factors and hormones are involved in this overall process, and IGF-1R is believed to have roles in the differentiation of the cells and a key role in inhibiting apoptosis until weaning is complete. The IGF-1R is implicated in several cancers, most notably breast cancer. It is further implicated in breast cancer by increasing the metastatic potential of the original tumor by inferring the ability to promote vascularisation. A tyrosine kinase inhibitor targeted to IGFR can be used for the treatment of cancers having abnormally high IGFR kinase activity and IGFR kinase disorder diseases.

Kinases such as c-Src, c-Abl, mitogen activated protein (MAP) kinase, phosphotidylinositol-3-kinase (PI3K) AKT, and the epidermal growth factor (EGF) receptor are commonly activated in cancer cells, and are known to contribute to tumorigenesis. Many of these occur in the same signaling pathway—for example, HER-kinase family members (HER1 [EGFR], HER3, and HER4) transmit signals through MAP kinase and PI3 kinase to promote cell proliferation.

TrkA (Tropomyosin-Related Kinase A) is a high affinity catalytic receptor for neurotrophin, Nerve Growth Factor (NGF) and thus mediates the multiple effects of NGF including neuronal differentiation and survival. The TrkA receptor is part of the large family of receptor tyrosine kinases.

PTK disorder disease includes, such as cancer, asarthritis, diabetic retinopathy, restenosis, hepatic cirrhosis, atherosclerosis, angiogensis, glomerulonephritis, diabetic nephropathy, thrombic microangiopathy syndromes, transplant rejection, autoimmune disease, diabetes, and hyperimmune disorders.

Cancers include, without limitation, carcinoma of the bladder, breast, colon, kidney, liver, lung, head and neck, gallbladder, ovary, pancreas, stomach, cervix, thyroid, prostate, skin, hematopoietic tumor of lymphoid lineage (i.e. leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma), hematopoietic tumor of myeloid lineage (i.e. acute myelogenous leukemia, chronic myelogenous leukemia, multiple myelogenous leukemia, myelodysplastic syndrome and promyelocytic leukemia), tumor of mesenchymal origin (i.e. fibrosarcoma and rhabdomyosarcoma), tumor of the central or peripheral nervous system (i.e. astrocytoma, neuroblastoma, glioma and schwannomas), melanoma, seminoma, teratocarcinoma, osteosarcoma, thyroid follicular cancer; and Kaposi's sarcoma.

BRIEF SUMMARY OF THE INVENTION

One embodiment of the invention features azaazulene compounds of formula (I):

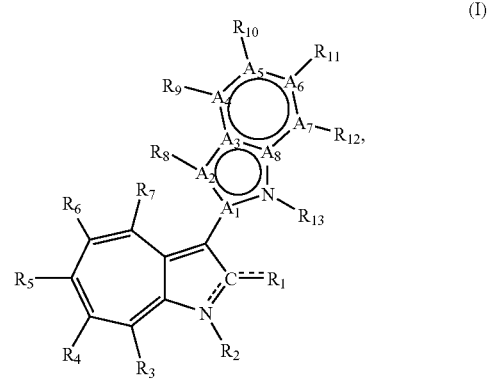

wherein
one of ===== is single bond and the other ===== is double bond;
each of $A_1, A_2, A_3, A_4, A_5, A_6, A_7,$ and $A_8$, independently, is carbon or nitrogen;
$A_1, A_2, A_3, A_4, A_5, A_6, A_7,$ and $A_8$ together with the nitrogen links to $A_1$ and $A_8$ form a 6,5-fused heterocycle having 10 pi electrons;
$R_1$ is O, OR, S, SR, NH2, NHR, NRR', NH, or NR;

each of $R_2$, $R_3$, $R_4$, $R_5$, $R_6$, $R_7$, $R_8$, $R_9$, $R_{10}$, $R_{11}$, $R_{12}$, and $R_{13}$, independently, is null, H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_3$-$C_{20}$ aryl, $C_1$-$C_{20}$ heteroaryl, $NO_2$, NO, $N_3$, SCN, CN, OCN, OR, OC(O)R, OC(S)R, OC(S)OR, OC(O)SR, OC(S)SR, OC(O)NRR', OC(S)NRR'', ONRR', OS(O)R, OS(O)$_2$R, SR, SC(O)R, SC(S)R, SC(S)OR, SC(O)SR, SC(S)SR, SC(O)NRR', SC(S)NRR', S(O)R, S(O)$_2$R, S(O)NRR', S(O)$_2$NRR', S(O)OR, S(O)$_2$OR, NCO, NCS, NRR', N(R)—C(O)R', N(R)—C(O)OR', N(R)—C(S)R', N(R)—C(S)OR', N(C(O)R)—C(O)R', N(R)—S(O)R', N(R)—S(O)OR', N(R)—S(O)$_2$R', N(R)—S(O)$_2$OR', N(R)—OR', N(OR)—C(O)R', N(OR)—C(O)OR', N(OR)—C(S)R', N(OR)—C(S)OR', N(OR)—C(S)SR', N(OR)—S(O)R', N(OR)—S(O)OR', N(OR)—S(O)$_2$R', N(OR)—S(O)$_2$OR', C(O)R, C(O)OR, C(O)NRR', C(O)SR, C(S)R, C(S)OR, C(S)NRR', C(S)SR, C(NR)—R', C(NR)—OR', C(NR)—NR'R'', C(NR)—SR', C(NOR)—R', C(NOR)—OR', C(NOR)—NR'R'', or C(NOR)—SR'; or $R_2$ and $R_3$, $R_3$ and $R_4$, $R_4$ and $R_5$, $R_5$ and $R_6$, $R_6$ and $R_7$, $R_8$ and $R_9$, $R_9$ and $R_{10}$, $R_{10}$ and $R_{11}$, $R_{11}$ and $R_{12}$, or $R_{12}$ and $R_{13}$ together with atoms to which they are attached, are $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_3$-$C_{20}$ aryl, or $C_1$-$C_{20}$ heteroaryl;

in which each of R, R', and R'', independently is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_3$-$C_{20}$ aryl, or $C_1$-$C_{20}$ heteroaryl, or R and R', R and R'' or R' and R'' together with the atom to which they are attached, are $C_1$-$C_{20}$ heterocycloalkyl or $C_1$-$C_{20}$ heterocycloalkenyl, when each of $A_1$, $A_3$, $A_4$, $A_5$, $A_6$, $A_7$, and $A_8$ is carbon, $A_2$ is nitrogen, $C\text{-----}N$ is C=N, and $C\text{-----}R_1$ is C=O, C—OEt, or C—$NH_2$, at least one $R_2$, $R_3$, $R_4$, $R_5$, $R_6$, $R_7$, $R_8$, $R_9$, $R_{10}$, $R_{11}$, and $R_{12}$ is not H.

When $C\text{-----}N$ is C=N, $C\text{-----}R_1$ is C—$R_1$, and when $C\text{-----}R_1$ is C=$R_1$, $C\text{-----}N$ is C—N.

The term "alkyl" refers to a straight or branched hydrocarbon chain radical group having from one to twenty carbon atoms, and which is attached to the rest of the molecule by a single bond, e.g., methyl, ethyl, n-propyl, 1-methylethyl(isopropyl), n-butyl, n-pentyl, 1,1-dimethylethyl(t-butyl), and the like.

The term "alkenyl" refers to a linear or branched hydrocarbon moiety that contains at least one double bond having from two to twenty carbon atoms, and which is attached to the rest of the molecule by a single bond or a double bond, e.g., ethenyl, prop-1-enyl, but-1-enyl, pent-1-enyl, penta-1,4-dienyl, and the like.

The term "alkynyl" refers to a linear or branched hydrocarbon moiety that contains at least one triple bond having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

The term "cycloalkyl" refers to a saturated, mono-bi- or tricyclic hydrocarbon moiety having from three to twenty carbon atoms, and which is saturated and attached to the rest of the molecule by a single bond, e.g., cyclopropyl, cyclobutyl, cyclopentyl, cyclohexyl, decalinyl, norbornane, norbornene, adamantyl, bicyclo[2.2.2]octane and the like.

The term "cycloalkenyl" refers to a non-aromatic, mono-bi- or tricyclic hydrocarbon moiety having from three to twenty carbon atoms and contains at least one double bond, such as cyclohexenyl.

The term "heterocycloalkyl" refers to a saturated, mono-bi- or tricyclic moiety having from one to twenty carbon atoms and at least one ring heteroatom (e.g., N, O, or S), such as 4-tetrahydropyranyl.

The term "heterocycloalkenyl" refers to a non-aromatic, mono-bi- or tricyclic moiety having from one to twenty carbon atoms and at least one ring heteroatom (e.g., N, O, or S) and at least one double bond, such as pyranyl.

The term "aryl" refers to a hydrocarbon moiety having from six to thirty carbon atoms and one or more aromatic rings. Examples of aryl moieties include phenyl (Ph), phenylene, naphthyl, biphenyl, naphthylene, pyrenyl, anthryl, azulenyl, and phenanthryl.

The term "heteroaryl" refers to a moiety having from one to thirty carbon atoms and one or more aromatic rings that contain at least one heteroatom (e.g., N, O, or S). Examples of heteroaryl moieties include, but are not limited to, acridinyl, azaazulenyl, benzimidazolyl, benzindolyl, benzisoxazinyl, benzo[4,6]imidazo[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, .beta.-carbolinyl, carbazolyl, cinnolinyl, dibenzofuranyl, furanyl, imidazolyl, imidazopyridinyl, imidazothiazolyl, indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thiophenyl, triazinyl, and triazolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, $C_3$-$C_{30}$ aryl, $C_3$-$C3_{20}$ aryloxy, $C_1$-$C_{30}$ heteroaryl, $C_1$-$C_{30}$ heteroaryloxy, amino, $C_1$-$C_{20}$ alkylamino, $C_1$-$C_{20}$ dialkylamino, $C_3$-$C_{20}$ arylamino, $C_6$-$C_{40}$ diarylamino, $C_1$-$C_{20}$ alkylsulfonamino, $C_3$-$C_{20}$ arylsulfonamino, $C_1$-$C_{10}$ alkylimino, $C_3$-$C_{20}$ arylimino, $C_1$-$C_{10}$ alkylsulfonimino, $C_3$-$C_{20}$ arylsulfonimino, hydroxyl, halo, thio, $C_1$-$C_{10}$ alkylthio, $C_3$-$C_{20}$ arylthio, $C_1$-$C_{10}$ alkylsulfonyl, $C_3$-$C_{20}$ arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents. Cycloalkyl, cycloalkenyl, heterocycloalkyl, heterocycloalkenyl, aryl, and heteroaryl can also be fused with each other.

Another embodiment of the invention features a method for treating cancer. The method includes administering to a subject in need thereof an effective amount of one or more azaazulene compounds of formula (I) shown above. Examples of cancer include leukemia (e.g., acute myelogenous leukemia), gastrointestinal cancer (e.g., a gastrointestinal stromal tumor), kidney cancer (e.g., metastatic renal cell carcinoma), or lung cancer (e.g., small cell lung cancer).

The term "treating" or "treatment" refers to administering one or more azaazulene compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

Another embodiment of the invention encompasses a pharmaceutical composition that contains an effective amount of at least one of the above-mentioned azaazulene compound and a pharmaceutically acceptable carrier.

The azaazulene compounds described above include the compounds themselves, as well as their salts, prodrugs, solvates, complexes, or radioisotope labeled derivatives, if applicable. A salt, for example, can be formed between an anion and a positively charged group (e.g., amino) on an azaazulene compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on an azaazulene compound. Suitable cations include sodium ion, potassium ion, magnesium ion, calcium ion, and an ammonium cation such as tetramethylammonium ion. The azaazulene compounds also include those salts containing quaternary nitrogen atoms. Examples of prodrugs include esters and other pharmaceutically acceptable derivatives, which, upon administration to a subject, are capable of providing active azaazulene compounds. A solvate refers to a molecule formed between an active azaazulene compound and a pharmaceutically acceptable solvent. Examples of pharmaceutically acceptable solvents include water, ethanol, isopropanol, ethyl acetate, acetic acid, and ethanolamine. A complex can be formed between an active azaazulene compound and a complexing agent (e.g., cyclodextrins or cyclophanes) or between an active azaazulene compound and an inorganic cation (e.g., zinc, magnesium, calcium, silver, or copper cations).

Also within the scope of this invention is a composition containing one or more of the azaazulene compounds described above for use in treating cancer, and the use of such a composition for the manufacture of a medicament for the just-mentioned treatment. The cancer mentioned above may comprise acute myeloid leukemia (AML).

The invention further provides a method of inhibiting the activity of protein kinase in a subject. The method includes administering to a cell in need thereof an effective amount of one or more azaazulene compounds of formula (I) shown above. Examples of protein kinase include AMPK, BLK, CSF1R, FGFR, FGR, FLT3, KDR, KIT, LCK, LYN, MAP4K5, NTRK, PHKG1, RET, SRC, STK, and YES1. In addition, in the method of inhibiting the activity of protein kinase in a subject of the invention, the subject may be a cancer cell, and the cancer cell may comprise a cell of acute myeloid leukemia.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIG. 1 shows the mean tumor volumes of the MV4-11 subcutaneous tumor xenograft model in BALB/c mice after B26 or vehicle administration.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The azaazulene compounds in this invention can be prepared by methods well known in the art. For example, the following schemes illustrate the typical synthetic routes for preparing the azaazulene compounds in this invention.

The intermediates for constructing the azaazulene cores can be synthesized by following scheme.

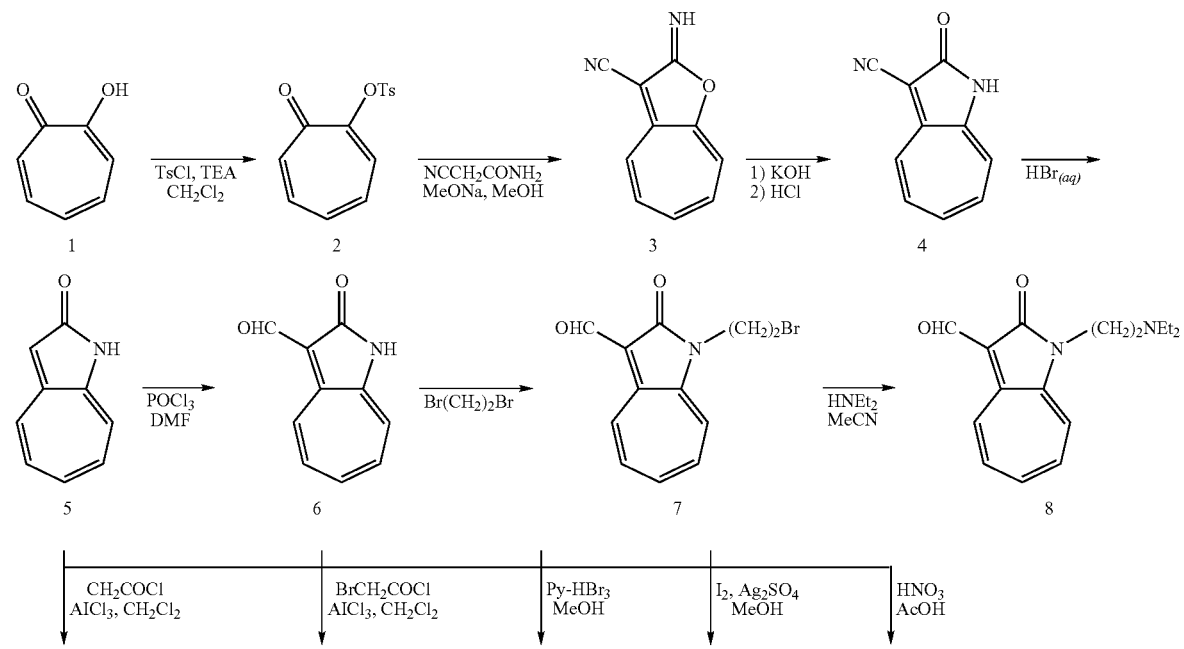

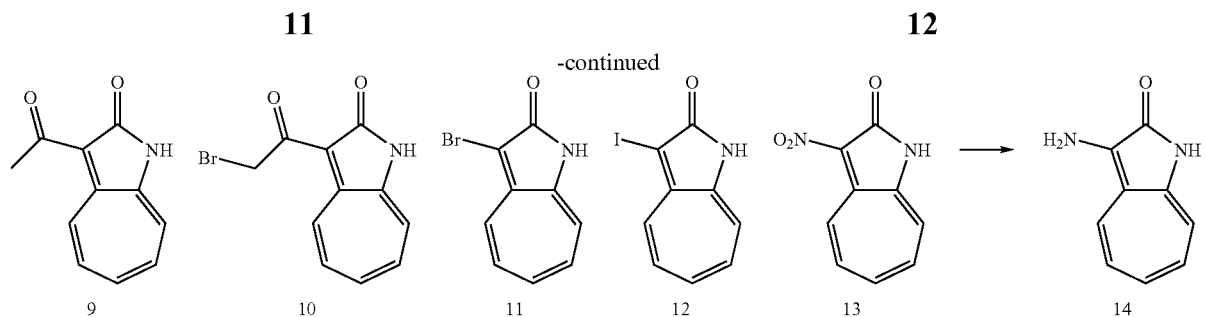
The azaazulene compounds in this invention containing indole type 6,5-fused heterocycle can be synthesized by following scheme.
The azaazulene compounds in this invention containing benzimidazole type 6,5-fused heterocycle can be synthesized by following scheme.
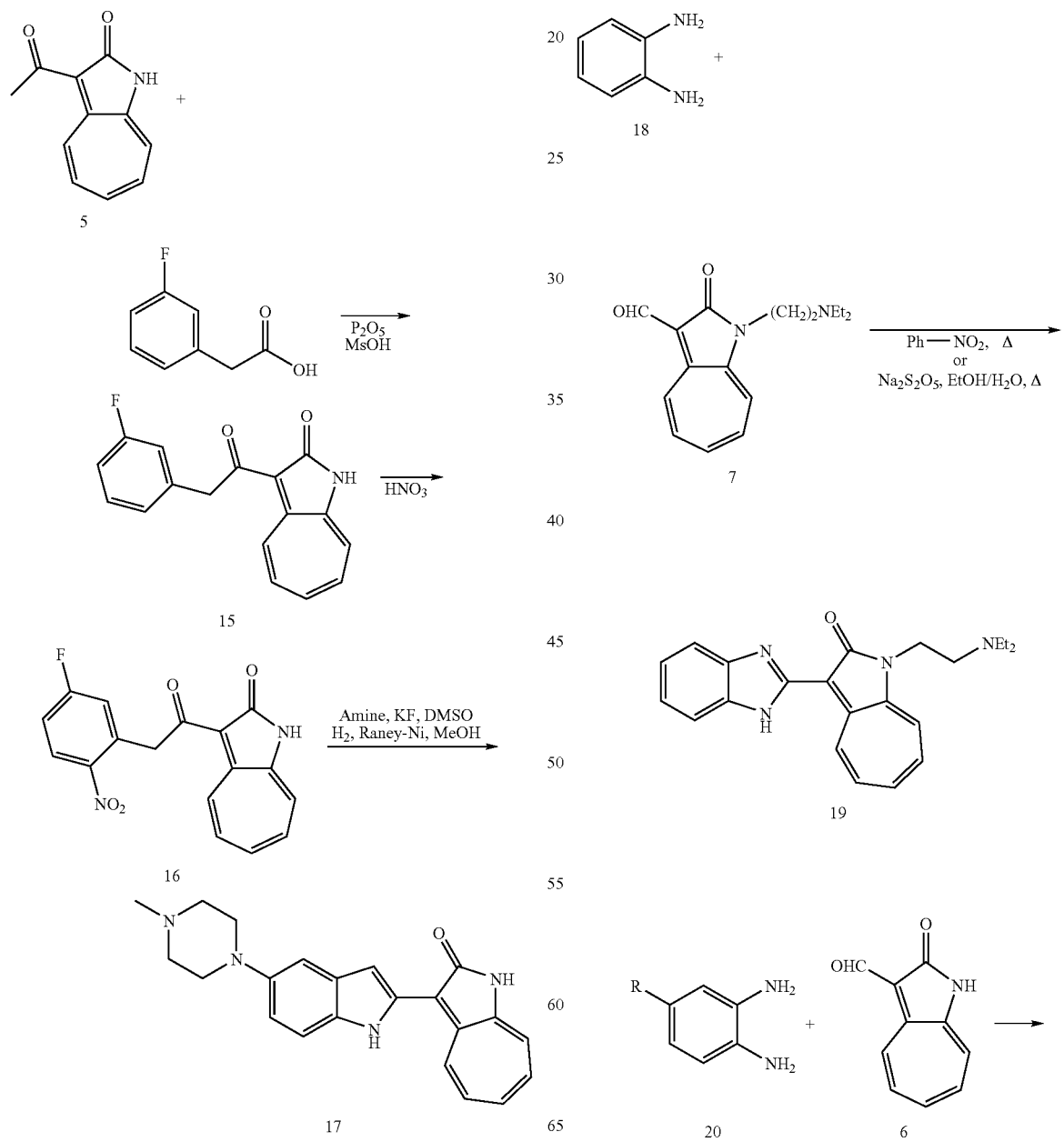

-continued
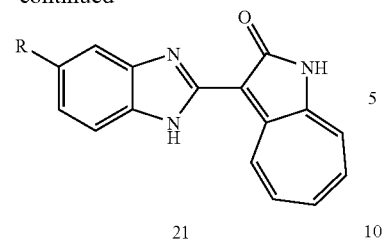
21
21a, R = H
21b, R = F
21c, R = CF$_3$
21d, R = OH
21e, R = NO$_2$
21f, R = NH$_2$
21g, R = COOH
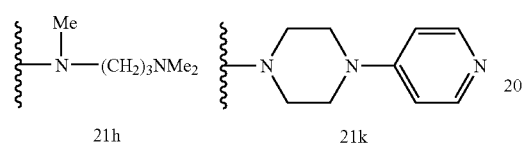
21h    21k
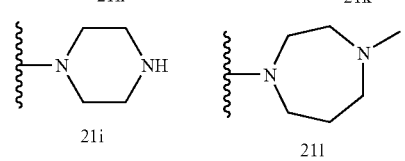
21i    21l
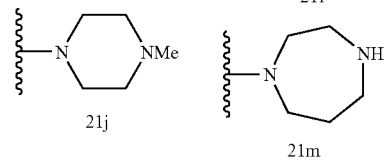
21j    21m
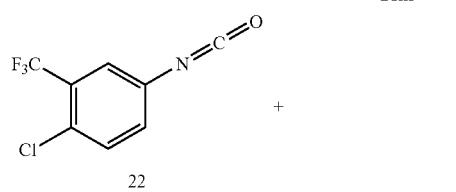
22
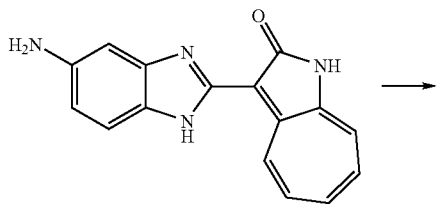
21f
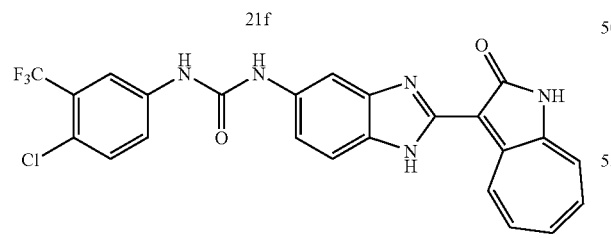
21n
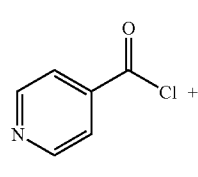
23
-continued
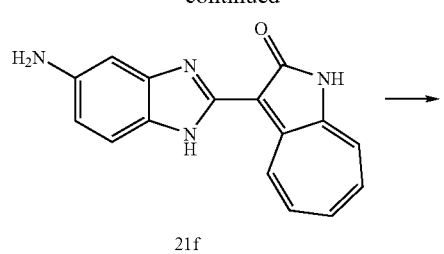
21f
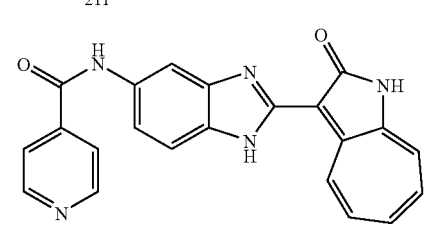
21o
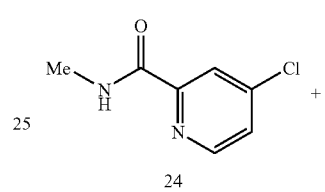
24
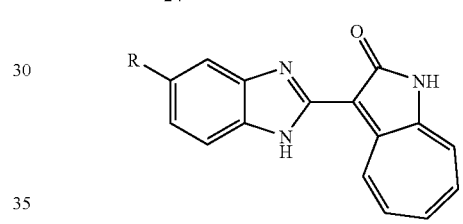
21d, 21f
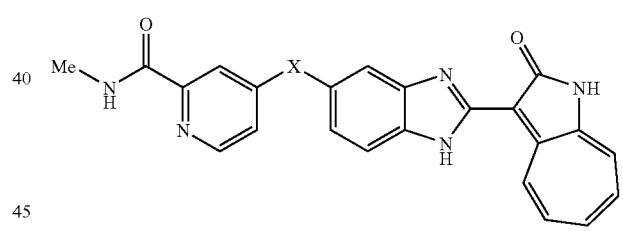
21p, X = NH
21q, X = O
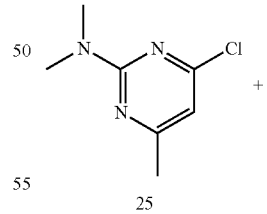
25
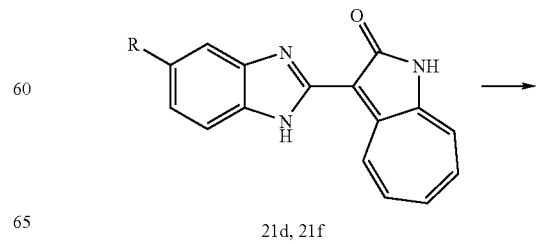
21d, 21f -continued
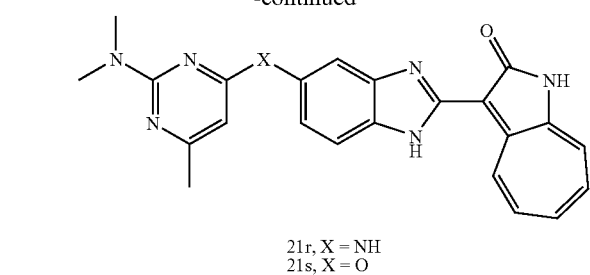
21r, X = NH
21s, X = O
R₁R₂NH +
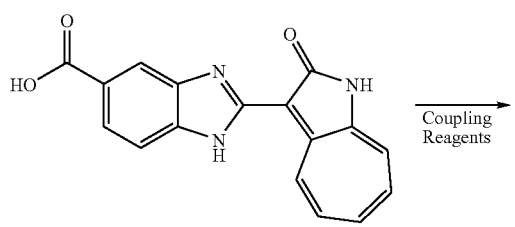
21g
→ Coupling Reagents
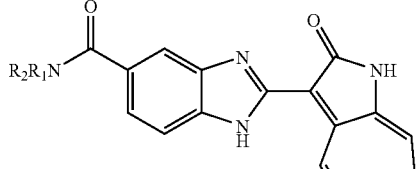
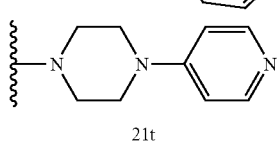
21t
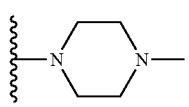
21u
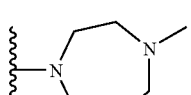
21v
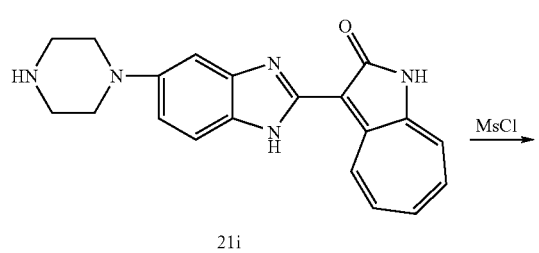
21i
→ MsCl
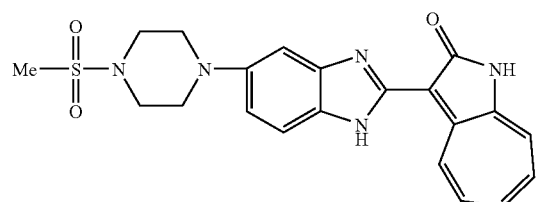
21w
-continued
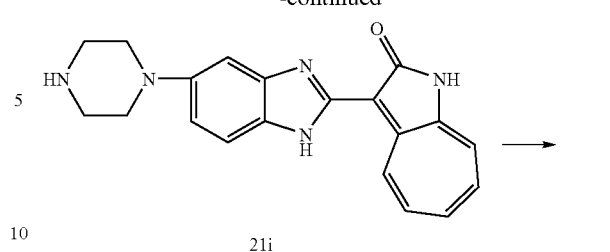
21i
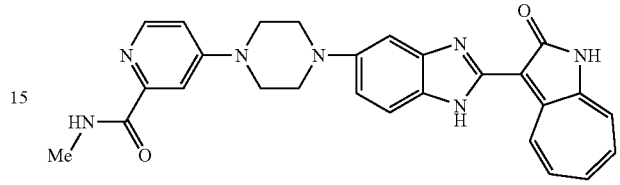
21x
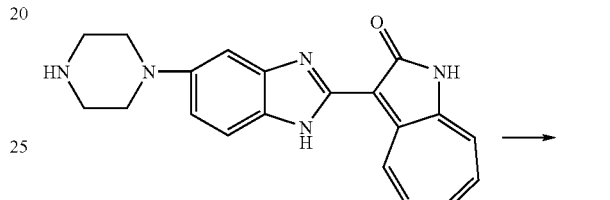
21i
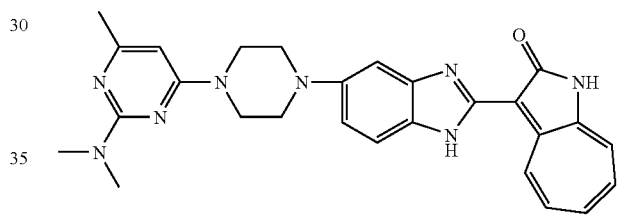
21y
The azaazulene compounds in this invention containing 3H-imidazo[4,5-b]pyridine, 3H-imidazo[4,5-c]pyridine and purine type 6,5-fused heterocycles can be synthesized by following scheme.
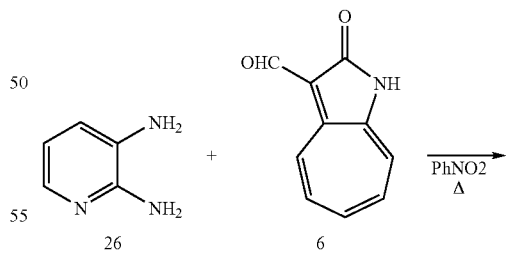
26        6
→ PhNO2 Δ
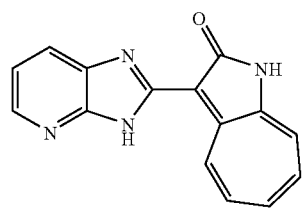
27

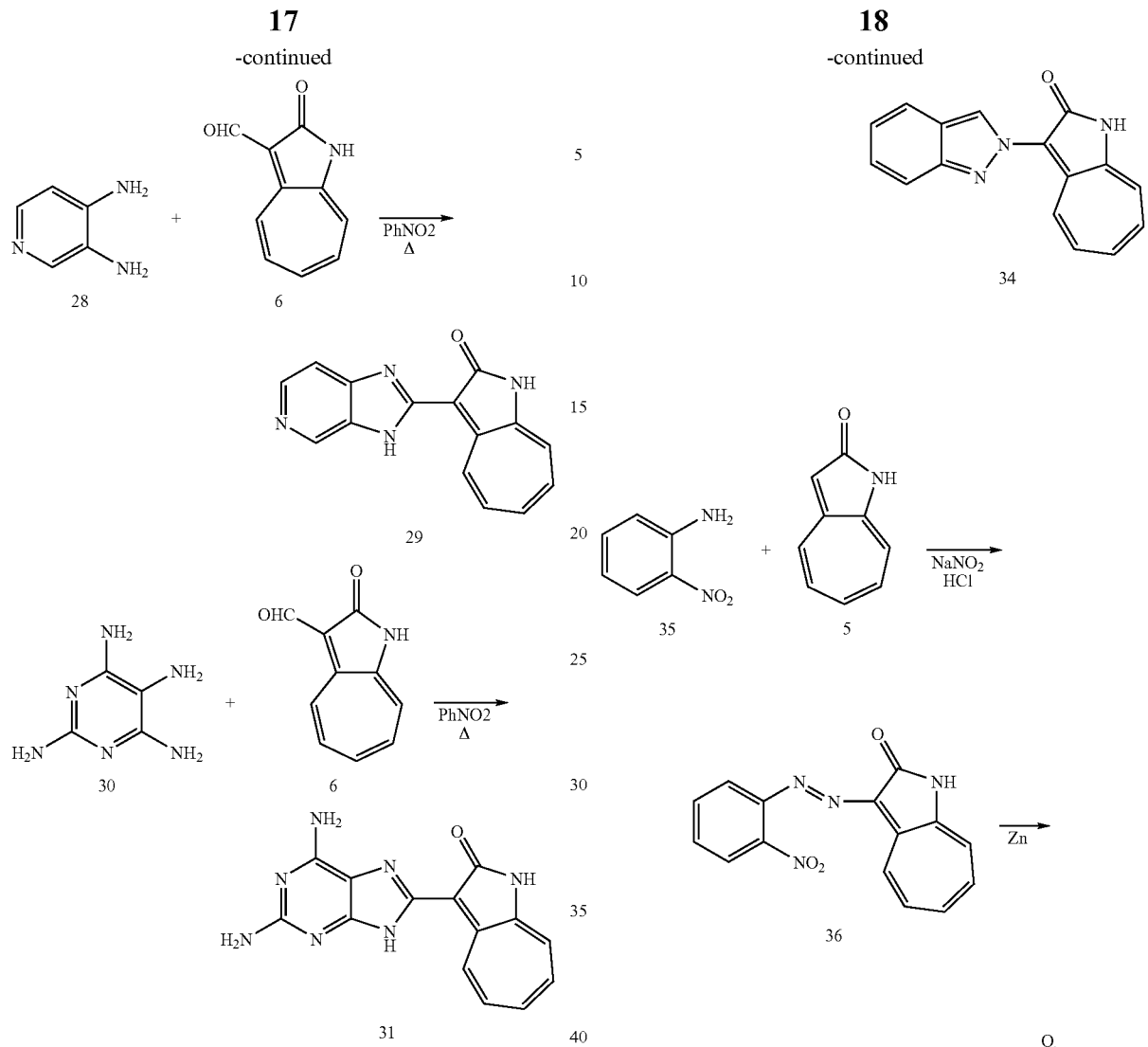

The azaazulene compounds in this invention containing 2H-indazole and 2H-benzo[d][1,2,3]triazole type 6,5-fused heterocycles can be synthesized by following scheme.

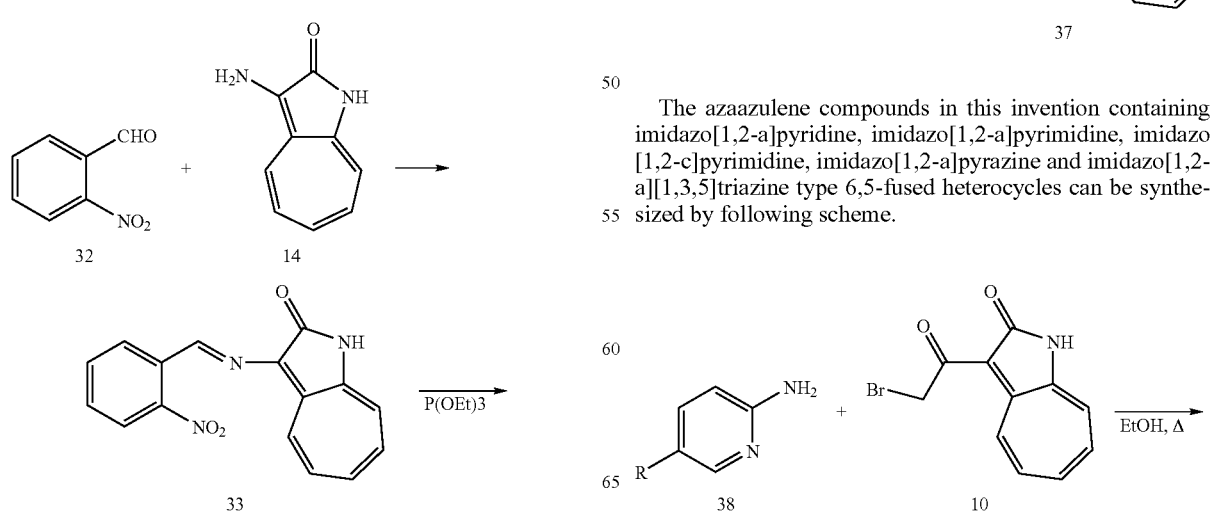

The azaazulene compounds in this invention containing imidazo[1,2-a]pyridine, imidazo[1,2-a]pyrimidine, imidazo[1,2-c]pyrimidine, imidazo[1,2-a]pyrazine and imidazo[1,2-a][1,3,5]triazine type 6,5-fused heterocycles can be synthesized by following scheme.

-continued
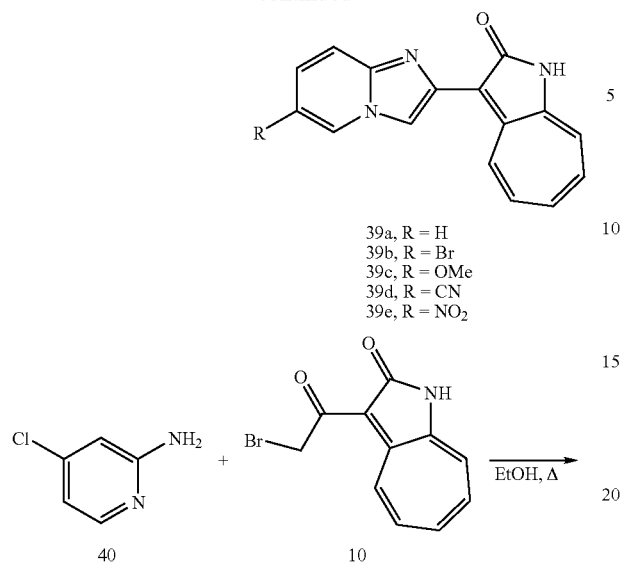
39a, R = H
39b, R = Br
39c, R = OMe
39d, R = CN
39e, R = NO₂
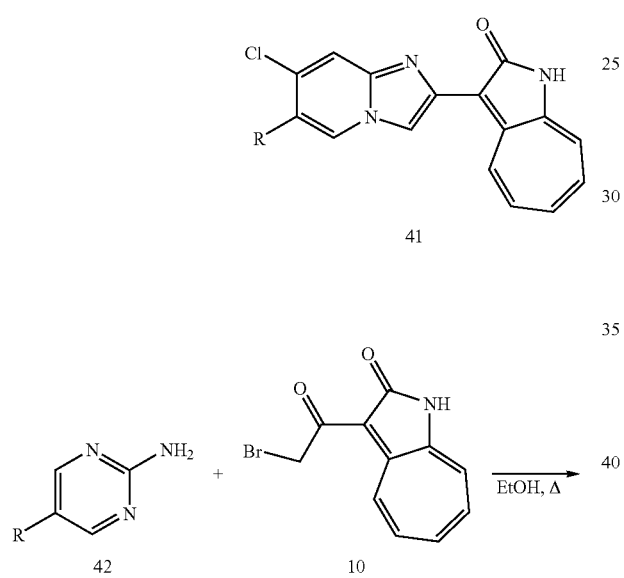
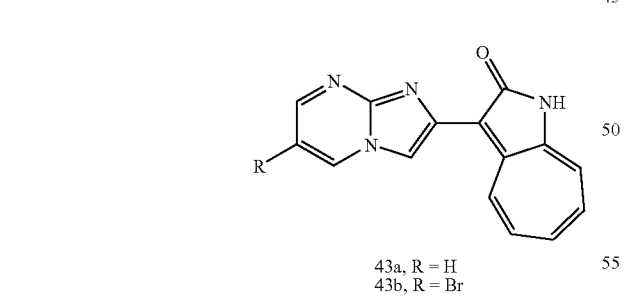
43a, R = H
43b, R = Br
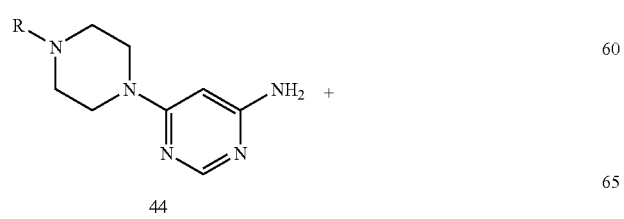
44
-continued
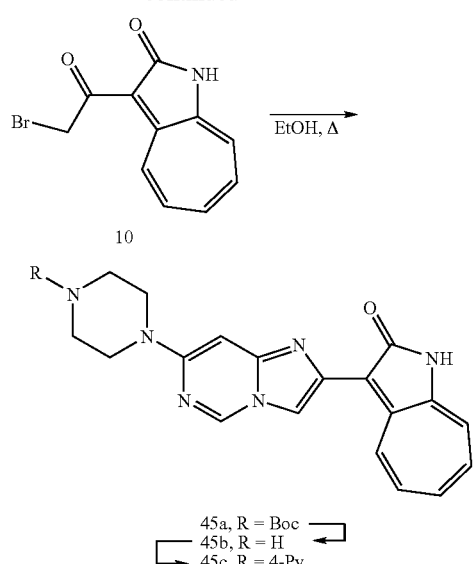
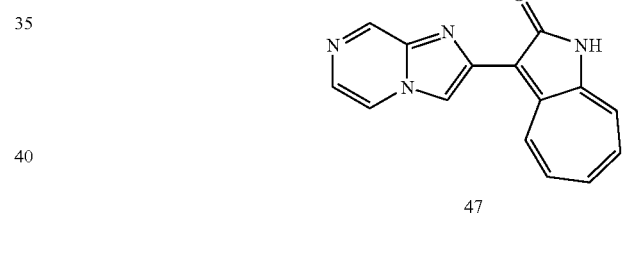
45a, R = Boc
45b, R = H
45c, R = 4-Py
45d, R = Ms
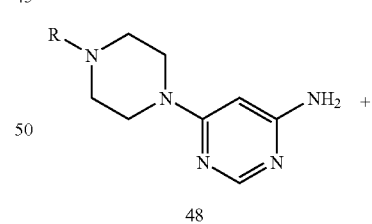
47
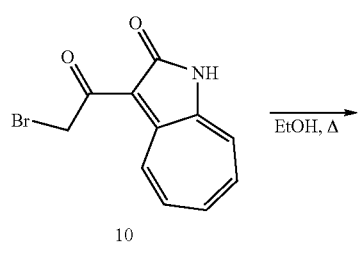

-continued

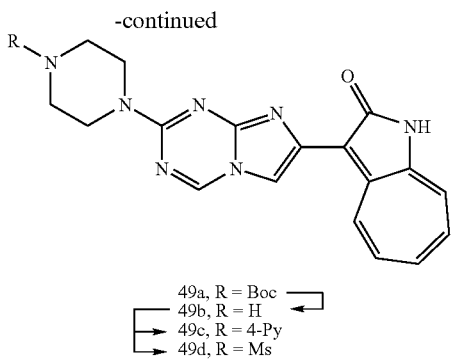

49a, R = Boc
49b, R = H
49c, R = 4-Py
49d, R = Ms

As shown in the above schemes, a base can be used to facilitate synthesizing the azaazulene compounds of the invention. Preferably, the base is a compound containing a nitrogen atom, such as ammonia, methylamine, trimethylamine, triethylamine, aniline, dimethylaminopyridine, proline, N-methylaniline, 1,8-diazabicyclo[5.4.0]undec-7-ene, diisopropylethylamine, pyrrolidine, piperidine, sodium amide, lithium diisopropylamide, and sodium hexamethyldisilazanide. Other organic or inorganic bases can also be used in the reaction set forth in the above scheme. Examples of organic or inorganic bases that do not contain a nitrogen atom include carbonates, bicarbonates, acetates, formates, alkyl lithium compounds, aryl lithium compounds, metal alkoxides, Grignard reagents, hydroxides, phosphates, bisulfates, hydrosulfides, and hydrides.

As shown in the above schemes, an acid can be used to facilitate synthesizing the azaazulene compounds of the invention. Examples of organic or inorganic acid include acetic, benzenesulfonic, benzoic, camphorsulfonic, citric, ethenesulfonic, dichloroacetic, formic, fumaric, gluconic, glutamic, hippuric, hydrobromic, hydrochloric, hydrofluoric, hydroiodic, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic, trifluoroacetic, trifluoromethanesulfonic acid and the like.

As shown in the above schemes, a coupling reagent can be used to facilitate synthesizing the azaazulene compounds of the invention. Examples of coupling reagent include BOP, CDI, DCC, DEPBT, DIC, EDC.HCl, HATU, HBTU, HCTU, PyBOP, PyBrOP, TATU, TBTU, TDBTU, TSTU and the like.

As shown in the above schemes, a metal-containing catalyst can be used to facilitate synthesizing the azaazulene compounds of the invention. Examples of the metal include Fe, Ni, Co, Cu, Au, Pd, Pt, Rh and Ru. A ligand may exist to facilitate the catalytic ability of the metal.

The reaction set forth in the above scheme can take place in the presence of a solvent, which can be either protic or aprotic. Examples of protic solvents include alcohols and water. Examples of aprotic solvents include hexane, toluene, benzene, methylene chloride, chloroform, dimethylformamide, dimethylsulfoxide, and tetrahydrofuran. The reaction set forth in the above scheme can also take place in the absence of a solvent.

An azaazulene compound thus synthesized can be purified by a suitable method such as column chromatography, high-pressure liquid chromatography, distillation, sublimation or recrystallization.

Other azaazulene compounds can be prepared using other suitable starting materials through the above synthetic routes and others known in the art. The methods described above may also additionally include steps, either before or after the steps described specifically herein, to add or remove suitable protecting groups in order to ultimately allow synthesis of the azaazulene compounds. In addition, various synthetic steps may be performed in an alternate sequence or order to give the desired compounds. Synthetic chemistry transformations and protecting group methodologies (protection and deprotection) useful in synthesizing applicable azaazulene compounds are known in the art and include, for example, those described in R. Larock, Comprehensive Organic Transformations, VCH Publishers (1989); T. W. Greene and P. G. M. Wuts, Protective Groups in Organic Synthesis, 2.sup.nd Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The azaazulene compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one azaazulene compound described above and a pharmaceutical acceptable carrier or salt. Further, this invention covers a method of administering an effective amount of one or more of the azaazulene compounds to a patient having cancer. "An effective amount" refers to the amount of an active azaazulene compound that is required to confer a therapeutic effect on the treated subject. Effective doses will vary, as recognized by those skilled in the art, depending on the types of diseases treated, route of administration, excipient usage, and the possibility of co-usage with other therapeutic treatment. The pharmaceutically acceptable carrier can include solvents, dispersion media, coatings, antibacterial and antifungal agents, isotonic and absorption delaying agents, and the like.

The azaazulene compounds of the invention are useful for detecting either azaazulene or 6,5-fused heterocycle recognition sites. An azaazulene or 6,5-fused heterocycle recognition site can be any enzyme, receptor, channel, transporter, functional protein, RNA or DNA site that binds to the azaazulene or 6,5-fused heterocycle moiety of an azaazulene compound of the invention. Thus, the compounds of the invention can be used as diagnostic agents, prognostic agents, molecular probes, separation tools and therapeutic agents relating to diseases or disorders associated with such an enzyme, receptor, channel, transporter, functional protein, RNA or DNA.

Suitable salts for the components to be employed according to the present subject matter are also those with inorganic cations, for example alkali metal salts, in particular sodium, potassium, or ammonium salts, alkaline earth metal salts such as, in particular, the magnesium or calcium salts, as well as salts with bi- or tetravalent cations, for example the zinc, aluminum, or zirconium salts. Also contemplated are salts with organic bases, such as dicyclohexylamine salts; methyl-D-glucamine; and salts with amino acids, such as arginine, lysine, histidine, glutamine and so forth. Also, the basic nitrogen-containing groups can be quaternized with such agents as: lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Salt-forming agents, for example, low molecular weight alkylamines such as methylamine, ethylamine, or triethylamine can also be employed. Water or oil-soluble or dispersible products are thereby obtained.

To practice the treatment method of the invention, a composition having one or more azaazulene compounds can be administered to a subject (e.g., a mammal) parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active azaazulene compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active azaazulene compound. Examples of other carriers include colloidal silicon oxide, magnesium stearate, cellulose, sodium lauryl sulfate, and D&C Yellow #10.

The azaazulene compounds described above can be preliminarily screened for their efficacy in treating above-described diseases by in vitro assays and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

The invention also provides a method of inhibiting the activity of protein kinase or protein phosphatase in a cell with one of the azaazulene compounds described above. The method includes contacting cells expressing protein kinase or phosphatase with such an azaazulene compound. Protein kinase and phosphatase regulate signaling cascades. The cascades in turn regulate cell growth, migration, differentiation, gene expression, muscle contraction, glucose metabolism, cellular protein synthesis, and regulation of the cell cycle.

The term "protein kinase" refers to a kinase enzyme that modifies other proteins by chemically adding phosphate groups to them (phosphorylation). Examples of the protein kinase includes, but are not limited to, AMPK, BLK, CSF1R, FGFR, FGR, FLT3, KDR, KIT, LCK, LYN, MAP4K5, NTRK, PHKG1, RET, SRC, STK, and YES 1.

The cells of the invention can be derived from cancer patients. The cells are also termed "cancer cells" herein. The cells are isolated from a variety of sources and tissues. For example, the cells can be isolated from a blood sample or from a biopsy. The cell can be a stem cell, a fibroblast, or a lymphoid cell. The cells can be propagated in culture according to cell type and origin of the cells. The cells can be propagated without being immortalized. Alternatively, the cells can be immortalized using a virus or a plasmid bearing an oncogene, or a transforming viral protein, e.g., papilloma E6 or E7 protein.

TABLE 1

Certain exemplary compounds.

| Compound No. | Structure |
|---|---|
| A1 | 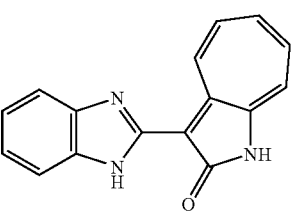 [SMILES: O=c1[nH]c2cccccc-2c1-c1nc2ccccc2[nH]1] |

TABLE 1-continued

Certain exemplary compounds.

| Compound No. | Structure |
|---|---|
| B1 | 3-(1H-benzimidazol-2-yl)-1-(2-(diethylamino)ethyl)cyclohepta[b]pyrrol-2(1H)-one |
| B2 | 3-(5-fluoro-1H-benzimidazol-2-yl)cyclohepta[b]pyrrol-2(1H)-one |
| B3 | 3-(5,6-difluoro-1H-benzimidazol-2-yl)cyclohepta[b]pyrrol-2(1H)-one |
| B4 | 3-(5-(trifluoromethyl)-1H-benzimidazol-2-yl)cyclohepta[b]pyrrol-2(1H)-one |
| B5 | 3-(5-nitro-1H-benzimidazol-2-yl)cyclohepta[b]pyrrol-2(1H)-one · HCl |
| B6 | 3-(5-amino-1H-benzimidazol-2-yl)cyclohepta[b]pyrrol-2(1H)-one |

TABLE 1-continued
Certain exemplary compounds.
| Compound No. | Structure |
|---|---|
| B7 | 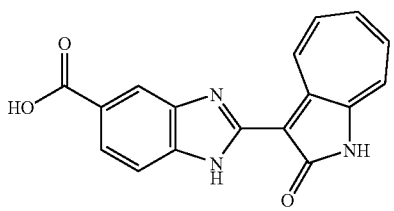 [SMILES: O=C(O)c1ccc2[nH]c(-c3c4cccccc-4[nH]c3=O)nc2c1] |
| B8 | 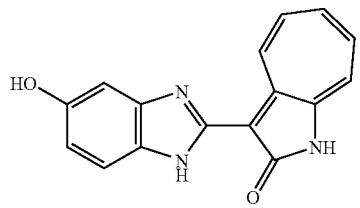 [SMILES: O=c1[nH]c2cccccc-2c1-c1nc2cc(O)ccc2[nH]1] |
| B9 | 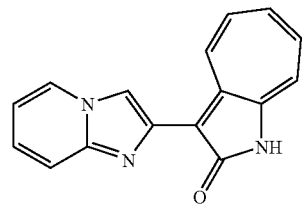 [SMILES: O=c1[nH]c2cccccc-2c1-c1cn2ccccc2n1] |
| B10 | 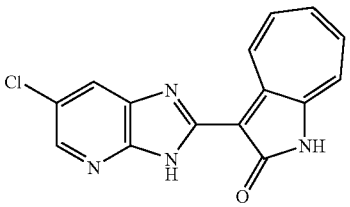 [SMILES: O=c1[nH]c2cccccc-2c1-c1nc2cc(Cl)cnc2[nH]1] |
| B11 | 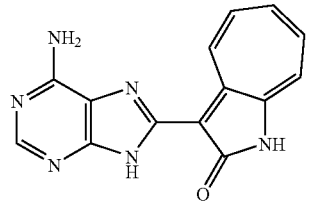 [SMILES: Nc1ncnc2[nH]c(-c3c4cccccc-4[nH]c3=O)nc12] |
| B12 | 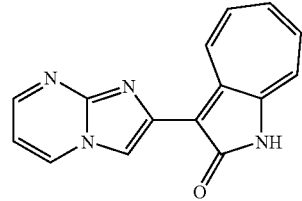 [SMILES: O=c1[nH]c2cccccc-2c1-c1cn2cccnc2n1] |
| B13 | 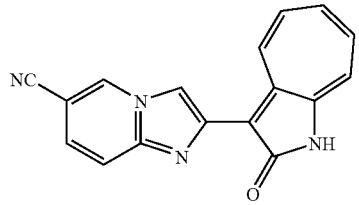 |

TABLE 1-continued

Certain exemplary compounds.

| Compound No. | Structure |
|---|---|
| B14 | 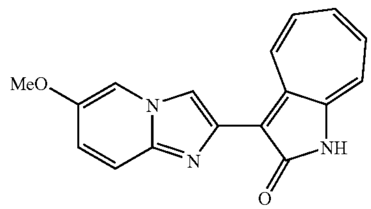 [SMILES: COc1ccc2nc(-c3c4cccccc-4[nH]c3=O)cn2c1] |
| B15 | 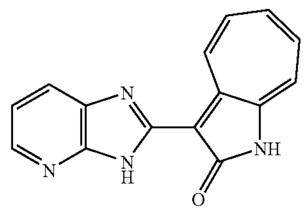 [SMILES: O=c1[nH]c2cccccc-2c1-c1nc2cccnc2[nH]1] |
| B16 | 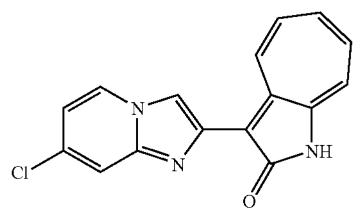 [SMILES: O=c1[nH]c2cccccc-2c1-c1cn2ccc(Cl)cc2n1] |
| B17 | 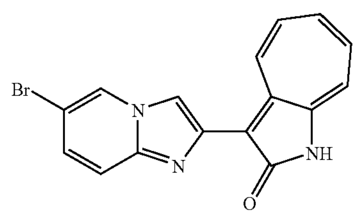 [SMILES: O=c1[nH]c2cccccc-2c1-c1cn2cc(Br)ccc2n1] |
| B18 | 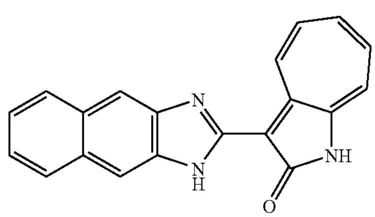 [SMILES: O=c1[nH]c2cccccc-2c1-c1nc2cc3ccccc3cc2[nH]1] |
| B19 | 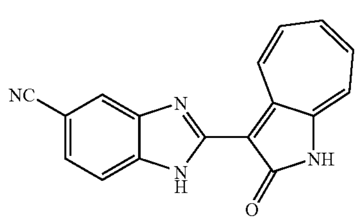 |
| B20 | 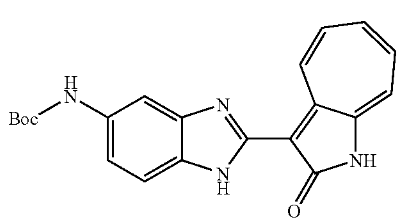 [SMILES: CC(C)(C)OC(=O)Nc1ccc2[nH]c(-c3c4cccccc-4[nH]c3=O)nc2c1] |

TABLE 1-continued

Certain exemplary compounds.

| Compound No. | Structure |
| --- | --- |
| B21 | 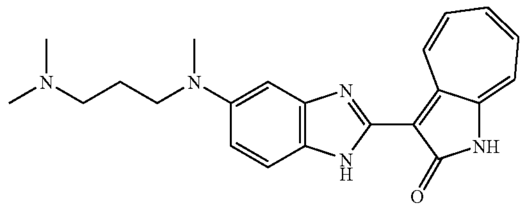 [SMILES: CN(C)CCCN(C)c1ccc2[nH]c(-c3c4cccccc-4[nH]c3=O)nc2c1] |
| B22 | 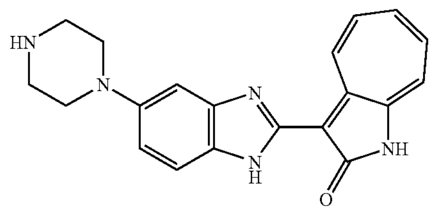 [SMILES: O=c1[nH]c2cccccc-2c1-c1nc2cc(N3CCNCC3)ccc2[nH]1] |
| B23 | 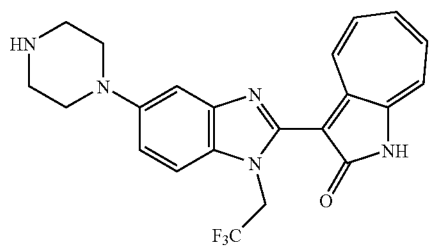 [SMILES: O=c1[nH]c2cccccc-2c1-c1nc2cc(N3CCNCC3)ccc2n1CC(F)(F)F] |
| B24 | 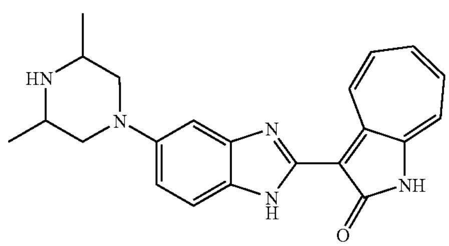 [SMILES: CC1CN(c2ccc3[nH]c(-c4c5cccccc-5[nH]c4=O)nc3c2)CC(C)N1] |
| B25 | 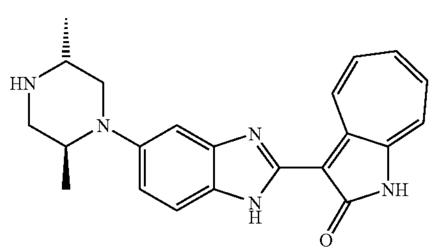 |
| B26 | 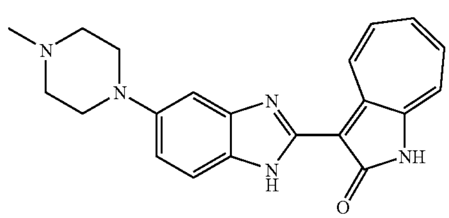 |

TABLE 1-continued

Certain exemplary compounds.

| Compound No. | Structure |
|---|---|
| B27 | 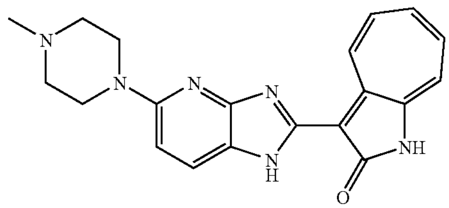 [SMILES: CN1CCN(c2ccc3[nH]c(-c4c5cccccc-5[nH]c4=O)nc3n2)CC1] |
| B28 | 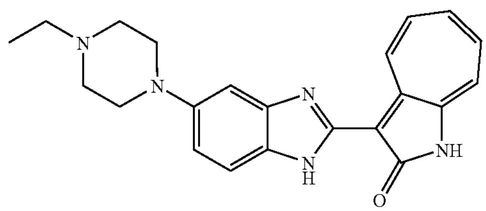 |
| B29 | 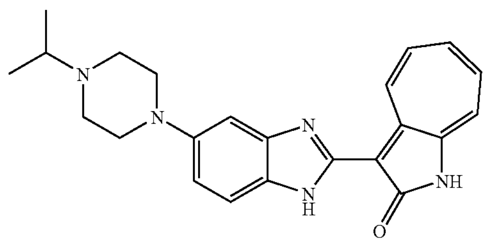 |
| B30 | 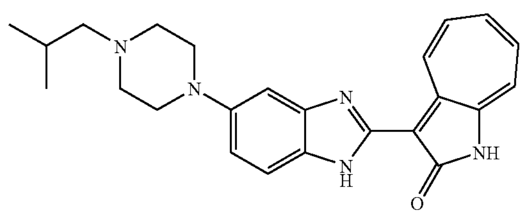 [SMILES: CC(C)CN1CCN(c2ccc3[nH]c(-c4c5cccccc-5[nH]c4=O)nc3c2)CC1] |
| B31 | 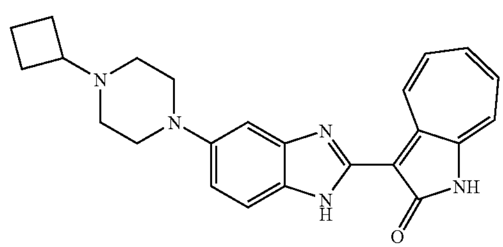 [SMILES: O=c1[nH]c2cccccc-2c1-c1nc2cc(N3CCN(C4CCC4)CC3)ccc2[nH]1] |
| B32 | 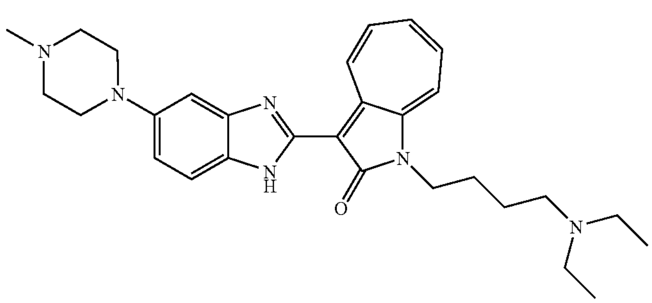 [SMILES: CCN(CC)CCCCn1c2cccccc-2c(-c2nc3cc(N4CCN(C)CC4)ccc3[nH]2)c1=O] |

TABLE 1-continued

Certain exemplary compounds.

| Compound No. | Structure |
|---|---|
| B33 | 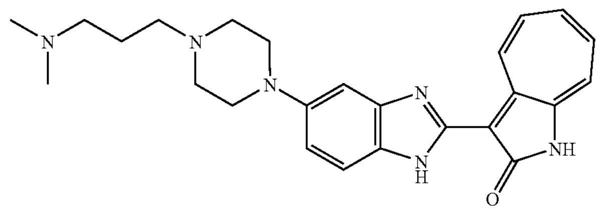 [SMILES: CN(C)CCCN1CCN(c2ccc3[nH]c(-c4c5cccccc-5[nH]c4=O)nc3c2)CC1] |
| B34 | 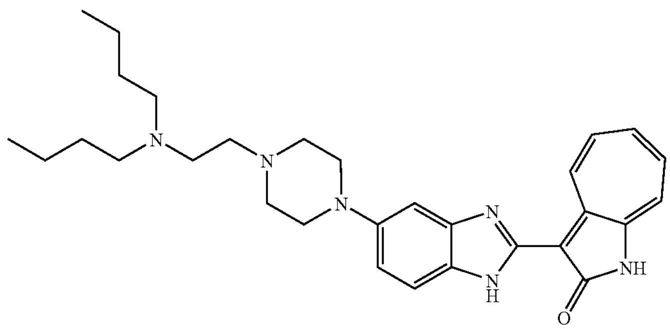 [SMILES: CCCCN(CCCC)CCN1CCN(c2ccc3[nH]c(-c4c5cccccc-5[nH]c4=O)nc3c2)CC1] |
| B35 | 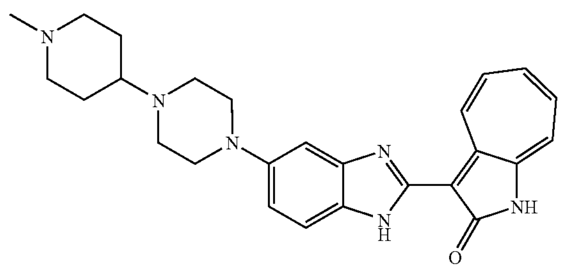 [SMILES: CN1CCC(N2CCN(c3ccc4[nH]c(-c5c6cccccc-6[nH]c5=O)nc4c3)CC2)CC1] |
| B36 | 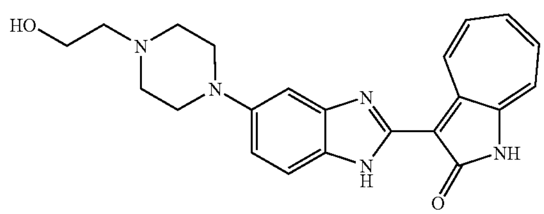 [SMILES: O=c1[nH]c2cccccc-2c1-c1nc2cc(N3CCN(CCO)CC3)ccc2[nH]1] |
| B37 | 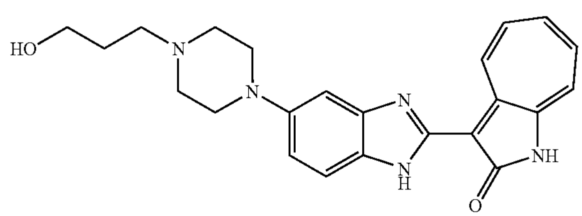 [SMILES: O=c1[nH]c2cccccc-2c1-c1nc2cc(N3CCN(CCCO)CC3)ccc2[nH]1] |
| B38 | 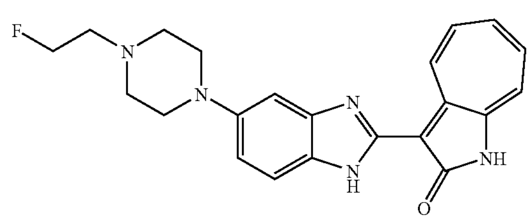 [SMILES: O=c1[nH]c2cccccc-2c1-c1nc2cc(N3CCN(CCF)CC3)ccc2[nH]1] |

TABLE 1-continued
Certain exemplary compounds.
| Compound No. | Structure |
|---|---|
| B39 | 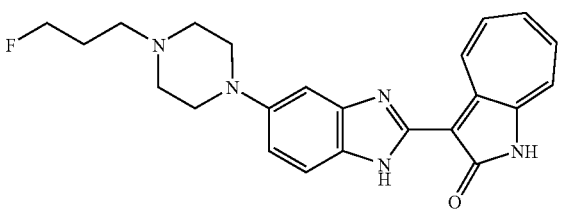 [SMILES: O=c1[nH]c2cccccc-2c1-c1nc2cc(N3CCN(CCCF)CC3)ccc2[nH]1] |
| B40 | 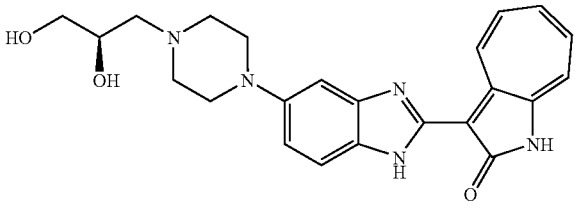 [SMILES: O=c1[nH]c2cccccc-2c1-c1nc2cc(N3CCN(C[C@@H](O)CO)CC3)ccc2[nH]1] |
| B41 | 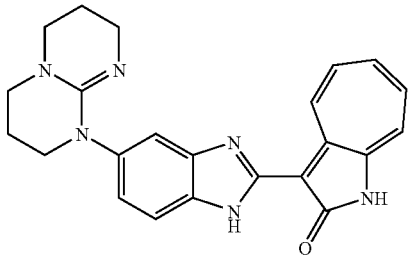 [SMILES: O=c1[nH]c2cccccc-2c1-c1nc2cc(N3CCCN4CCCN=C43)ccc2[nH]1] |
| B42 | 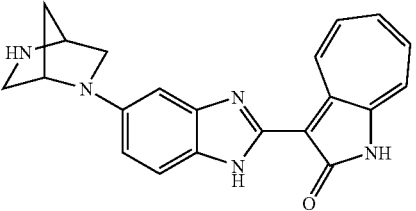 [SMILES: O=c1[nH]c2cccccc-2c1-c1nc2cc(N3CC4CC3CN4)ccc2[nH]1] |
| B43 | 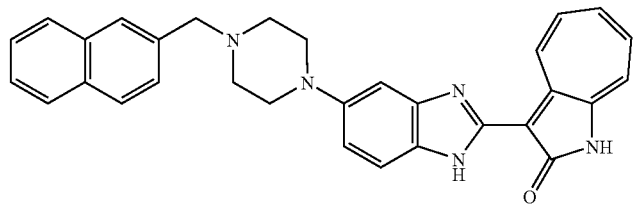 [SMILES: O=c1[nH]c2cccccc-2c1-c1nc2cc(N3CCN(Cc4ccc5ccccc5c4)CC3)ccc2[nH]1] |
| B44 | 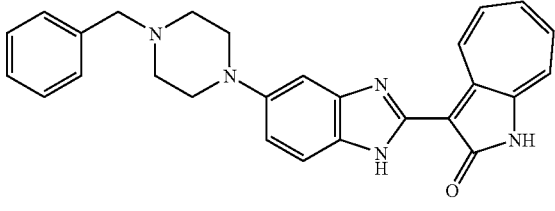 [SMILES: O=c1[nH]c2cccccc-2c1-c1nc2cc(N3CCN(Cc4ccccc4)CC3)ccc2[nH]1] |

TABLE 1-continued

Certain exemplary compounds.

| Compound No. | Structure |
|---|---|
| B45 | 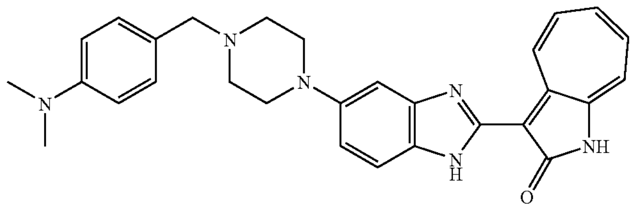 [SMILES: CN(C)c1ccc(CN2CCN(c3ccc4[nH]c(-c5c6cccccc-6[nH]c5=O)nc4c3)CC2)cc1] |
| B46 | 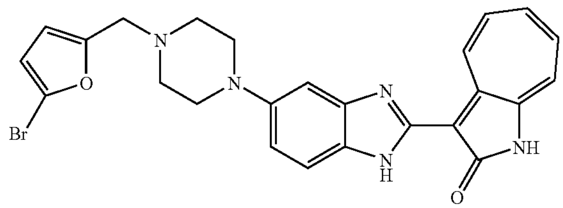 [SMILES: O=c1[nH]c2cccccc-2c1-c1nc2cc(N3CCN(Cc4ccc(Br)o4)CC3)ccc2[nH]1] |
| B47 | 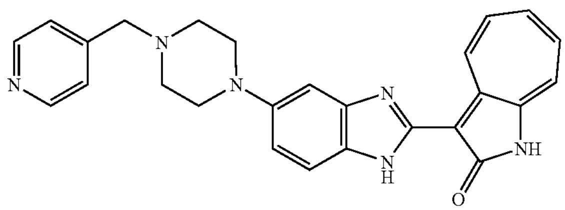 [SMILES: O=c1[nH]c2cccccc-2c1-c1nc2cc(N3CCN(Cc4ccncc4)CC3)ccc2[nH]1] |
| B48 | 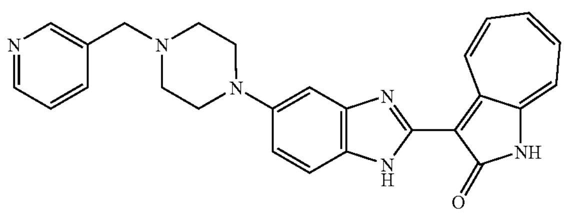 [SMILES: O=c1[nH]c2cccccc-2c1-c1nc2cc(N3CCN(Cc4cccnc4)CC3)ccc2[nH]1] |
| B49 | 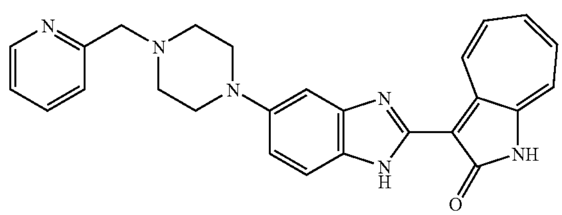 [SMILES: O=c1[nH]c2cccccc-2c1-c1nc2cc(N3CCN(Cc4ccccn4)CC3)ccc2[nH]1] |
| B50 | 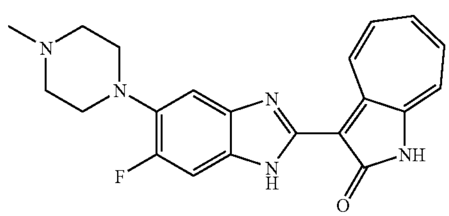 [SMILES: CN1CCN(c2cc3nc(-c4c5cccccc-5[nH]c4=O)[nH]c3cc2F)CC1] |
| B51 | 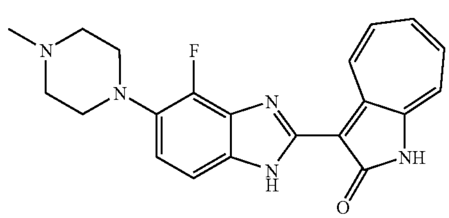 [SMILES: CN1CCN(c2ccc3[nH]c(-c4c5cccccc-5[nH]c4=O)nc3c2F)CC1] |

TABLE 1-continued

Certain exemplary compounds.

| Compound No. | Structure |
| --- | --- |
| B52 | 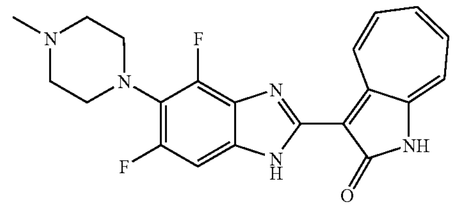 [SMILES: CN1CCN(c2c(F)cc3[nH]c(-c4c5cccccc-5[nH]c4=O)nc3c2F)CC1] |
| B53 | 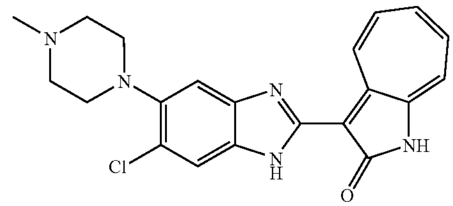 [SMILES: CN1CCN(c2cc3nc(-c4c5cccccc-5[nH]c4=O)[nH]c3cc2Cl)CC1] |
| B54 | 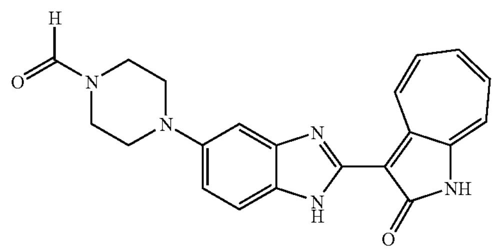 [SMILES: O=CN1CCN(c2ccc3[nH]c(-c4c5cccccc-5[nH]c4=O)nc3c2)CC1] |
| B55 | 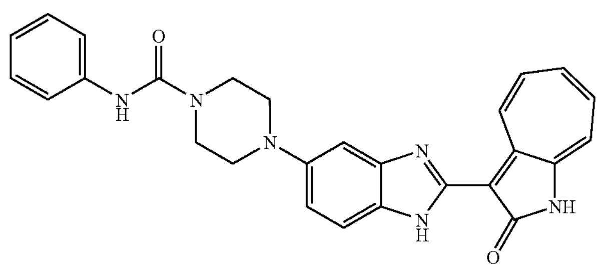 [SMILES: O=C(Nc1ccccc1)N1CCN(c2ccc3[nH]c(-c4c5cccccc-5[nH]c4=O)nc3c2)CC1] |
| B56 | 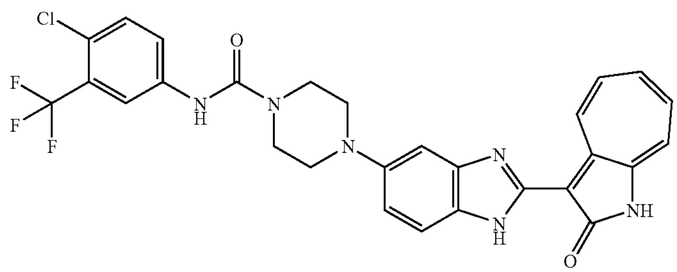 [SMILES: O=C(Nc1ccc(Cl)c(C(F)(F)F)c1)N1CCN(c2ccc3[nH]c(-c4c5cccccc-5[nH]c4=O)nc3c2)CC1] |
| B57 | 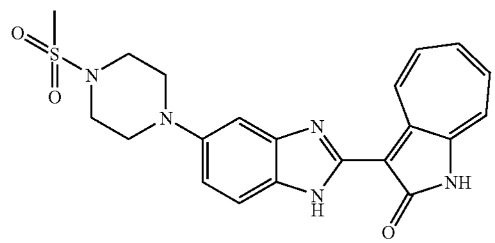 [SMILES: CS(=O)(=O)N1CCN(c2ccc3[nH]c(-c4c5cccccc-5[nH]c4=O)nc3c2)CC1] |

TABLE 1-continued
Certain exemplary compounds.
| Compound No. | Structure |
|---|---|
| B58 | 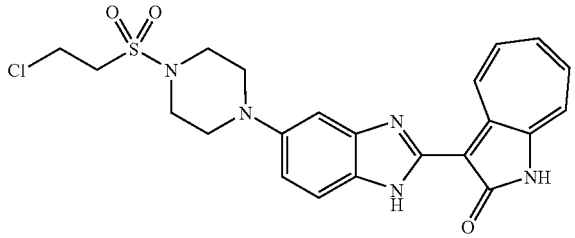 [SMILES: O=c1[nH]c2cccccc-2c1-c1nc2cc(N3CCN(S(=O)(=O)CCCl)CC3)ccc2[nH]1] |
| B59 | 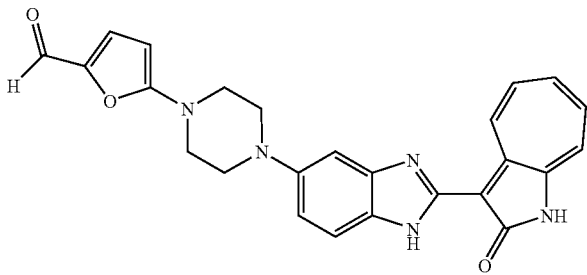 [SMILES: O=Cc1ccc(N2CCN(c3ccc4[nH]c(-c5c6cccccc-6[nH]c5=O)nc4c3)CC2)o1] |
| B60 | 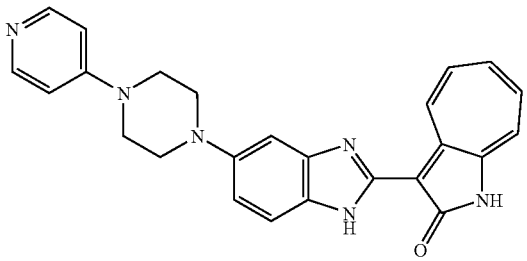 |
| B61 | 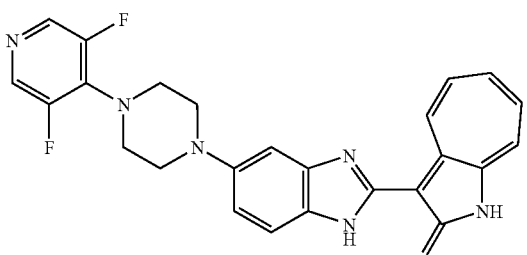 |
| B62 | 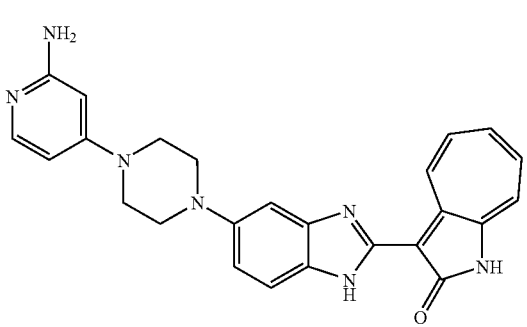 [SMILES: Nc1cc(N2CCN(c3ccc4[nH]c(-c5c6cccccc-6[nH]c5=O)nc4c3)CC2)ccn1] |

TABLE 1-continued

Certain exemplary compounds.

| Compound No. | Structure |
|---|---|
| B63 | 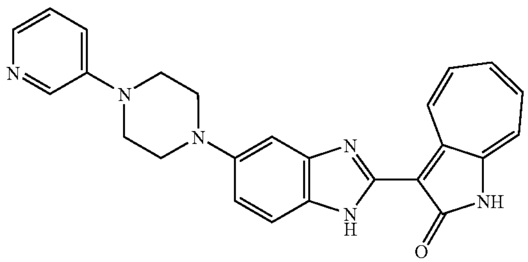 [SMILES: O=c1[nH]c2cccccc-2c1-c1nc2cc(N3CCN(c4cccnc4)CC3)ccc2[nH]1] |
| B64 | 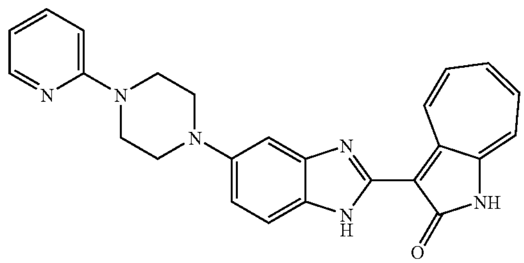 |
| B65 | 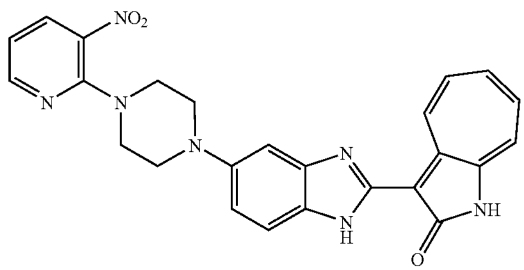 [SMILES: O=c1[nH]c2cccccc-2c1-c1nc2cc(N3CCN(c4ncccc4[N+](=O)[O-])CC3)ccc2[nH]1] |
| B66 | 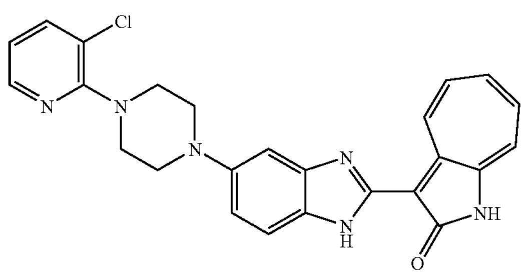 [SMILES: O=c1[nH]c2cccccc-2c1-c1nc2cc(N3CCN(c4ncccc4Cl)CC3)ccc2[nH]1] |
| B67 | 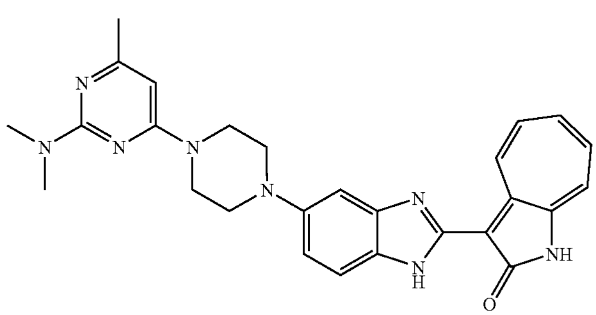 [SMILES: Cc1cc(N2CCN(c3ccc4[nH]c(-c5c6cccccc-6[nH]c5=O)nc4c3)CC2)nc(N(C)C)n1] |

TABLE 1-continued

Certain exemplary compounds.

| Compound No. | Structure |
| --- | --- |
| B68 | 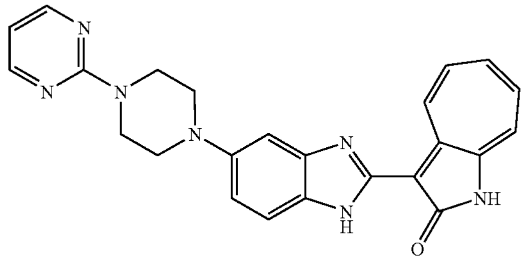 [SMILES: O=c1[nH]c2cccccc-2c1-c1nc2cc(N3CCN(c4ncccn4)CC3)ccc2[nH]1] |
| B69 | 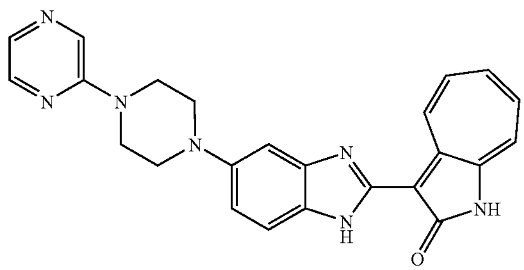 [SMILES: O=c1[nH]c2cccccc-2c1-c1nc2cc(N3CCN(c4cnccn4)CC3)ccc2[nH]1] |
| B70 | 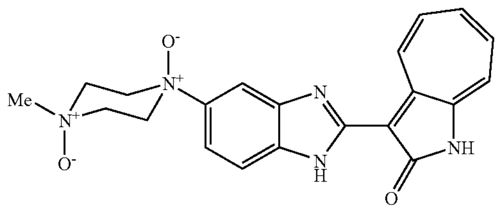 [SMILES: C[N+]1([O-])CC[N+]([O-])(c2ccc3[nH]c(-c4c5cccccc-5[nH]c4=O)nc3c2)CC1] |
| B71 | 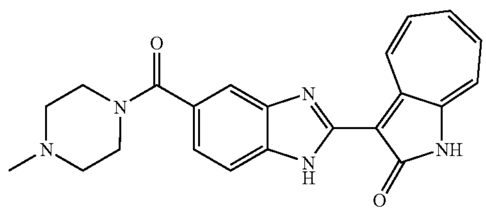 [SMILES: CN1CCN(C(=O)c2ccc3[nH]c(-c4c5cccccc-5[nH]c4=O)nc3c2)CC1] |
| B72 | 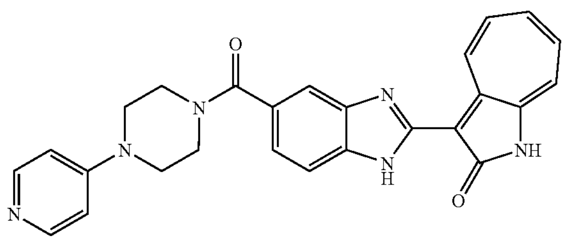 [SMILES: O=C(c1ccc2[nH]c(-c3c4cccccc-4[nH]c3=O)nc2c1)N1CCN(c2ccncc2)CC1] |
| B73 | 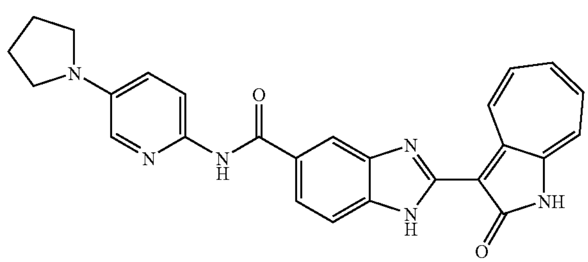 [SMILES: O=C(Nc1ccc(N2CCCC2)cn1)c1ccc2[nH]c(-c3c4cccccc-4[nH]c3=O)nc2c1] |

TABLE 1-continued

Certain exemplary compounds.

| Compound No. | Structure |
|---|---|
| B74 | 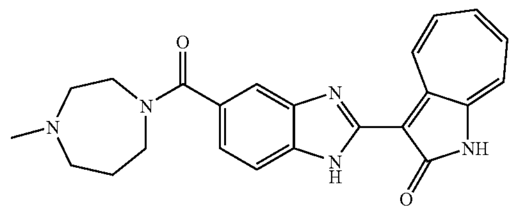 [SMILES: CN1CCCN(C(=O)c2ccc3[nH]c(-c4c5cccccc-5[nH]c4=O)nc3c2)CC1] |
| B75 | 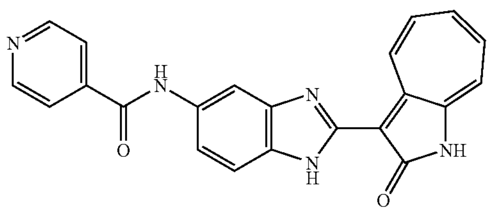 [SMILES: O=C(Nc1ccc2[nH]c(-c3c4cccccc-4[nH]c3=O)nc2c1)c1ccncc1] |
| B76 | 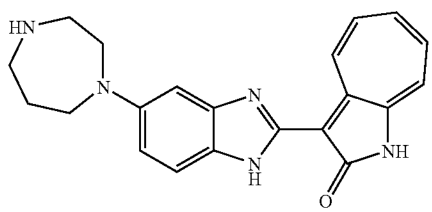 [SMILES: O=c1[nH]c2cccccc-2c1-c1nc2cc(N3CCCNCC3)ccc2[nH]1] |
| B77 | 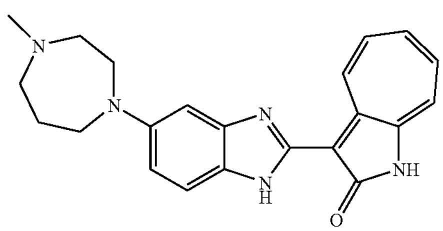 [SMILES: CN1CCCN(c2ccc3[nH]c(-c4c5cccccc-5[nH]c4=O)nc3c2)CC1] |
| B78 | 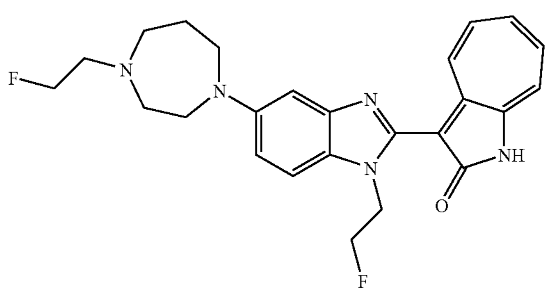 [SMILES: O=c1[nH]c2cccccc-2c1-c1nc2cc(N3CCCN(CCF)CC3)ccc2n1CCF] |
| B79 | 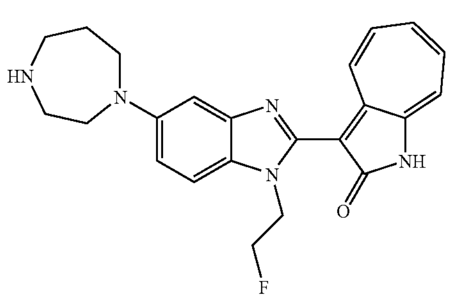 [SMILES: O=c1[nH]c2cccccc-2c1-c1nc2cc(N3CCCNCC3)ccc2n1CCF] |

TABLE 1-continued

Certain exemplary compounds.

| Compound No. | Structure |
|---|---|
| B80 | 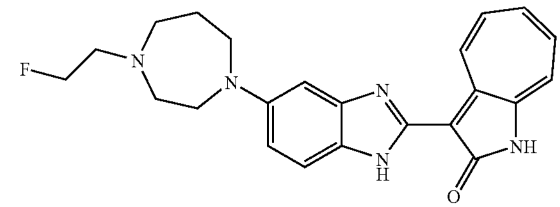 [SMILES: O=c1[nH]c2cccccc-2c1-c1nc2cc(N3CCCN(CCF)CC3)ccc2[nH]1] |
| B81 | 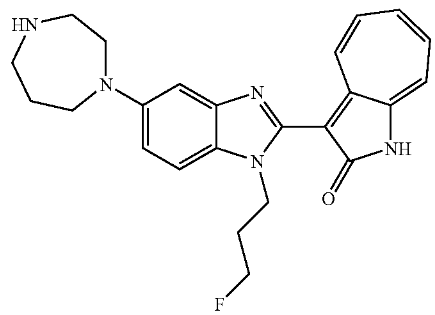 [SMILES: O=c1[nH]c2cccccc-2c1-c1nc2cc(N3CCCNCC3)ccc2n1CCCF] |
| B82 | 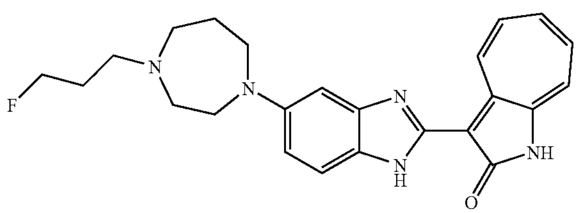 [SMILES: O=c1[nH]c2cccccc-2c1-c1nc2cc(N3CCCN(CCCF)CC3)ccc2[nH]1] |
| B83 | 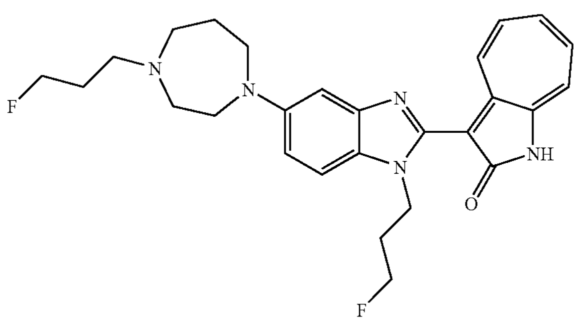 [SMILES: O=c1[nH]c2cccccc-2c1-c1nc2cc(N3CCCN(CCCF)CC3)ccc2n1CCCF] |
| B84 | 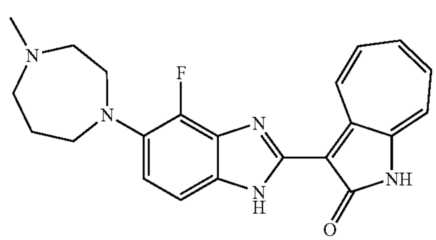 [SMILES: CN1CCCN(c2ccc3[nH]c(-c4c5cccccc-5[nH]c4=O)nc3c2F)CC1] |
| B85 | 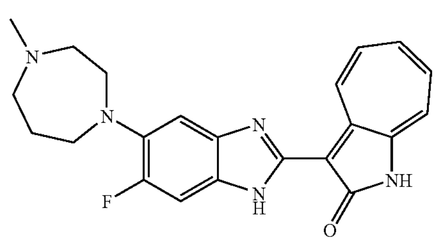 [SMILES: CN1CCCN(c2cc3nc(-c4c5cccccc-5[nH]c4=O)[nH]c3cc2F)CC1] |

TABLE 1-continued

Certain exemplary compounds.

| Compound No. | Structure |
|---|---|
| B86 | 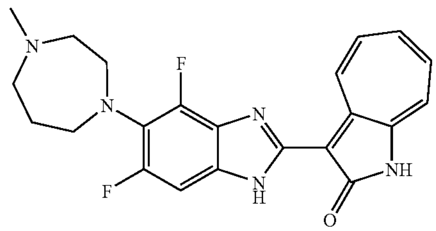 |
| B87 | 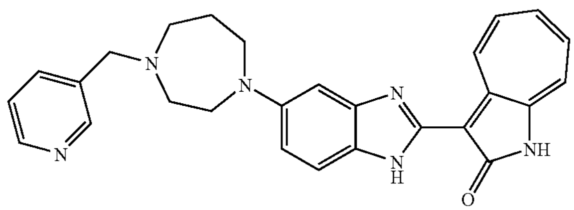 [SMILES: O=c1[nH]c2cccccc-2c1-c1nc2cc(N3CCCN(Cc4cccnc4)CC3)ccc2[nH]1] |
| B88 | 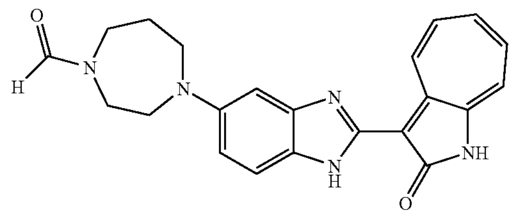 [SMILES: O=CN1CCCN(c2ccc3[nH]c(-c4c5cccccc-5[nH]c4=O)nc3c2)CC1] |
| B89 | 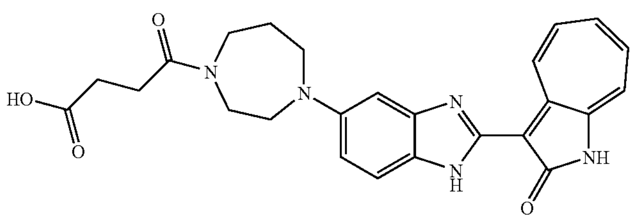 [SMILES: O=C(O)CCC(=O)N1CCCN(c2ccc3[nH]c(-c4c5cccccc-5[nH]c4=O)nc3c2)CC1] |
| B90 | 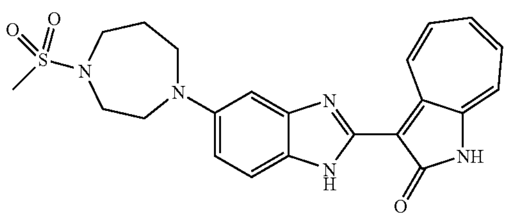 [SMILES: CS(=O)(=O)N1CCCN(c2ccc3[nH]c(-c4c5cccccc-5[nH]c4=O)nc3c2)CC1] |
| B91 | 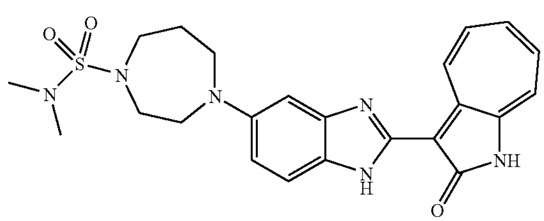 [SMILES: CN(C)S(=O)(=O)N1CCCN(c2ccc3[nH]c(-c4c5cccccc-5[nH]c4=O)nc3c2)CC1] |
| B92 | 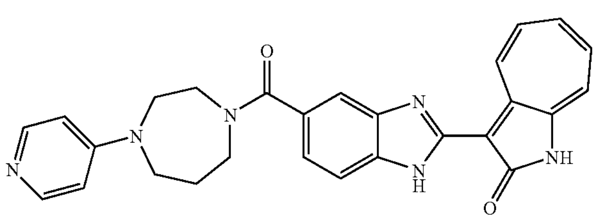 [SMILES: O=C(c1ccc2[nH]c(-c3c4cccccc-4[nH]c3=O)nc2c1)N1CCCN(c2ccncc2)CC1] |

TABLE 1-continued

Certain exemplary compounds.

| Compound No. | Structure |
| --- | --- |
| B93 | 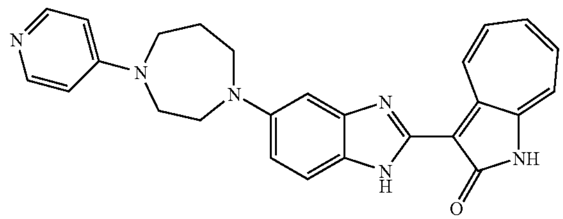 [SMILES: O=c1[nH]c2cccccc-2c1-c1nc2cc(N3CCCN(c4ccncc4)CC3)ccc2[nH]1] |
| B94 | 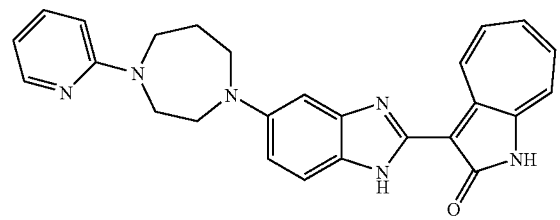 [SMILES: O=c1[nH]c2cccccc-2c1-c1nc2cc(N3CCCN(c4ccccn4)CC3)ccc2[nH]1] |
| B95 | 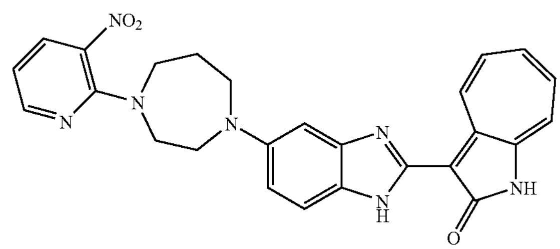 [SMILES: O=c1[nH]c2cccccc-2c1-c1nc2cc(N3CCCN(c4ncccc4[N+](=O)[O-])CC3)ccc2[nH]1] |
| B96 | 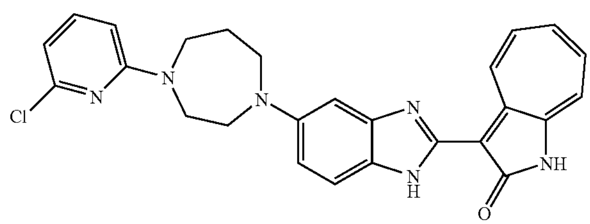 [SMILES: O=c1[nH]c2cccccc-2c1-c1nc2cc(N3CCCN(c4cccc(Cl)n4)CC3)ccc2[nH]1] |
| B97 | 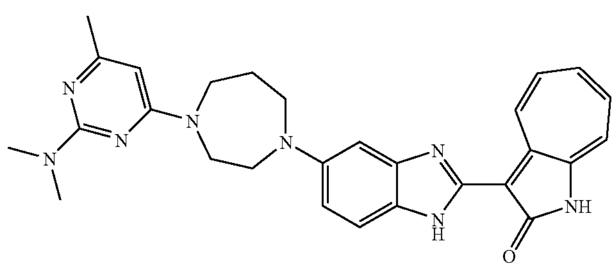 [SMILES: Cc1cc(N2CCCN(c3ccc4[nH]c(-c5c6cccccc-6[nH]c5=O)nc4c3)CC2)nc(N(C)C)n1] |
| B98 | 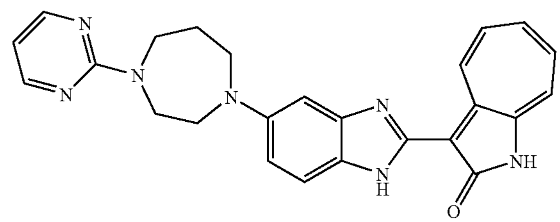 [SMILES: O=c1[nH]c2cccccc-2c1-c1nc2cc(N3CCCN(c4ncccn4)CC3)ccc2[nH]1] |

TABLE 1-continued

Certain exemplary compounds.

| Compound No. | Structure |
|---|---|
| B99 | 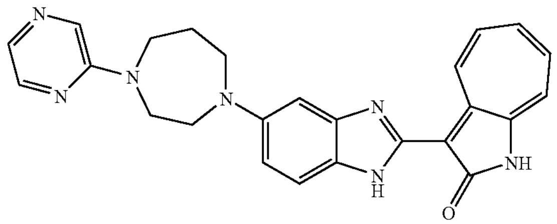 [SMILES: O=c1[nH]c2cccccc-2c1-c1nc2cc(N3CCCN(c4cnccn4)CC3)ccc2[nH]1] |
| B100 | 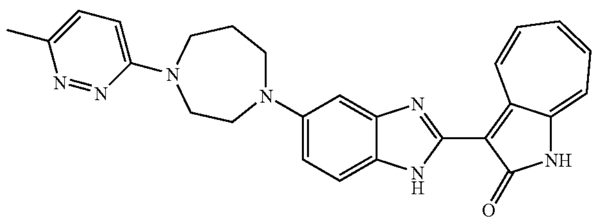 [SMILES: Cc1ccc(N2CCCN(c3ccc4[nH]c(-c5c6cccccc-6[nH]c5=O)nc4c3)CC2)nn1] |
| B101 | 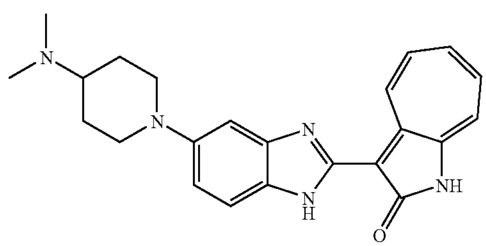 [SMILES: CN(C)C1CCN(c2ccc3[nH]c(-c4c5cccccc-5[nH]c4=O)nc3c2)CC1] |
| B102 | 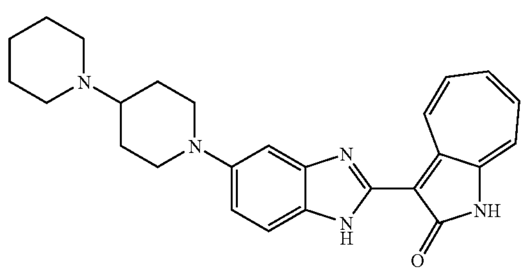 [SMILES: O=c1[nH]c2cccccc-2c1-c1nc2cc(N3CCC(N4CCCCC4)CC3)ccc2[nH]1] |
| B103 | 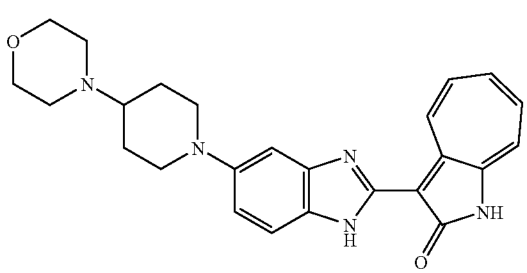 [SMILES: O=c1[nH]c2cccccc-2c1-c1nc2cc(N3CCC(N4CCOCC4)CC3)ccc2[nH]1] |
| B104 | 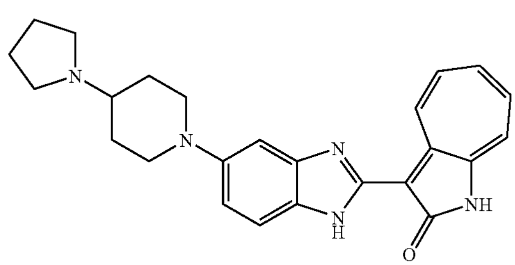 [SMILES: O=c1[nH]c2cccccc-2c1-c1nc2cc(N3CCC(N4CCCC4)CC3)ccc2[nH]1] |

TABLE 1-continued

Certain exemplary compounds.

| Compound No. | Structure |
|---|---|
| B105 | 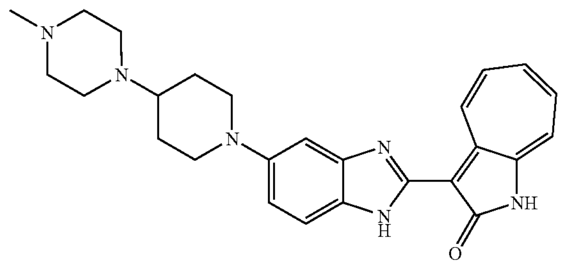 [SMILES: CN1CCN(C2CCN(c3ccc4[nH]c(-c5c6cccccc-6[nH]c5=O)nc4c3)CC2)CC1] |
| B106 | 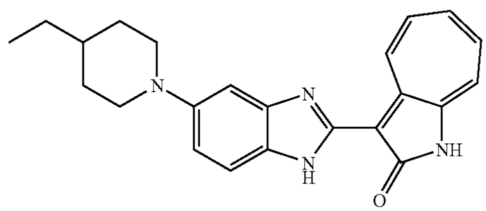 [SMILES: CCC1CCN(c2ccc3[nH]c(-c4c5cccccc-5[nH]c4=O)nc3c2)CC1] |
| B107 | 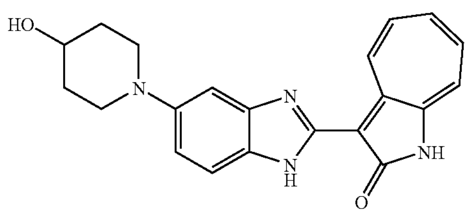 [SMILES: O=c1[nH]c2cccccc-2c1-c1nc2cc(N3CCC(O)CC3)ccc2[nH]1] |
| B108 | 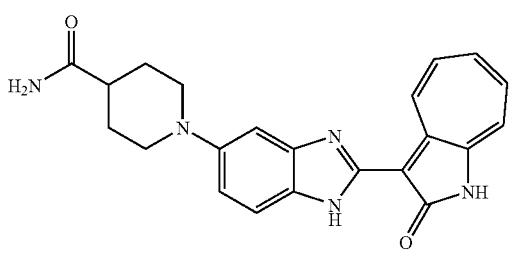 [SMILES: NC(=O)C1CCN(c2ccc3[nH]c(-c4c5cccccc-5[nH]c4=O)nc3c2)CC1] |
| B109 | 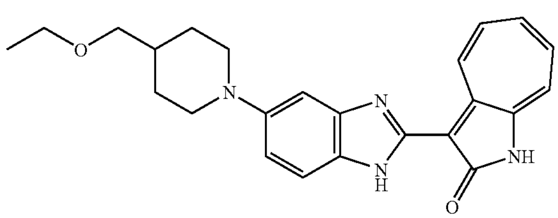 [SMILES: CCOCC1CCN(c2ccc3[nH]c(-c4c5cccccc-5[nH]c4=O)nc3c2)CC1] |
| B110 | 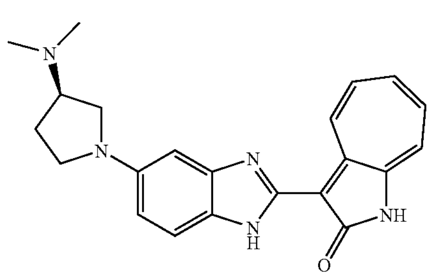 [SMILES: CN(C)[C@@H]1CCN(c2ccc3[nH]c(-c4c5cccccc-5[nH]c4=O)nc3c2)C1] |

TABLE 1-continued

Certain exemplary compounds.

| Compound No. | Structure |
|---|---|
| B111 | 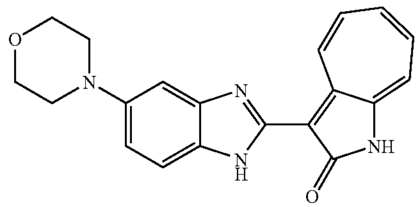 [SMILES: O=c1[nH]c2cccccc-2c1-c1nc2cc(N3CCOCC3)ccc2[nH]1] |
| B112 | 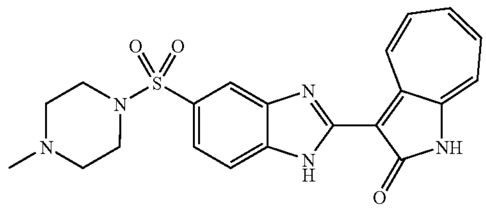 [SMILES: CN1CCN(S(=O)(=O)c2ccc3[nH]c(-c4c5cccccc-5[nH]c4=O)nc3c2)CC1] |
| B113 | 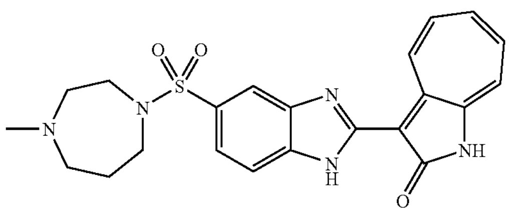 [SMILES: CN1CCCN(S(=O)(=O)c2ccc3[nH]c(-c4c5cccccc-5[nH]c4=O)nc3c2)CC1] |
| B114 | 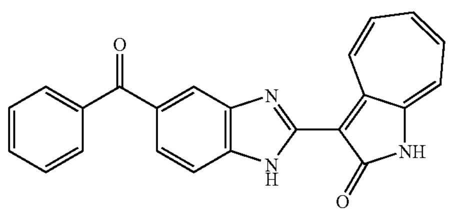 [SMILES: O=C(c1ccccc1)c1ccc2[nH]c(-c3c4cccccc-4[nH]c3=O)nc2c1] |
| B115 | 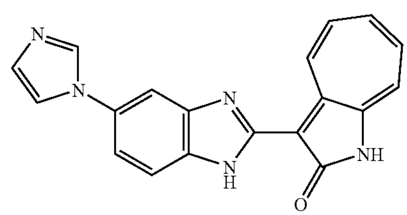 [SMILES: O=c1[nH]c2cccccc-2c1-c1nc2cc(-n3ccnc3)ccc2[nH]1] |
| B116 | 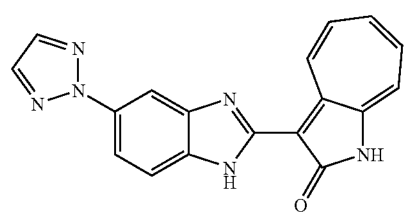 [SMILES: O=c1[nH]c2cccccc-2c1-c1nc2cc(-n3nccn3)ccc2[nH]1] |
| B117 | 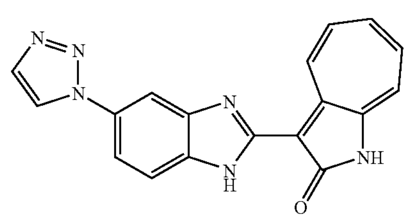 [SMILES: O=c1[nH]c2cccccc-2c1-c1nc2cc(-n3ccnn3)ccc2[nH]1] |

TABLE 1-continued

Certain exemplary compounds.

| Compound No. | Structure |
|---|---|
| B118 | 3-trifluoromethyl-4-chlorophenyl urea linked to 5-aminobenzimidazole-2-yl-(2-oxoindol-3-yl) |
| B119 | 2-fluoro-5-trifluoromethylphenyl urea linked to 5-aminobenzimidazole-2-yl-(2-oxoindol-3-yl) |
| B120 | 2,5-difluorophenyl urea linked to 5-aminobenzimidazole-2-yl-(2-oxoindol-3-yl) |
| B121 | phenyl urea linked to 5-aminobenzimidazole-2-yl-(2-oxoindol-3-yl) |
| B122 | 3,5-dichloropyridin-4-yl urea linked to 5-aminobenzimidazole-2-yl-(2-oxoindol-3-yl) |
| B123 | 2-ethyl-6-methylphenyl urea linked to 5-aminobenzimidazole-2-yl-(2-oxoindol-3-yl) |
| B124 | cyclohexyl urea linked to 5-aminobenzimidazole-2-yl-(2-oxoindol-3-yl) |

TABLE 1-continued
Certain exemplary compounds.
| Compound No. | Structure |
|---|---|
| B125 | 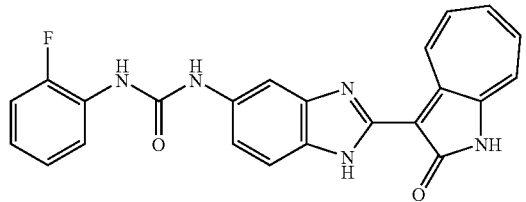 |
| B126 | 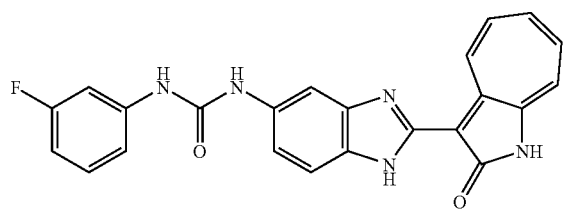 [SMILES: O=C(Nc1cccc(F)c1)Nc1ccc2[nH]c(-c3c4cccccc-4[nH]c3=O)nc2c1] |
| B127 | 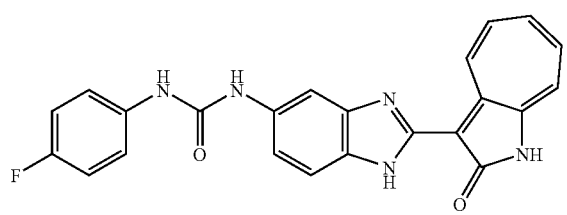 [SMILES: O=C(Nc1ccc(F)cc1)Nc1ccc2[nH]c(-c3c4cccccc-4[nH]c3=O)nc2c1] |
| B128 | 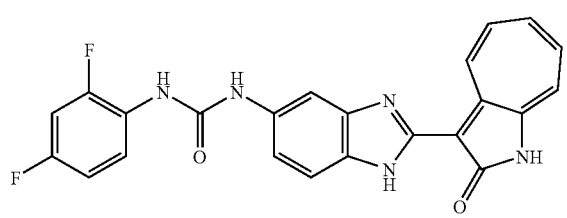 [SMILES: O=C(Nc1ccc2[nH]c(-c3c4cccccc-4[nH]c3=O)nc2c1)Nc1ccc(F)cc1F] |
| B129 | 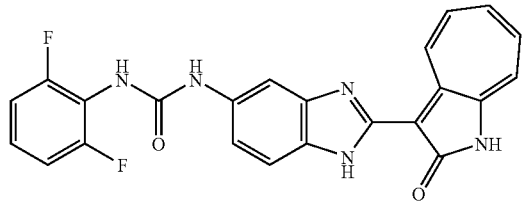 [SMILES: O=C(Nc1ccc2[nH]c(-c3c4cccccc-4[nH]c3=O)nc2c1)Nc1c(F)cccc1F] |
| B130 | 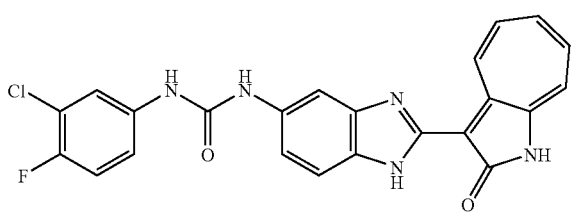 [SMILES: O=C(Nc1ccc(F)c(Cl)c1)Nc1ccc2[nH]c(-c3c4cccccc-4[nH]c3=O)nc2c1] |
| B131 | 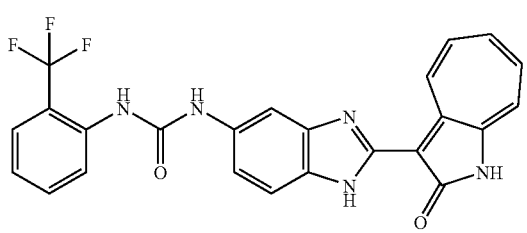 [SMILES: O=C(Nc1ccc2[nH]c(-c3c4cccccc-4[nH]c3=O)nc2c1)Nc1ccccc1C(F)(F)F] |

TABLE 1-continued

Certain exemplary compounds.

| Compound No. | Structure |
| --- | --- |
| B132 | 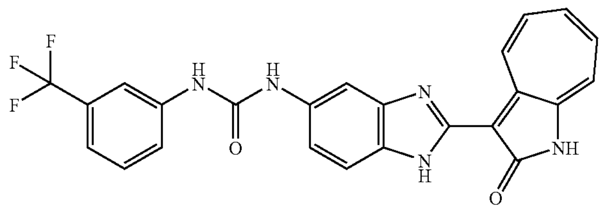 [SMILES: O=C(Nc1cccc(C(F)(F)F)c1)Nc1ccc2[nH]c(-c3c4cccccc-4[nH]c3=O)nc2c1] |
| B133 | 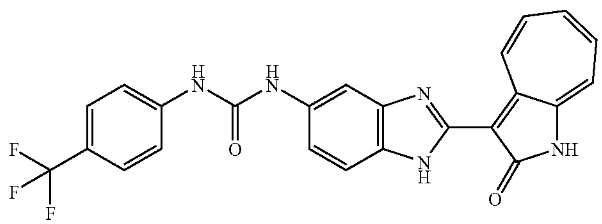 [SMILES: O=C(Nc1ccc(C(F)(F)F)cc1)Nc1ccc2[nH]c(-c3c4cccccc-4[nH]c3=O)nc2c1] |
| B134 | 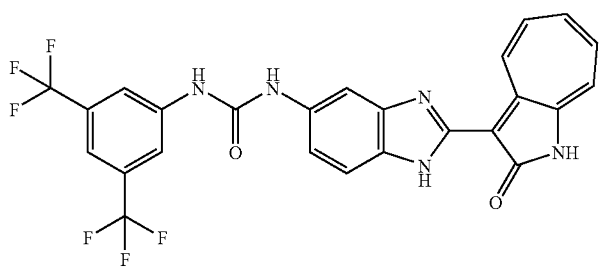 [SMILES: O=C(Nc1cc(C(F)(F)F)cc(C(F)(F)F)c1)Nc1ccc2[nH]c(-c3c4cccccc-4[nH]c3=O)nc2c1] |
| B135 | 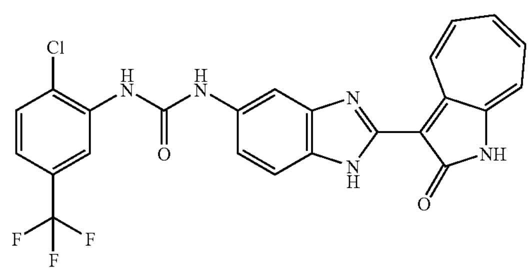 [SMILES: O=C(Nc1ccc2[nH]c(-c3c4cccccc-4[nH]c3=O)nc2c1)Nc1cc(C(F)(F)F)ccc1Cl] |
| B136 | 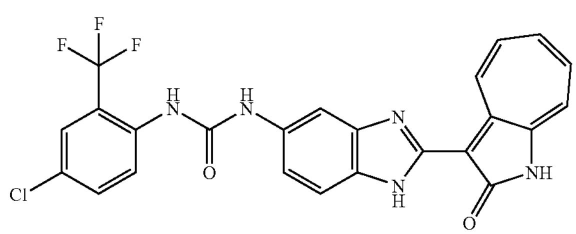 [SMILES: O=C(Nc1ccc2[nH]c(-c3c4cccccc-4[nH]c3=O)nc2c1)Nc1ccc(Cl)cc1C(F)(F)F] |
| B137 | 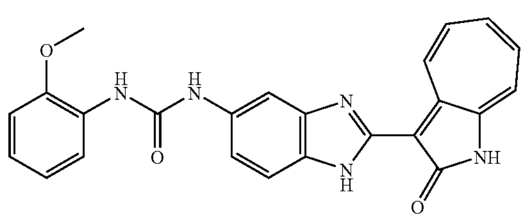 |

TABLE 1-continued

Certain exemplary compounds.

| Compound No. | Structure |
|---|---|
| B138 | 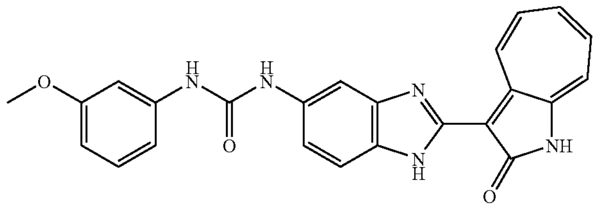 [SMILES: COc1cccc(NC(=O)Nc2ccc3[nH]c(-c4c5cccccc-5[nH]c4=O)nc3c2)c1] |
| B139 | 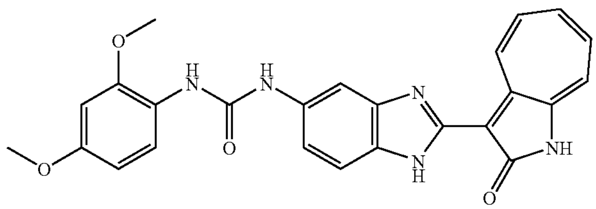 [SMILES: COc1ccc(NC(=O)Nc2ccc3[nH]c(-c4c5cccccc-5[nH]c4=O)nc3c2)c(OC)c1] |
| B140 | 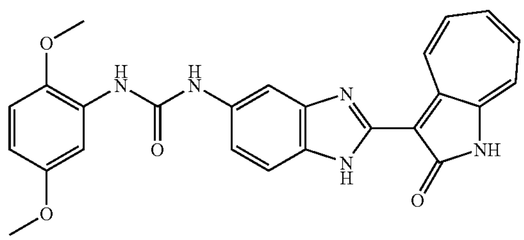 [SMILES: COc1ccc(OC)c(NC(=O)Nc2ccc3[nH]c(-c4c5cccccc-5[nH]c4=O)nc3c2)c1] |
| B141 | 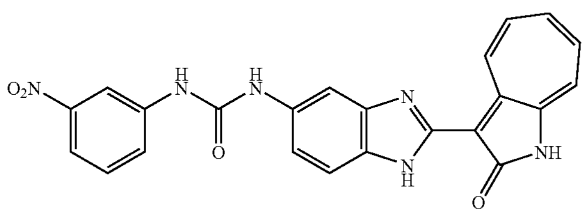 [SMILES: O=C(Nc1cccc([N+](=O)[O-])c1)Nc1ccc2[nH]c(-c3c4cccccc-4[nH]c3=O)nc2c1] |
| B142 | 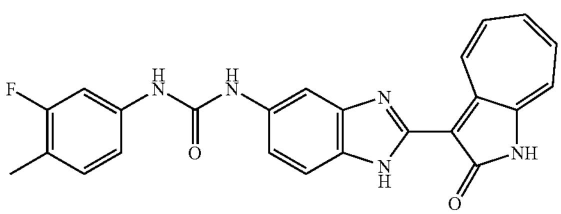 [SMILES: Cc1ccc(NC(=O)Nc2ccc3[nH]c(-c4c5cccccc-5[nH]c4=O)nc3c2)cc1F] |
| B143 | 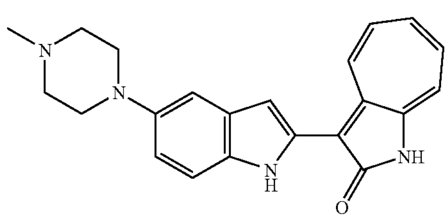 [SMILES: CN1CCN(c2ccc3[nH]c(-c4c5cccccc-5[nH]c4=O)cc3c2)CC1] |

EXAMPLES

Comparative Example (Compound A1)

Preparation of 3-(benzimidazol-2-yl)-1-azaazulen-2-one (A1): 3-Formyl-1-azaazulen-2-one (0.1 mmol) was dissolved in a mixture of 10 mL ethanol and 5 mL water. o-Phenylenediamine (0.15 mmol) and sodium bisulfite (0.2 mmol) were then added and heat to reflux for 1 day. After working up, the residue was then purified by column chromatography to give 8.6 mg of A1, yield 95%.

$^1$H-NMR (500 MHz, DMSO-d6) δ (ppm) 12.28 (s, 1H), 9.41 (d, 1H), 7.70-7.68 (m, 2H), 7.63 (t, 1H), 7.55 (t, 1H), 7.45 (d, 1H), 7.32 (t, 1H), 7.20-7.18 (m, 2H). LC-MS (m/z) 262 [M+1].

Example 1

General procedure for the condensation of 3-formyl-1-azaazulen-2-ones with substituted o-phenylenediamines. 3-Formyl-1-azaazulen-2-one (0.1 mmol) was dissolved in a mixture of 10 mL ethanol and 5 mL water. Substituted o-phenylenediamine (0.15 mmol) and sodium bisulfite (0.2 mmol) were then added and heat to reflux for 1 day. After working up, the residue was purified by column chromatography to give the target compound.

B1, $^1$H-NMR (500 MHz, CDCl$_3$) δ (ppm) 11.53 (s, 1H), 9.56 (d, 1H), 7.81 (d, 1H), 7.53-7.149 (m, 7H), 4.26 (t, 2H), 2.78 (t, 2H), 2.62 (q, 4H), 1.02 (t, 6H). LC-MS (m/z) 361 [M+1].

B2, $^1$H-NMR (500 MHz, DMSO-d6) δ (ppm) 12.31 (s, 1H), 9.36 (d, 1H), 7.68 (t, 1H), 7.65 (t, 1H), 7.57 (t, 1H), 7.48-7.45 (m, 2H), 7.34 (t, 1H), 7.04 (dt, 1H). LC-MS (m/z) 280 [M+1].

B4, $^1$H-NMR (500 MHz, DMSO-d6) δ (ppm) 12.58 (s, 1H), 12.39 & 12.37 (s, 1H), 9.44 & 9.42 (d, 1H), 8.07 & 8.01 (s, 1H), 7.87 & 7.86 (t, 1H), 7.73 & 7.14 (t, 1H), 7.63 & 7.62 (t, 1H), 7.54-7.49 (m, 2H), 7.41 & 7.39 (t, 1H). LC-MS (m/z) 330 [M+1].

B5, $^1$H-NMR (500 MHz, DMSO-d6) δ (ppm) 12.55 (s, 1H), 9.38 (d, 1H), 8.64 (s, 1H), 8.58 (s, 1H), 8.15 (d, 1H), 7.85 (d, 1H), 7.80 (t, 1H), 7.71 (t, 1H), 7.63 (d, 1H), 7.48 (t, 1H).

B6, $^1$H-NMR (500 MHz, DMSO-d6) δ (ppm) 12.74 (s, 1H), 9.11 (d, 1H), 7.73-7.81 (m, 5H), 7.56 (t, 3H), 7.27 (s, 2H).

B7, $^1$H-NMR (500 MHz, DMSO-d6) δ (ppm) 12.39 (s, 1H), 8.31 (s, 1H), 7.84 (d, 1H), 7.63 (t, 1H), 7.53 (d, 1H), 7.40 (t, 1H), 7.36 (t, 2H), 3.97 (d, 1H), 3.40 (s, 1H).

B8, $^1$H-NMR (500 MHz, DMSO-d6) δ (ppm) 12.18 (s, 1H), 11.90, 11.95 (s, 1H), 9.30, 9.35 (d, 1H), 8.95, 9.12 (s, 1H), 7.44-7.60 (m, 3H), 7.36, 7.39 (d, 1H), 7.22-7.29 (m, 1H), 7.00, 7.07 (d, 1H), 6.69 (dt, 1H).

B15, $^1$H-NMR (500 MHz, DMSO-d6) δ (ppm) 12.37 (s, 1H), 9.44 (broad, 1H), 8.36 (s, 1H), 8.02 (d, J=7.0 Hz, 1H), 7.73 (t, J=10 Hz, 1H), 7.63 (t, J=10.0 Hz, 1H), 7.54 (d, J=9.0 Hz, 1H), 7.41 (t, J=9.5 Hz, 1H), 7.22 (broad, 1H). LC-MS (m/z) 263 [M+1].

B18, $^1$H-NMR (500 MHz, DMSO-d6) δ (ppm) 12.38 (s, 1H), 12.19 (s, 2H), 9.30 (d, 2H), 8.16 (s, 1H), 8.09 (s, 1H), 7.98 (d, 1H), 7.93 (d, 1H), 7.73 (t, 1H), 7.61 (t, 1H), 7.53 (d, 1H), 7.32-7.40 (m, 3H).

B19, $^1$H-NMR (500 MHz, DMSO-d6) δ (ppm) 12.59 (d, 1H), 12.36 (d, 1H), 9.35-9.40 (m, 1H), 8.07, 8.13 (s, 1H), 7.38-7.83 (m, 6H).

B20, $^1$H-NMR (500 MHz, DMSO-d6) δ (ppm) 12.16, 12.19 (s, 1H), 12.02 (s, 1H), 9.30, 9.35 (d, 1H), 9.16, 9.24 (s, 1H), 7.75, 7.89 (s, 1H), 7.45-7.60 (m, 3H), 7.37 (t, 1H), 7.16-7.29 (m, 2H), 1.50 (s, 9H).

B22, $^1$H-NMR (500 MHz, DMSO-d6) δ (ppm) 12.28 (s, 1H), 12.00, 12.05 (s, 1H), 9.32, 9.37 (d, 1H), 7.41-7.60 (m, 4H), 7.27 (m, 2H), 6.99 (d, 1H), 3.28-3.35 (m, 8H).

B24, $^1$H-NMR (500 MHz, DMSO-d6) δ (ppm) 11.10 (d, 1H), 9.40 (m, 1H), 7.73 (d, 1H), 7.44 (m, 3H), 7.16 (m, 1H), 7.04 (m 3H), 3.60 (d, 2H), 3.20 (b, 1H), 2.41 (q, 2H), 1.24 (d, 6H).

B26, $^1$H-NMR (500 MHz, DMSO-d6) δ (ppm) 12.20 (s, 1H), 11.97 & 11.91 (s, 1H), 9.38 & 9.31 (d, 1H), 7.58-6.94 (m, 7H), 3.34 (s, 4H), 3.14 (s, 4H), 2.24 (s, 3H). LC-MS (m/z) 360 [M+1].

B27, $^1$H-NMR (500 MHz, DMSO-d6) δ (ppm) 12.21 (s, 1H) 9.37 (d, 1H), 7.82 (d, 1H), 7.53-7.60 (m, 1H), 7.53 (m, 1H), 7.43 (d, 1H), 7.27-7.34 (m, 1H), 6.78 (t, 1H), 3.54 (m, 4H), 2.47 (m, 4H), 2.26 (s, 3H).

B32, $^1$H-NMR (DMSO-d6, 500 MHz) δ 1.61 (m, 2H), 11.34, 11.39 (s, 1H), 9.47, 9.51 (d, 1H), 7.45 (dd, 1H), 7.25-7.35, 7.67 (m, 3H), 7.18 (dd, 1H), 6.97-6.98 (m, 1H), 3.23 (s, 4H), 2.62 (s, 4H), 2.52-2.62 (m, 6H), 1.80 (m, 2H).

B33, $^1$H-NMR (500 MHz, DMSO-d6) δ (ppm) 12.82 (s, 1H), 11.47 (s, 1H), 10.80 (s, 1H), 8.94 (d, 1H), 7.74-7.84 (m, 3H), 7.58 (t, 1H), 7.32 (s, 1H), 7.28 (d, 1H), 3.85 (d, 2H), 3.67 (d, 2H), 2.80 (s, 6H), 2.27 (dd, 2H), 2.11 (s, 2H).

B34, $^1$H-NMR (500 MHz, DMSO-d6) δ (ppm) 8.85 (d, 1H), 7.31 (d, 1H), 7.21 (t, 1H), 7.08 (m, 1H), 7.04 (m, 4H), 6.94 (m, 1H), 6.75 (d, 1H), 3.50 (t, 4H), 2.97 (d, 4H), 2.46 (s, 2H), 2.34 (m, 2H), 2.27 (m, 4H), 1.41 (m, 4H), 0.76 (m, 6H).

B35, $^1$H-NMR (500 MHz, DMSO-d6) δ (ppm) 11.19 (d, 1H), 9.93 (m, 1H), 7.56 (m, 3H), 7.36 (t, 1H), 7.24 (q, 1H), 7.15 (d, 1H), 6.91 (t, 1H), 3.25 (m, 2H), 3.17 (s, 4H), 2.80 (d, 2H), 2.65 (s, 4H), 2.14 (s, 3H), 1.98 (m, 1H), 1.77 (d, 2H), 1.47 (q, 2H).

B36, $^1$H-NMR (500 MHz, DMSO-d6) δ (ppm) 9.20 (d, 1H), 7.62 (m, 2H), 7.56 (m, 1H), 7.38 (m, 4H), 7.17 (m, 1H), 7.10 (d, 1H), 3.80 (m, 2H), 3.69 (m, 4H), 2.83 (m, 4H), 2.68 (m, 2H), 2.07 (s, 1H).

B50, $^1$H-NMR (500 MHz, DMSO-d6) δ (ppm) 12.23 (s, 1H), 12.10, 12.12 (s, 1H), 9.31, 9.34 (d, 1H), 7.59 (t, 1H), 7.51 (t, 1H), 7.38-7.44 (m, 2H), 7.27-7.33 (m, 1H), 3.03 (s, 4H), 2.53 (s, 4H), 2.27 (s, 3H).

B51, $^1$H-NMR (500 MHz, DMSO-d6) δ (ppm) 12.26 (s, 1H), 12.19 (s, 1H), 9.35 (d, 1H), 7.64 (t, 1H), 7.53 (t, 1H), 7.44 (d, 1H), 7.38 (d, 1H), 7.31 (t, 1H), 6.96 (t, 1H), 3.03 (s, 4H), 2.53 (s, 4H), 2.26 (s, 3H).

B52, $^1$H-NMR (500 MHz, DMSO-d6) δ (ppm) 12.38 (s, 1H), 9.30 (d, 1H), 7.67 (t, 1H), 7.57 (t, 1H), 7.48 (d, 1H), 7.29-7.36 (m, 2H), 3.54 (s, 3H), 3.16 (s, 2H), 2.48 (s, 2H), 2.27 (s, 2H), 1.26 (s, 2H).

B60, $^1$H-NMR (500 MHz, DMSO-d6+TFA-d) δ (ppm) 13.50 (s, 1H), 12.81 (s, 1H), 8.57 (d, 1H), 8.32 (d, 2H), 7.88 (m, 1H), 7.77 & 7.73 (d, 1H), 7.63 (t, 1H), 7.33 (t, 1H), 7.30 (d, 2H), 3.96 (s, 4H), 3.46 (s, 4H). LC-MS (m/z) 422 [M+1].

B75, $^1$H-NMR (500 MHz, DMSO-d6) δ (ppm) 12.25 (s, 1H), 12.21, 12.24 (s, 1H), 10.50, 10.56 (s, 1H), 9.39 (t, 1H), 8.81 (s, 2H), 7.93 (s, 2H), 7.29-7.66 (m, 6H).

B76, $^1$H-NMR (500 MHz, DMSO-d6) δ (ppm) 11.67, 11.79 (s, 1H), 9.24, 9.34 (d, 1H), 7.39-7.50 (m, 3H), 7.31 (t, 1H), 7.19 (t, 1H), 6.89, 6.95 (s, 1H), 6.70 (d, 1H), 3.50-3.57 (m, 5H), 2.91 (s, 2H), 2.65 (s, 2H), 1.84 (s, 2H).

B77, $^1$H-NMR (500 MHz, DMSO-d6) δ (ppm) 12.13 (s, 1H), 11.69, 11.81 (s, 1H), 9.25, 9.35 (d, 1H), 7.17-7.53 (m, 5H), 6.89, 6.94 (s, 1H), 6.69 (d, 1H), 3.47-4.07 (m, 6H), 3.17 (s, 2H), 2.27 (s, 3H), 1.93 (d, 2H).

B85, $^1$H-NMR (500 MHz, DMSO-d6) δ (ppm) 12.18 (s, 1H), 11.96, 12.02 (s, 1H), 9.26, 9.30 (d, 1H), 7.51-7.57 (m, 2H), 7.44-7.49 (m, 2H), 7.33-7.38 (m, 2H), 7.21-7.30 (m, 2H), 2.72 (s, 2H), 2.63 (s, 2H), 2.32 (s, 2H), 1.94 (s, 2H), 1.25 (s, 2H).

B86, $^1$H-NMR (500 MHz, DMSO-d6) δ (ppm) 12.32 (s, 1H), 9.29 (d, 1H), 7.64 (t, 1H), 7.54 (t, 1H), 7.44 (d, 1H), 7.32 (t, 1H), 7.27 (d, 1H), 3.28 (s, 3H), 2.68 (t, 2H), 2.64 (t, 2H), 2.33 (s, 4H), 1.87-1.91 (m, 2H).

B101, $^1$H-NMR (500 MHz, DMSO-d6) δ (ppm) 11.90 (d, 1H), 9.30 (m, 1H), 7.55 (m, 3H), 7.46 (t, 1H), 7.25 (m, 3H), 6.93 (m 1H), 3.67 (d, 2H), 2.68 (m, 2H), 2.29 (s, 6H), 1.90 (d, 2H), 1.58 (m, 2H).

B102, $^1$H-NMR (500 MHz, DMSO-d6) δ (ppm) 12.20 (b, 1H), 11.90 (d, 1H), 8.30 (s, 1H), 9.30 (m, 1H), 7.54 (m, 3H), 7.40 (s 1H), 7.38 (m, 2H), 7.20 (m, 1H), 3.73 (d, 2H), 2.82 (m, 2H), 2.03 (m, 2H), 1.70 (m, 2H), 1.21 (m, 2H).

B103, $^1$H-NMR (500 MHz, DMSO-d6) δ (ppm) 11.90 (d, 1H), 9.28 (m, 1H), 7.50 (m, 3H), 7.35 (t, 1H), 7.19 (m, 3H), 6.91 (t 1H), 3.63 (d, 2H), 3.58 (s, 1H), 2.66 (m, 2H), 2.26 (s, 6H), 1.88 (d, 2H), 1.55 (b, 2H).

B104, $^1$H-NMR (500 MHz, DMSO-d6) δ (ppm) 11.0 (d, 1H), 9.46 (m, 1H), 7.6 (d, 1H), 7.49 (m, 2H), 7.2-7.51 (m, 3H), 7.01 (b, 2H), 3.69 (m, 4H), 2.79 (q, 1H), 2.71 (b, 4H), 2.05 (b, 2H), 1.84 (b, 4H), 1.25 (s, 2H).

B105, $^1$H-NMR (500 MHz, DMSO-d6) δ (ppm) 11.96 (d, 1H), 9.37 (m, 1H), 7.56 (m, 3H), 7.40 (t, 1H), 7.29 (m, 3H), 6.92 (m, 1H), 3.67 (m, 1H), 3.3 (s, 4H), 3.12 (m, 2H), 2.69 (m, 2H), 2.53 (s, 4H), 2.17 (s, 3H), 1.92 (m, 2H), 1.62 (m, 2H).

B106, $^1$H-NMR (500 MHz, DMSO-d6) δ (ppm) 9.16 (d, 1H), 7.59 (t, 1H), 7.48 (t, 1H), 7.35 (m, 5H), 7.251 (1H,$), 7.08 (d, 1H), 3.37 (s, 2H), 3.29 (t, 1H), 2.75 (d, 4H), 2.58 (m, 4H), 1.22 (t, 3H).

B107, $^1$H-NMR (500 MHz, DMSO-d6) δ (ppm) 12.19 (b, 1H), 11.88 (d, 1H), 9.28 (m, 1H), 9.31 (m, 1H), 7.55 (m, 3H), 7.41 (t, 1H), 7.21 (m, 3H), 6.85 (t, 1H), 3.66 (m, 1H), 3.53 (b, 2H), 2.85 (q, 2H), 1.89 (b, 2H), 1.58 (m, 2H).

B108, $^1$H-NMR (500 MHz, DMSO-d6) δ (ppm) 9.18 (d, 1H), 7.60 (m, 2H), 7.52 (t, 1H), 7.37 (m, 4H), 7.27 (t, 1H), 7.10 (d, 1H), 3.74 (d, 2H), 2.41 (t, 1H), 2.30 (m, 4H), 1.94 (m, 4H).

B109, $^1$H-NMR (500 MHz, DMSO-d6) δ (ppm) 9.05 (d, 1H), 7.51 (m, 2H), 7.37 (m, 1H), 7.24 (m, 4H), 7.07 (m, 1H), 6.98 (t, 1H), 3.61 (d, 2H), 3.5 (m, 2H), 2.70 (t, 4H), 1.87 (d, 4H), 1.46 (m, 1H), 1.23 (m, 3H).

B110, $^1$H-NMR (500 MHz, DMSO-d6) δ (ppm) 12.1 (b, 1H), 11.77 (m, 1H), 9.32 (m, 1H), 7.42-7.50 (m, 3H), 7.34 (t, 1H), 7.22 (t, 1H), 6.79 (s, 1H), 6.59 (m, 1H), 3.48 (m, 2H), 3.20 (m, 1H), 3.11 (m, 1H), 2.88 (m, 2H), 2.25 (s, 6H), 2.21 (m, 1H), 1.87 (m, 1H).

B111, $^1$H-NMR (500 MHz, DMSO-d6) δ (ppm) 9.30 (d, 1H), 7.56 (m, 2H), 7.38 (d, 1H), 7.26 (m, 4H), 7.17 (s, 1H), 6.95 (d, 1H), 3.04 (s, 4H), 1.98 (s, 4H).

B112, $^1$H-NMR (500 MHz, DMSO-d6) δ (ppm) 12.58, 12.62 (s, 1H), 12.34 (s, 1H), 9.39, 9.41 (d, 1H), 7.97, 8.11 (s, 1H), 7.83, 7.87 (d, 1H), 7.70 (dd, 1H), 7.58-7.63 (dt, 1H), 7.49-7.53 (m, 2H), 7.36-7.40 (dt, 1H), 2.90 (s, 4H), 2.36 (d, 4H), 2.12 (d, 3H).

B113, $^1$H-NMR (500 MHz, DMSO-d6) δ (ppm) 12.54, 12.58 (s, 1H), 12.33 (s, 1H), 9.38, 9.40 (d, 1H), 8.00, 8.14 (s, 1H), 7.80, 7.84 (d, 1H), 7.69 (dd, 2H), 7.56-7.62 (m, 2H), 7.49-7.54 (m, 1H), 7.35-7.39 (m, 1H), 3.32 (s, 3H), 2.55 (s, 2H), 2.22 (s, 3H), 1.72 (d, 2H).

B114, $^1$H-NMR (500 MHz, DMSO-d6) δ (ppm) 12.49, 12.53 (s, 1H), 12.31 (s, 1H), 9.38, 9.43 (d, 1H), 7.98, 8.17 (s, 1H), 7.75-7.82 (m, 3H), 7.63-7.72 (m, 2H), 7.55-7.61 (m, 3H), 7.49 (t, 1H), 7.35 (dd, 1H).

B115, $^1$H-NMR (500 MHz, DMSO-d6) δ (ppm) 12.30 (b, 1H), 9.38 (d, 1H), 8.6 (b, 1H), 7.90-7.88 (m, 2H), 7.79 (d, 1H), 7.66 (t 1H), 7.56 (t, 1H), 7.47 (m, 2H), 7.36 (m, 2H).

B116, $^1$H-NMR (DMSO-d6) δ (ppm) 12.00 (s, 1H), 9.18 (d, 1H), 8.69 (s, 1H), 8.05 (s, 2H), 7.56-7.66 (m, 2H), 7.45-7.48 (m, 2H), 7.34 (t, 1H), 7.25 (d, 1H), 7.16 (d, 1H).

Example 2

General procedure for the N-Alkylation of B22 and B76 by alkyl halides/alkyl tosylates. To a solution of B23 or B76 in CH$_3$CN was added 1.1 eq of diisopropylethylamine followed by 1.2 eq of alkyl halides or alkyl tosylates, the reaction mixture was stirred at reflux for 16 h. The resulting mixture was allowed to cool to room temperature, concentrated in vacuum, and then purified by silica gel column chromatography to give the compound.

B23, $^1$H NMR (500 MHz, DMSO-d6) δ (ppm) 11.9 (b, 1H), 9.27 (d, 1H), 7.56-7.50 (m, 2H), 7.46 (t, 1H), 7.39 (d, 1H), 7.25 (t, 1H), 7.17, (s, 1H), 6.93 (d, 1H), 3.16 (s, 2H), 3.13 (t, 4H), 3.00 (t, 4H).

B28, $^1$H NMR (500 MHz, DMSO-d6) δ (ppm) 12.18 (s, 1H), 11.87, 11.93 (2s, 1H), 9.28, 9.34 (2d, 1H), 7.49-7.55 (m, 2H), 7.45 (t, 1H), 7.36 (t, 1H), 7.24 (t, 1H), 7.13, 7.18 (2s, 1H), 6.92 (t, 1H), 3.11 (s, 4H), 2.54 (s, 4H), 2.39 (q, 2H), 1.04 (t, 3H).

B38 $^1$H NMR (500 MHz, DMSO-d6) δ (ppm) 11.88, 11.94 (2s, 1H), 9.28, 9.34 (2d, 1H), 7.43-7.56 (m, 3H), 7.37 (t, 1H), 7.18-7.26 (m, 2H), 6.93 (t, 1H), 4.63 (t, 1H), 4.54 (t, 1H), 3.12 (s, 4H), 2.72 (t, 1H), 2.64 (s, 4H).

B39, $^1$H NMR (500 MHz, DMSO-d6) δ (ppm) 11.88, 11.94 (2s, 1H), 9.29, 9.35 (d, 1H), 7.43-7.55 (m, 3H), 7.37 (t, 1H), 7.23 (q, 1H), 7.15 (d, 1H), 6.92 (t, 1H), 4.55 (t, 1H), 4.45 (t, 1H), 3.11 (s, 4H), 2.55 (t, 4H), 2.43 (t, 2H), 1.88 (t, 1H), 1.82 (t, 1H).

B78, $^1$H-NMR (500 MHz, DMSO-d6) δ (ppm) 11.74, 11.88 (d, 1H), 9.40, 9.50 (d, 1H), 7.49-7.67 (m, 4H), 7.25-7.33 (m, 1H), 6.87-7.00 (m, 1H), 6.70-6.76 (m, 1H), 1.87-4.81 (m, 18H).

B79, $^1$H-NMR (500 MHz, DMSO-d6) δ (ppm) 11.72, 11.85 (s, 1H), 9.39, 9.49 (d, 1H), 7.44-7.67 (m, 4H), 7.25-7.33 (m, 1H), 6.90, 6.94 (s, 1H), 6.72 (t, 1H), 4.76 (d, 2H), 4.55 (d, 2H), 3.50-3.58 (m, 4H), 2.92 (d, 2H), 2.67 (d, 2H), 1.84-1.86 (m, 2H).

B80, $^1$H-NMR (500 MHz, DMSO-d6) δ (ppm) 12.13 (s, 1H), 11.68, 11.71, 11.28 (s, 1H), 9.24, 9.34 (d, 1H), 7.40-7.53 (m, 3H), 7.31-7.35 (m, 1H), 7.18-7.25 (m, 1H), 6.95-7.00 (m, 1H), 6.73-6.75 (m, 1H), 1.86-3.93 (m, 14H).

B81, $^1$H-NMR (500 MHz, DMSO-d6) δ (ppm) 11.31, 11.73, 11.87 (s, 1H), 9.38, 9.48, 9.75, 9.82 (d, 1H), 8.33-8.34, 7.81-7.84, 7.40-7.61 (m, 4H), 7.24-7.32 (m, 1H), 6.84-6.99 (m, 1H), 6.72 (t, 1H), 1.75-4.92 (m, 17H), B83, $^1$H-NMR (CDCl3, 500 MHz) δ 1.81-4.55 (m, 22H), 11.19, 11.27 (s, 1H), 9.44, 9.50 (d, 1H), 6.68-7.62 (m, 6H).

B82, $^1$H-NMR (CDCl3, 500 MHz) δ 1.17-4.54 (m, 16H), 10.85, 11.11 (s, 2H), 9.37-9.40 (m, 1H), 7.58 (s, 1H), 7.11-7.43 (m, 5H), 6.71-6.76 (m, 1H).

Example 3

General procedure for the N-Alkylation of B22 and B76 by by reductive amination. To a solution of B23 or B76 in ethanol was added 2.5 eq of triethylamine and 3.5 eq of aldehydes. After one hour, 5.6 eq of sodium cyanoborohydride was added to the mixture, which was stirred at room temperature for 24 h. The mixture was concentrated under reduced pressure. The crude product was purified by column chromatography to give the compounds.

B43, $^1$H NMR (500 MHz, DMSO-d6) δ (ppm) 12.18 (s, 1H), 11.87, 11.93 (2s, 1H), 9.27, 9.33 (2d, 1H), 7.84-7.90 (m, 4H), 7.45-7.60 (m, 6H), 7.38 (t, 1H), 7.18-7.26 (m, 2H), 6.93 (t, 1H), 3.71 (s, 2H), 3.14 (s, 4H), 2.62 (s, 4H).

B44, $^1$H NMR (500 MHz, DMSO-d6) δ (ppm) 12.14 (s, 1H), 11.85, 11.91 (2s, 1H), 9.31, 9.36 (2d, 1H), 7.80 (d, 2H), 7.58 (d, 2H), 7.50-7.55 (m, 2H), 7.44 (t, 1H), 7.38 (t, 1H), 7.24 (q, 1H), 7.17 (d, 1H), 6.93 (t, 1H), 3.66 (s, 2H), 3.20 (s, 4H), 2.57 (s, 4H).

B45, $^1$H NMR (500 MHz, DMSO-d6) δ (ppm) 12.20 (s, 1H), 11.85, 11.91 (2s, 1H), 9.25, 9.31 (2d, 1H), 7.40-7.52 (m, 3H), 7.33 (t, 1H), 7.21 (q, 1H), 7.13 (t, 1H), 7.10 (d, 2H), 6.89 (t, 1H), 6.66 (d, 1H), 3.39 (s, 2H), 3.08 (s, 4H), 2.83 (s, 6H), 2.50 (s, 4H).

B46, $^1$H NMR (500 MHz, DMSO-d6) δ (ppm) 12.18 (s, 1H), 11.87, 11.93 (2s, 1H), 9.28, 9.35 (2d, 1H), 8.60 (s, 1H), 7.43-7.57 (m, 3H), 7.38 (t, 1H), 7.13-7.27 (m, 2H), 6.92 (t, 1H), 6.51 (d, 1H), 6.41 (d, 1H), 3.66 (s, 2H), 3.27 (s, 4H), 2.75 (s, 4H). δ.

B47, $^1$H NMR (500 MHz, DMSO-d6) δ (ppm) 11.88, 11.94 (2s, 1H), 9.27, 9.30 (2d, 1H), 8.53 (d, 2H), 7.43-7.55 (m, 3H), 7.37 (d, 2H), 7.34 (t, 1H), 7.14-7.25 (m, 3H), 6.92 (t, 1H), 3.59 (s, 2H), 3.15 (s, 4H), 2.58 (s, 4H).

B48, $^1$H NMR (500 MHz, DMSO-d6) δ (ppm) 11.87, 11.94 (2s, 1H), 9.27, 9.33 (2d, 1H), 8.54 (s, 1H), 8.42 (d, 2H), 7.75 (d, 1H), 7.43-7.56 (m, 3H), 7.36-7.39 (m, 2H), 7.23 (q, 1H), 7.15 (d, 2H), 6.92 (t, 1H), 3.58 (s, 2H), 3.12 (s, 4H), 2.57 (s, 4H).

B49, $^1$H NMR (500 MHz, DMSO-d6) δ (ppm) 11.88, 11.94 (2s, 1H), 9.28, 9.34 (2d, 1H), 8.42, 8.52 (2d, 1H), 7.78 (t, 1H), 7.43-7.57 (m, 3H), 7.38 (t, 1H), 7.18-7.35 (m, 3H), 6.93 (t, 1H), 6.50 (s, 1H), 3.67 (s, 2H), 3.14 (s, 4H), 2.62 (s, 4H).

B87, $^1$H-NMR (500 MHz, DMSO-d6) δ (ppm) 12.11, 12.16 (s, 1H), 11.68, 11.80 (s, 1H), 9.25, 9.34 (d, 1H), 8.49 (s, 1H), 8.44 (d, 1H), 7.69 (d, 1H), 7.17-7.51 (m, 5H), 6.89, 6.95 (s, 1H), 6.70 (d, 1H), 3.66 (s, 2H), 3.56 (s, 2H), 3.52 (s, 2H), 2.75 (s, 2H), 2.56 (s, 2H), 1.98 (s, 2H).

Example 4

General procedure for the N-arylation of B22 and B76. A mixture of the 1.5 eq of haloheteroaryls, 1 eq of B23 or B76 and 2 eq of N,N-diisopropylethylamine in n-butanol was stirred at 140° C. for 24 h. The mixture was then cooled to room temperature, diluted with water, and extracted with ethyl acetate. The solvent was evaporated under reduced pressure and the residue was purified by silica gel column chromatography to give the compound.

B59, $^1$H NMR (500 MHz, DMSO-d6) δ (ppm) 11.94, 11.99 (2s, 1H), 9.28, 9.34 (2d, 1H), 9.01 (s, 1H), 7.51-7.59 (m, 3H), 7.46 (t, 1H), 7.38 (t, 1H), 7.24-7.27 (m, 2H), 6.99 (t, 1H), 5.71 (d, 1H), 3.57 (t, 4H), 3.23 (t, 4H).

B61, $^1$H NMR (500 MHz, DMSO-d6) δ (ppm) 11.30, 11.33 (2s, 1H), 10.44, 10.53 (2s, 1H), 9.46, 9.49 (2d, 1H), 8.15 (s, 2H), 7.50 (q, 1H), 7.30-7.47 (m, 3H), 7.21 (t, 1H), 7.01-7.05 (m, 2H), 3.73 (s, 4H), 3.31 (s, 4H).

B63, $^1$H NMR (500 MHz, DMSO-d6) δ (ppm) 12.00, 12.06 (2s, 1H), 9.42, 9.48 (2d, 1H), 7.51-7.70 (m, 6H), 7.33 (q, 1H), 7.20 (d, 1H), 6.97 (t, 1H), 3.57 (t, 4H), 3.13 (t, 2H), 3.07 (t, 2H).

B64, $^1$H NMR (500 MHz, DMSO-d6) δ (ppm) 11.97, 12.02 (2s, 1H), 9.30, 9.36 (2d, 1H), 8.18 (d, 1H), 7.57-7.61 (m, 3H), 7.48 (t, 1H), 7.40 (t, 1H), 7.24-7.28 (m, 2H), 7.03 (t, 1H), 6.93 (d, 1H), 6.70 (t, 1H), 3.68 (t, 4H), 3.22 (t, 4H).

B65, $^1$H NMR (500 MHz, CDCl3) δ (ppm), 11.20, 11.26 (2s, 1H), 9.45 (d, 1H), 8.35 (t, 1H), 8.15 (d, 1H), 7.17-7.50 (m, 7H), 7.01 (d, 1H), 6.67 (m, 1H), 3.67 (s, 4H), 3.32 (s, 4H).

B67, $^1$H NMR (500 MHz, CDCl3) δ (ppm) 11.30, 11.36 (2s, 1H), 9.45 (m, 1H), 7.69-7.71 (m, 1H), 7.29-7.51 (m, 6H), 7.04 (m, 1H), 3.78 (t, 4H), 3.20 (t, 4H), 3.15 (s, 6H), 2.33 (s, 3H).

B68, $^1$H NMR (500 MHz, DMSO-d6) δ (ppm) 11.93, 11.98 (2s, 1H), 9.29, 9.30 (2d, 1H), 8.39, 8.40 (d, 2H), 7.53-7.58 (m, 2H), 7.42-7.48 (m, 2H), 7.39 (t, 1H), 7.21-7.28 (m, 2H), 7.00 (t, 1H), 6.65 (t, 1H), 3.93 (t, 4H), 3.18 (t, 4H).

B69, $^1$H NMR (500 MHz, DMSO-d6) δ (ppm) 11.94, 12.00 (2s, 1H), 9.29, 9.35 (2d, 1H), 8.40 (s, 1H), 8.12 (t, 1H), 7.87 (d, 1H), 7.52-7.56 (m, 2H), 7.46 (t, 1H), 7.37 (t, 1H), 7.22-7.27 (m, 2H), 6.71-7.00 (m, 1H), 3.76 (t, 4H), 3.17 (t, 4H).

B93, $^1$H NMR (500 MHz, DMSO-d6) δ (ppm) 12.17 (s, 1H), 11.74 (s, 1H), 8.11 (m, 2H), 7.49-7.53 (m, 1H), 7.46 (d, 2H), 7.35 (m, 1H), 7.23 (m, 1H), 7.03 (m, 1H), 6.93 (d, 2H), 6.77 (d, 1H), 3.82 (s, 1H), 3.70 (s, 1H), 3.56 (s, 1H), 3.51 (s, 1H), 3.17 (s, 1H), 2.09 (s, 2H), 1.76 (s, 1H), 1.24 (m, 2H).

B94, $^1$H-NMR (DMSO-d6, 500 MHz) δ 2.04-4.04 (m, 10H), 12.12, 12.16 (s, 1H), 11.69, 11.81 (s, 1H), 9.24, 9.35 (d, 1H), 7.40-8.05 (m, 4H), 7.30-7.35 (m, 1H), 7.18-7.25 (m, 1H), 6.97, 7.03 (s, 1H), 6.75-6.85 (m, 1H), 6.67 (t, 1H), 6.50 (t, 1H).

B95, $^1$H-NMR (500 MHz, DMSO-d6) δ (ppm) 12.12, 12.15 (s, 1H), 11.66, 11.79 (s, 1H), 9.22, 9.32 (d, 1H), 8.30 (d, 1H), 8.05 (d, 1H), 7.18-7.54 (m, 5H), 6.92, 6.96 (s, 1H), 6.68-6.72 (m, 2H), 2.03-3.82 (d, 10H).

B96, $^1$H-NMR (DMSO-d6, 500 MHz) δ.1.93-3.65 (m, 10H), 12.14 (s, 1H), 11.71, 11.83 (s, 1H), 9.26 (d, 1H), 7.42-7.95 (m, 5H), 7.33 (d, 1H), 7.22 (t, 1H), 7.00 (s, 1H), 6.75 (d, 1H).

B97, $^1$H-NMR (500 MHz, DMSO-d6) δ (ppm) 12.13 (s, 1H), 11.69, 11.81 (s, 1H), 9.26 (s, 1H), 7.41-7.52 (m, 3H), 7.32 (d, 1H), 7.23 (t, 1H), 7.01 (s, 1H), 6.76 (d, 1H), 5.89 (s, 1H), 3.68 (s, 2H), 3.48 (s, 2H), 3.31 (s, 4H), 3.04 (s, 6H), 2.11 (s, 3H), 2.01 (t, 2H).

B98, $^1$H-NMR (500 MHz, DMSO-d6) δ (ppm) 12.13 (s, 1H), 11.69, 11.80 (s, 1H), 9.23, 9.33 (d, 1H), 7.32-7.55 (m, 4H), 7.19-7.26 (m, 1H), 6.96, 7.01 (s, 1H), 6.77 (t, 1H), 6.55 (t, 1H), 3.98 (s, 2H), 3.66 (s, 2H), 3.62 (d, 2H), 2.55 (s, 2H), 2.00 (d, 2H).

B99, $^1$H-NMR (500 MHz, DMSO-d6) δ (ppm) 12.12 (s, 1H), 11.69, 11.81 (s, 1H), 9.25 (s, 1H), 8.18 (s, 1H), 8.00 (s, 1H), 7.71 (s, 1H), 7.41-7.52 (m, 3H), 7.33 (d, 1H), 7.21 (t, 1H), 7.02 (s, 1H), 6.77 (d, 1H), 3.90 (s, 2H), 3.68 (s, 2H), 3.57 (s, 2H), 3.50 (s, 2H), 2.04 (t, 2H).

B100, $^1$H-NMR (500 MHz, DMSO-d6) δ (ppm) 12.11 (s, 1H), 11.70, 11.82 (s, 1H), 9.23, 9.34 (d, 1H), 7.30-7.53 (m, 4H), 7.16 7.24 (m, 2H), 6.97-7.07 (m, 2H), 6.75 (d, 1H), 3.93 (s, 2H), 3.67 (s, 2H), 3.54 (s, 2H), 3.46 (s, 2H), 2.38 (s, 3H), 2.03 (t, 2H).

Example 5

General procedure for the N-acylation/sulfonylation of B22 and B76. To a mixture of 1 eq of B23 or B76 and 1.5 eq of N,N-diisopropylethylamine in dichloromethane was added 1.2 eq of acyl chlorides or sulfonyl chlorides and stirred at room temperature overnight. The mixture was then washed with sodium bicarbonate solution. The solvent was evaporated under reduced pressure and the residue was purified by silica gel column chromatography to give the compound.

B54, ¹H-NMR (500 MHz, DMSO-d6) δ (ppm) 11.95, 12.00 (s, 1H), 9.28, 9.33 (d, 1H), 8.09 (s, 1H), 7.44-7.57 (m, 3H), 7.38 (t, 1H), 7.19-7.27 (m, 2H), 6.96 (t, 1H), 3.55-3.58 (m, 4H), 3.05-3.12 (m, 4H).

B57, ¹H-NMR (500 MHz, DMSO-d6) δ (ppm) 12.20 (s, 1H), 11.97, 12.02 (s, 1H), 9.32, 9.38 (d, 1H), 7.47-7.61 (m, 3H), 7.40 (t, 1H), 7.23-7.31 (m, 2H), 6.97-7.00 (m, 1H), 3.19-3.25 (m, 8H), 2.97 (s, 3H).

B58, ¹H NMR (500 MHz, DMSO-d6) δ (ppm) 12.7 (s, 1H), 9.27 (s, 1H), 8.92 (d, 1H), 7.68-7.78 (m, 3H), 7.52 (t, 1H), 7.30 (s, 1H), 7.20 (t, 1H), 3.29-3.41 (m, 12H).

B88, ¹H-NMR (500 MHz, DMSO-d6) δ (ppm) 12.13, 12.17 (s, 1H), 11.69, 11.83 (s, 1H), 9.25, 9.35 (d, 1H), 7.76, 8.01 (s, 1H), 7.40-7.52 (m, 3H), 7.33 (t, 1H), 7.21 (dd, 1H), 6.95, 6.99 (s, 1H), 6.74 (d, 1H), 3.24-3.71 (m, 8H), 1.86 (s, 2H).

B89, ¹H-NMR (500 MHz, DMSO-d6) δ (ppm) 11.71, 11.83 (s, 1H), 9.24, 9.34 (d, 1H), 7.33-8.09 (m, 5H), 7.18-7.22 (m, 1H), 6.96, 7.01 (s, 1H), 6.58, 6.75 (d, 1H), 3.66 (m, 4H), 2.42 (t, 2H), 2.34 (t, 2H), 2.25 (t, 2H), 1.98 (t, 2H), 1.88 (t, 2H).

B90, ¹H-NMR (500 MHz, DMSO-d6) δ (ppm) 12.13, 12.17 (s, 1H), 11.71, 11.84 (s, 1H), 9.25, 9.35 (d, 1H), 7.41-7.54 (m, 3H), 7.33 (t, 1H), 7.19-7.26 (m, 1H), 6.97, 7.02 (s, 1H), 6.76 (t, 1H), 1.95-3.67 (m, 13H).

B91, ¹H-NMR (500 MHz, DMSO-d6) δ (ppm) 12.13, 12.17 (s, 1H), 11.71, 11.83 (s, 1H), 9.25, 9.34 (d, 1H), 7.39-7.52 (m, 3H), 7.33 (t, 1H), 7.22 (dd, 1H), 6.75 (d, 1H), 6.67, 7.01 (s, 1H), 1.39-3.65 (m, 16H).

Example 6

General procedure for the preparation of urea type compounds. Starting material B6 and 1.5 eq isocyanate 22 were mixed in dichloromethane and allowed to react at room temperature for 1 day. After working up, the residue was then purified by column chromatography to give the target urea compound.

B55, ¹H-NMR (500 MHz, DMSO-d6) δ (ppm) 12.21 (s, 1H), 11.92, 11.98 (2s, 1H), 9.28, 9.35 (2d, 1H), 8.60 (s, 1H), 7.46-7.58 (m, 5H), 7.39 (t, 1H), 7.23-7.28 (m, 4H), 6.99 (t, 1H), 6.94 (t, 1H), 3.65 (s, 4H), 3.15 (s, 4H).

B118, ¹H-NMR (500 MHz, DMSO-d6) δ (ppm) 12.25 (s, 1H), 12.13 & 12.11 (s, 1H), 9.41 & 9.36 (d, 1H), 9.15 & 9.11 (s, 1H), 8.87 & 8.76 (s, 1H) 8.18-8.17 (m, 1H), 7.92 & 7.86 (s, 1H), 7.70-7.23 (m, 8H). LC-MS (m/z) 498 [M+1].

B119, ¹H-NMR (500 MHz, DMSO-d6) δ (ppm) 12.21 (s, 1H), 12.09 (s, 1H), 9.35 (s, 1H), 9.17 (s, 1H), 8.84 (s, 1H), 8.68 (d, 1H), 7.89 (s, 1H), 7.58 (dd, 2H), 7.49 (t, 2H), 7.40 (d, 2H), 7.28 (t, 1H), 7.20 (d, 1H).

B120, ¹H-NMR (500 MHz, DMSO-d6) δ (ppm) 12.09, 12.20 (s, 1H), 12.05, 12.08 (s, 1H), 9.32, 9.37 (d, 1H), 8.09-9.16 (m, 2H), 7.87 (t, 1H), 7.55-7.62 (m, 2H), 7.46-7.52 (m, 1H), 7.36-7.41 (m, 1H), 6.80-7.30 (m, 3H).

B121, ¹H-NMR (500 MHz, DMSO-d6) δ (ppm) 12.04, 12.06 (s, 1H), 9.31, 9.36 (d, 1H), 8.66, 8.70 (s, 1H), 8.60, 8.63 (s, 1H), 7.84, 7.87 (s, 1H), 7.54-7.61 (m, 2H), 7.44-7.51 (m, 3H), 7.38 (t, 1H), 7.16-7.30 (m, 4H), 6.96 (t, 1H).

B122, ¹H-NMR (500 MHz, DMSO-d6) δ (ppm) 12.11 (s, 1H), 12.20 (s, 1H), 9.63, 9.67 (s, 1H), 9.32, 9.36 (d, 1H), 9.15, 9.25 (s, 1H), 7.81, 7.87 (s, 1H), 7.53-7.62 (m, 4H), 7.49 (t, 1H), 7.40 (t, 1H), 7.28 (dd, 1H), 7.21 (t, 1H).

B123, ¹H-NMR (DMSO-d6, 500 MHz) δ 12.02 (s, 1H), 9.30, 9.34 (s, 1H), 8.62, 8.74 (s, 1H), 7.85 (s, 1H), 7.64 (s, 1H), 7.50-7.59 (m, 2H), 7.46 (s, 1H), 7.35-7.40 (m, 1H) 7.20-7.28 (m, 2H), 7.10-7.15 (m, 3H), 2.62 (dd, 2H), 2.24 (s, 3H), 1.15 (t, 3H).

B124, ¹H-NMR (500 MHz, DMSO-d6) δ (ppm) 12.17 (s, 1H), 11.96, 11.99 (s, 1H), 9.29, 9.34 (d, 1H), 8.16, 8.27 (s, 1H), 7.76 (s, 1H), 7.36 (t, 1H), 7.34-7.59 (m, 3H), 7.24 (dd, 1H), 7.06, 7.12 (d, 1H).

B125, ¹H-NMR (500 MHz, DMSO-d6) δ (ppm) 12.20 (s, 1H), 12.06, 12.08 (s, 1H), 9.32, 9.37 (d, 1H), 8.99, 9.08 (s, 1H), 8.49 (d, 1H), 8.21 (t, 1H), 7.87 (s, 1H), 7.52 (m, 2H), 7.48 (t, 1H), 7.39 (t, 1H), 7.13-7.30 (m, 4H), 6.99 (dd, 1H).

B126, ¹H-NMR (500 MHz, DMSO-d6) δ (ppm) 12.05 (s, 1H), 9.31, 9.36 (d, 1H), 9.30, 9.32 (s, 1H), 9.07, 9.16 (s, 1H), 7.84, 7.89 (s, 1H), 7.52-7.60 (m, 3H), 7.47 (t, 1H), 7.38 (t, 1H), 7.15-7.31 (m, 4H), 6.74 (t, 1H).

B127, ¹H-NMR (500 MHz, DMSO-d6) δ (ppm) 12.04, 12.06 (s, 1H), 9.30, 9.35 (d, 1H), 8.91, 8.93 (s, 1H), 8.82, 8.91 (s, 1H), 7.83, 7.87 (s, 1H), 7.45-7.60 (m, 5H), 7.38 (t, 1H), 7.17-7.28 (m, 2H), 7.11 (t, 2H).

B128, ¹H-NMR (500 MHz, DMSO-d6) δ (ppm) 12.20 (s, 1H), 12.07, 12.08 (s, 1H), 9.32, 9.36 (d, 1H), 8.94, 9.04 (s, 1H), 8.46, 8.47 (s, 1H), 8.15 (dd, 1H), 7.86 (s, 1H), 7.51-7.61 (m, 2H), 7.48 (t, 1H), 7.39 (t, 1H), 7.13-7.32 (m, 3H), 7.05 (t, 1H).

B129, ¹H-NMR (500 MHz, DMSO-d6) δ (ppm) 12.19 (s, 1H), 12.06 (s, 1H), 9.32 (d, 1H), 8.79, 8.88 (s, 1H), 8.00 (1H, s), 7.84 (1H, s), 7.56 (t, 2H), 7.48 (t, 1H), 7.38 (d, 1H), 7.24-7.33 (m, 2H), 7.13-7.20 (m, 3H).

B130, ¹H-NMR (500 MHz, DMSO-d6) δ (ppm) 12.19 (s, 1H), 12.06 (s, 1H), 9.32, 9.37 (d, 1H), 8.87 (d, 1H), 8.69, 8.79 (s, 1H), 7.78-7.85 (m, 2H), 7.46-7.60 (m, 3H), 7.39 (t, 1H), 7.17-7.33 (m, 4H).

B131, ¹H-NMR (500 MHz, DMSO-d6) δ (ppm) 12.19 (s, 1H), 12.08 (s, 1H), 9.32, 9.36 (d, 1H), 9.31, 9.40 (s, 1H), 8.01, 8.03 (s, 2H), 7.85, 7.88 (s, 1H), 7.56-7.68 (m, 4H), 7.48 (t, 1H), 7.39 (t, 1H), 7.13-7.30 (m, 3H).

B132, ¹H-NMR (500 MHz, DMSO-d6) δ (ppm) 12.20 (s, 1H), 12.06, 12.08 (s, 1H), 9.32, 9.37 (d, 1H), 8.98, 9.01 (s, 1H), 8.69, 8.79 (s, 1H), 8.05 (s, 1H), 7.83, 7.89 (s, 1H), 7.46-7.61 (m, 5H), 7.39 (t, 1H), 7.20-7.30 (m, 3H).

B133, ¹H-NMR (500 MHz, DMSO-d6) δ (ppm) 12.20 (s, 1H), 12.08 (s, 1H), 9.32, 9.37 (d, 1H), 9.02, 9.05 (s, 1H), 8.69, 8.79 (s, 1H), 7.84, 7.88 (s, 1H), 7.58-7.69 (m, 6H), 7.48 (t, 1H), 7.39 (t, 1H), 7.18-7.28 (m, 2H).

B134, ¹H-NMR (500 MHz, DMSO-d6) δ (ppm) 10.02-12.20 (m, 1H), 8.90-9.39 (m, 2H), 6.52-8.18 (m, 12H).

B135, ¹H-NMR (500 MHz, DMSO-d6) δ (ppm) 12.08, 12.10 (s, 1H), 9.49, 9.58 (s, 1H), 9.32, 9.38 (d, 1H), 7.88, 7.91 (d, 1H), 7.71 (d, 1H), 7.52-7.61 (m, 2H), 7.49 (t, 1H), 7.40 (t, 1H), 7.35 (dd, 1H), 7.16-7.31 (m, 2H).

B136, ¹H-NMR (500 MHz, DMSO-d6) δ (ppm) 12.09 (s, 1H), 9.39, 9.47 (s, 1H), 9.32, 9.35 (d, 1H), 8.14 (s, 1H), 8.08 (dd, 1H), 7.85-7.88 (m, 1H), 7.71-7.75 (m, 3H), 7.52-7.61 (m, 2H), 7.48 (t, 1H), 7.40 (t, 1H), 7.13-7.30 (m, 2H).

B137, ¹H-NMR (500 MHz, DMSO-d6) δ (ppm) 12.04, 12.06 (s, 1H), 9.31, 9.36 (d, 1H), 9.26 (d, 1H), 8.18 (t, 2H), 7.88 (d, 1H), 7.51-7.61 (m, 2H), 7.47 (t, 1H), 7.39 (t, 1H), 7.13-7.30 (m, 2H), 7.02 (d, 1H), 6.891-6.954 (m, 2H), 3.894 (s, 3H).

B138, ¹H-NMR (500 MHz, DMSO-d6) δ (ppm) 12.04, 12.06 (s, 1H), 9.31, 9.35 (d, 1H), 8.62, 8.65 (d, 2H), 7.83, 7.87 (s, 1H), 7.54-7.61 (m, 2H), 7.48 (t, 1H), 7.39 (t, 1H), 7.15-7.30 (m, 4H), 6.95 (t, 1H), 6.54 (d, 1H), 3.74 (s, 3H).

Example 7

General procedure for the preparation of amide derivatives by coupling acid B7 with amines. B7 and 1.5 eq of HBTU (2-(1H-Benzotriazole-1-yl)-1,1,3,3-tetramethyluronium hexafluorophosphate) were mixed in dichloromethane in a round-bottomed flask at room temperature. After 10 minutes, 3 eq of amine was added dropwise. The reaction mixture was stirred overnight at room temperature under nitrogen. The mixture was diluted with ethyl acetate and washed with sodium carbonate solution. The organic layer was separated, dried with anhydrous magnesium sulfate, and then evaporated in vacuum. The crude product was purified by a flash column to give the compound.

B71, $^1$H-NMR (500 MHz, DMSO-d6) δ (ppm) 12.42 (d, 1H), 10.10 (s, 1H), 9.42 (d, 1H), 7.73-7.82 (m, 3H), 7.63 (t, 1H), 7.52 (d, 1H), 7.40 (t, 1H), 7.30 (d, 1H), 3.55 (t, 4H), 2.94 (t, 4H), 2.66 (s, 3H).

B72, $^1$H-NMR (500 MHz, DMSO-d6) δ (ppm) 9.39 (d, 2H), 8.51 (s, 2H), 8.24 (s, 1H), 7.82 (d, 1H), 7.59-7.67 (m, 3H), 7.55 (d, 1H), 7.50 (d, 1H), 7.32 (t, 2H), 6.69 (s, 1H), 3.50 (t, 4H), 3.29 (t, 4H).

B73, $^1$H-NMR (500 MHz, DMSO-d6) δ (ppm) 12.42 (s, 1H), 12.28 (br, 1H), 10.25 (d, 1H), 9.43 (dd, 1H), 8.02 (dd, 1H), 7.90 (t, 1H), 7.76 (d, 1H), 7.72 (m, 2H), 7.62 (m, 1H), 7.50 (m, 1H), 7.35 (m, 1H), 7.05 (d, 1H), 3.30 (t, 4H), 2.01 (t, 4H).

B74, $^1$H-NMR (500 MHz, DMSO-d6) δ (ppm) 12.36 (s, 1H), 9.41 (s, 1H), 7.74 (s, 1H), 7.67-7.69 (m, 2H), 7.56 (d, 1H), 7.47 (d, 1H), 7.36 (t, 1H), 7.22 (s, 1H), 4.11 (s, 1H), 3.67 (d, 1H), 3.51 (s, 1H), 3.20 (s, 1H), 2.64 (m, 1H), 2.53 (s, 3H), 2.32 (d, 2H), 1.83 (d, 2H), 1.79 (s, 1H), 1.26 (s, 1H).

B92, $^1$H-NMR (500 MHz, DMSO-d6) δ (ppm) 12.35 (s, 1H), 9.40 (t, 1H), 8.03 (m, 2H), 7.66 (m, 2H), 7.60 (m, 2H), 7.47 (d, 1H), 7.37 (t, 1H), 7.09 (m, 1H), 6.86 (m, 1H), 6.65 (m, 1H), 3.59-3.84 (m, 5H), 3.20 (s, 1H), 1.99 (s, 2H), 1.83 (d, 2H), 1.61-1.82 (m, 2H), 1.26 (s, 1H).

Example 8

General procedure for the preparation of imidazo[1,2-a]pyridine type compounds.

Equal mole of compound 3-(bromoacetyl)-1-azaazulen-2-one and 2-aminopyridines were added into ethanol and heat to reflux for 1 day. The solvent was evaporated under vacuum, the residue was partitioned between ethyl acetate and sodium carbonate solution. The ethyl acetate layer was separated and worked up. The residue was purified by column chromatography to give the target compound.

B9, $^1$H-NMR (500 MHz, DMSO-d6) δ (ppm) 11.84 (s, 1H), 9.33 (d, 1H), 8.67 (d, 1H), 8.66 (s, 1H), 7.64 (d, 1H), 7.29 (t, 1H), 7.27 (t, 1H), 7.25 (t, 1H), 7.13 (d, 1H), 7.04 (t, 1H), 6.92 (t, 1H). LC-MS (m/z) 262 [M+1].

B10, $^1$H-NMR (500 MHz, DMSO-d6) δ (ppm) 12.27, 12.37 (s, 1H), 11.47, 11.53, 12.20 (s, 1H), 9.30, 9.40 (d, 1H), 8.13, 8.20 (s, 1H), 6.76-7.79 (m, 5H).

B13, $^1$H-NMR (500 MHz, DMSO-d6) δ (ppm) 11.95 (s, 1H), 9.44 (s, 1H), 9.30 (d, 1H), 8.76 (s, 1H), 7.79 (d, 1H), 7.53 (d, 1H), 7.31-7.40 (m, 2H), 7.22 (d, 1H), 7.11 (t, 1H).

B14, $^1$H-NMR (500 MHz, DMSO-d6) δ (ppm) 9.03 (d, 1H), 8.43 (s, 1H), 8.19 (s, 1H), 7.53 (d, 1H), 7.30-7.7.36 (m, 2H), 7.13 (t, 1H), 3.90 (s, 3H).

B16, $^1$H-NMR (500 MHz, DMSO-d6) δ (ppm) 11.84 (s, 1H), 9.25 (d, 1H), 8.68 (d, 1H), 8.67 (s, 1H), 7.77 (s, 1H), 7.22-7.30 (m, 2H), 7.13 (d, 1H), 6.68-7.04 (m, 2H).

B17, $^1$H-NMR (DMSO-d6, 500 MHz) δ 11.85 (s, 1H), 9.26 (d, 1H), 9.00 (s, 1H), 8.65 (s, 1H), 7.60 (H, 1H), 7.23-7.37 (m, 3H), 7.14 (d, 1H), 7.04 (t, 1H).

Example 9

General procedure for the preparation of imidazo[1,2-a]pyrimidine type compounds. Equal mole of 3-(bromoacetyl)-1-azaazulen-2-one and 2-aminopyrimidines were added into ethanol and heat to reflux for 1 day. The solvent was evaporated under vacuum, the residue was partitioned between ethyl acetate and sodium carbonate solution. The ethyl acetate layer was separated and worked up. The residue was purified by column chromatography to give target compounds.

B12, $^1$H-NMR (500 MHz, DMSO-d6) δ (ppm) 11.91 (broad, 1H), 9.36 (d, 1H), 9.07 (d, 1H), 8.64 (s, 1H), 8.55 (s, 1H), 7.37 (t, 1H), 7.33 (t, 1H), 7.20 (d, 1H), 7.12-7.08 (m, 2H). LC-MS (m/z) 263 [M+1].

Example 10

General procedure for the preparation of indole type compounds. Equal mole of 2-(3-fluorophenyl)acetic acid and 1-azaazulen-2-one were added into Eaton's reagent (2 ml per mmole of reactant) and heat at 80 degree for 1 day. The mixture was dumped into 50 ml water and stirred for 30 minutes. The product was filtered off, washed with water and aspirated to dry. Part of the product 3-(2-(3-fluorophenyl)acetyl)-1-azaazule-2-one (201 mg) was dissolved in concentrated sulfuric acid (2 ml) and cooled in an ice bath and then concentrated nitric acid (65 mg) was added and stirred for 1 hour. Water (5 ml) was added to dilute the reaction mixture. The solid product was filtered off, washed with water and methanol, then dried to give the nitro product. 3-(2-(5-fluoro-2-nitrophenyl)acetyl)-1-azaazule-2-one (57 mg), KF (41 mg) and N-methylpiperazine (109 mg) were dissolved in DMSO (3 ml) and heat at 120 degree for 3 hours. Water (10 ml) was added to dilute the reaction mixture. The solid product was filtered off, washed with water and then dried to give the product. 3-(2-(5-(4-methylpiperazin-1-yl)-2-nitrophenyl)acetyl)-1-azaazule-2-one (10 mg) was dissolved in methanol (5 mg) and hydrogenated with 2 atm hydrogen in the presence of Raney Nickel for 14 hours. The mixture was filtered and the filtrate was concentrated under vacuum to give 5.2 mg target compound 3-(5-(4-methylpiperazin-1-yl)-1H-indol-2-yl)-1-azaazule-2-one.

B143, $^1$H-NMR (500 MHz, DMSO-d6) δ (ppm) 10.04 (s, 1H), 11.01 (s, 1H), 8.07 (d, 1H), 7.49 (d, 1H), 7.29 (t, 2H), 7.16 (d, 1H), 7.11 (s, 1H), 7.06 (t, 1H), 6.94 (d, 1H), 6.90 (s, 1H), 3.49 (b, 4H), 2.82 (b, 4H), 2.53 (s, 3H).

Example 11

Kinase Assays

Azaazulene Compounds of this invention were treated for their efficacy in inhibiting activities of FLT-3, c-KIT and KDR kinases by biochemical DELFIA (Dissociation Enhanced Lanthanide FIA) assays according to the procedure described below. The assays were conducted by, Division of Cell Engineering, Biomedical Engineering Research Laboratories, Industrial Technology Research Institute, Bldg. 53, 195, sec. 4, Chung Hsing Rd. Chutung, Hsinchu, Taiwan 310, R.O.C.

The FLT-3 assay was conducted following the protocol described in Protocol for HTScang FLT-3 Kinase Assay Kit (Cell Signaling Technology®). The assay was conducted under the following conditions: FLT-3 source: The GST-kinase fusion protein was produced using a baculovirus expression system with a construct expressing human FLT-3 (Arg571-Ser993) (GenBank accession No. NM.sub.-004119) with an amino-terminal GST tag, substrate: 1.5 uM Gastrin Precursor Biotinylated Peptide (with Tyr87 as phosphorylation site), vehicle: 1% DMSO, pre-incubation time/ temperature: 5 minutes at room temperature, incubation time/temperature: 30 minutes at room temperature, incubation buffer: 60 mM HEPES pH 7.5, 5 mM $MgCl_2$, 5 mM $MnCl_2$, 3 uM Na3VO4, 1.25 mM DTT, 20 uM ATP, and quantitative method: DELFIA® Assay.

The inhibitory effects of azaazulene compounds of this invention against FLT-3 kinase are summarized in following Table 2.

TABLE 2

Kinases inhibitory activities of azaazulene compounds against FLT-3 kinase.

| Compound No. | FLT-3 inhibition at 1uM (%) | FLT-3 inhibition at 0.1uM (%) |
|---|---|---|
| A1 (Prior Art) | 59.4 | 11.5 |
| B1 | 10.4 | 8.4 |
| B2 | 59.9 | 18.9 |
| B4 | 37.1 | 13.7 |
| B5 | 27.1 | 12.8 |
| B6 | 45.1 | 12.8 |
| B7 | 8.7 | — |
| B8 | 68.5 | 9.8 |
| B9 | 19.1 | 5.8 |
| B10 | 20.3 | 8.9 |
| B11 | 27.3 | 12.5 |
| B12 | 1.6 | 4.5 |
| B14 | 9.6 | — |
| B15 | 18.1 | 8.6 |
| B16 | 16.5 | 4.8 |
| B17 | 23.4 | 4.9 |
| B18 | 40.2 | 16.4 |
| B19 | 28.6 | 14.7 |
| B20 | 33.3 | 16.7 |
| B21 | 63.0 | 20.1 |
| B22 | 83.9 | 29.1 |
| B23 | 91.5 | 41.2 |
| B24 | 71.5 | 19.1 |
| B26 | 91.2 | 45.6 |
| B32 | 8.1 | 8 |
| B33 | 96.6 | 58.7 |
| B34 | 85.4 | 40.2 |
| B35 | 86.7 | 42 |
| B36 | 64 | 24.8 |
| B38 | 69.2 | 21.8 |
| B39 | 78.6 | 24.3 |
| B40 | 88.1 | 38.2 |
| B43 | 67.2 | 33.5 |
| B44 | 79.1 | 29 |
| B45 | 77 | 27.3 |
| B46 | 79.2 | 27.4 |
| B49 | 72.2 | 21.9 |
| B50 | 79.6 | 25.1 |
| B51 | 66.6 | 20.6 |
| B52 | 42.5 | 20.3 |
| B54 | 91.6 | 46.0 |
| B55 | 93.2 | 45.2 |
| B57 | 81.5 | 29.5 |
| B58 | 83.8 | 35.7 |
| B59 | 96.1 | 55.6 |
| B60 | 99.1 | 71.7 |
| B61 | 74.3 | 17.7 |
| B62 | 13.7 | 9.5 |
| B63 | 33.4 | 18.9 |
| B64 | 79.2 | 29.5 |
| B65 | 60.5 | 16.3 |
| B66 | 55.5 | 20.3 |
| B67 | 95.3 | 43.3 |
| B68 | 80.7 | 39.1 |
| B69 | 77.3 | 29.3 |
| B70 | 27.5 | 11.1 |
| B71 | 39.3 | 6.8 |
| B72 | 85.5 | 36.8 |
| B73 | 22.3 | 23.7 |
| B74 | 64.0 | 27.1 |
| B75 | 37.1 | 13.4 |
| B76 | 92.9 | 50.0 |
| B77 | 94.3 | 47.1 |
| B78 | 39.4 | 20.3 |
| B79 | 36.6 | 22.3 |
| B80 | 71.4 | 23.1 |
| B81 | 21 | 9.9 |
| B82 | 81.6 | 30.3 |
| B83 | 21.2 | 11 |
| B85 | 89.8 | 44.4 |
| B87 | 91.6 | 39.8 |
| B88 | 62.4 | 20.6 |
| B89 | 56.7 | 20 |
| B90 | 59.2 | 23.0 |
| B91 | 42.5 | 14.3 |
| B92 | 51.4 | 17.9 |
| B93 | 89.4 | 44.2 |
| B94 | 52.3 | 17 |
| B95 | 37.7 | 14.4 |
| B96 | 35.7 | 10.9 |
| B97 | 44.6 | 8.8 |
| B98 | 69.5 | 17.8 |
| B99 | 51.8 | 17 |
| B100 | 20.2 | 9.1 |
| B101 | 90.7 | 46.8 |
| B102 | 67.8 | 22.8 |
| B103 | 87.4 | 36.5 |
| B104 | 84.1 | 28.3 |
| B105 | 86 | 38.7 |
| B106 | 76.2 | 24.2 |
| B107 | 92.9 | 42.5 |
| B108 | 86.5 | 16 |
| B109 | 35.2 | 17.3 |
| B110 | 84.9 | 36.5 |
| B111 | 75.0 | 24.5 |
| B112 | 21.3 | 9.5 |
| B113 | 42 | 14.8 |
| B114 | 16.3 | 10 |
| B115 | 72.7 | 25.4 |
| B116 | 62.7 | 36.3 |
| B118 | 76.3 | 57.9 |
| B119 | 44.6 | 32 |
| B120 | 10.1 | 10.2 |
| B130 | 24 | 8.6 |
| B131 | 7.3 | 7.9 |
| B132 | 72.4 | 47.5 |
| B133 | 53.3 | 30.5 |
| B134 | 57.3 | 36.8 |
| B135 | 62 | 41.4 |
| B136 | 70.8 | 21 |
| B137 | 19 | 14.3 |
| B138 | 58.1 | 35.6 |

The c-KIT assay was conducted following the protocol described in Protocol for HTScan® c-KIT Kinase Assay Kit (Cell Signaling Technology®). The assay was conducted under the following conditions: c-KIT source: The GST-c-KIT fusion protein was produced using a baculovirus expression system with a construct expressing human c-KIT (Thr544-Val976) with an amino-terminal GST tag, substrate: 1.5 uM This biotinylated peptide contains the residues surrounding Tyr-996 of KDR, vehicle: 1% DMSO, pre-incubation time/temperature: 5 minutes at room temperature, incubation time/temperature: 30 minutes at room temperature, incubation buffer: 60 mM HEPES pH 7.5, 5 mM $MgCl_2$, 5 mM $MnCl_2$, 3 uM $Na_3VO_4$, 1.25 mM DTT, 20 uM ATP, and quantitative method: DELFIA® Assay.

The inhibitory effects of azaazulene compounds of this invention against c-KIT kinase are summarized in following Table 3.

TABLE 3

Kinases inhibitory activities of azaazulene compounds against c-KIT kinase.

| Compound No. | c-Kit inhibition at 1uM (%) | c-Kit inhibition at 0.1uM (%) |
|---|---|---|
| A1 (Prior Art) | 64.5 | 34.1 |
| B1 | 41.1 | 31.2 |
| B2 | 57.9 | 6.4 |
| B4 | 37.6 | 5 |
| B5 | 56.8 | 15.2 |
| B6 | 62.6 | 32.6 |
| B7 | 57.3 | 34.8 |
| B8 | 75.5 | 42.2 |
| B9 | 24.4 | 16 |
| B11 | 43.7 | 15.1 |
| B13 | 25.6 | 32.2 |
| B14 | 39.4 | 20.1 |
| B15 | 43.1 | 8.5 |
| B21 | 55.4 | 10.8 |
| B70 | 86.6 | 40.5 |
| B80 | 82.9 | 56.7 |
| B81 | 17.2 | 28.9 |
| B82 | 91.1 | 31 |
| B83 | 19.7 | — |
| B87 | 96.2 | 49.6 |
| B88 | 89.2 | 47.2 |
| B94 | 79.1 | 12.3 |
| B95 | 82.6 | 48.3 |
| B97 | 87.2 | 40.1 |
| B118 | 36.8 | 66.6 |

The KDR assay was conducted following the protocol described in Protocol for HTScan™ VEGFR-2 Kinase Assay Kit (Cell Signaling Technology™). The assay was conducted under the following conditions: KDR source: The GST-Kinase fusion protein was produced using a baculovirus expression system with a construct expressing human VEGFR-2 (Val789-Val1356) (GenBank Accession No. NM.sub.-002253) with an amino-terminal GST tag, substrate: 1.5 uM Gastrin Precursor Biotinylated Peptide (with Tyr87 as phosphorylation site), vehicle: 1% DMSO, pre-incubation time/temperature: 5 minutes at room temperature, incubation time/temperature: 30 minutes at room temperature, incubation buffer: 60 mM HEPES pH 7.5, 5 mM $MgCl_2$, 5 mM $MnCl_2$, 3 uM $Na_3VO_4$, 1.25 mM DTT, 20 uM ATP, and quantitative method: DELFIA® & Assay.

The inhibitory effects of azaazulene compounds of this invention against KDR kinase are summarized in following Table 4.

TABLE 4

Kinases inhibitory activities of azaazulene compounds against KDR kinase.

| Compound No. | 1 uM | 0.1 uM |
|---|---|---|
| B1 | 3.7 | — |
| B2 | 94.5 | 78.3 |
| B4 | 17.8 | 14.4 |
| B5 | 45.3 | 31.7 |
| B6 | 63.3 | 29.7 |
| B7 | 46.1 | 20.2 |
| B8 | 63.8 | 15.9 |
| B9 | 13.2 | 0.5 |
| B26 | 96.9 | 71.3 |

Example 12

Kinase Panel Assays

The kinase panel assay of compound B26 of this invention was performed by SelectScreen® Kinase Profiling Services of Invitrogen. The inhibitory effects of 1000 nM of compound B26 against various kinases whom shown >50% inhibitory effects are summarized in following Table 5.

TABLE 5

Kinases inhibitory activities of B26 against various kinases.

| Kinase Tested | % Inhibition |
|---|---|
| AMPK A1/B1/G1 | 88 |
| AMPK A2/B1/G1 | 70 |
| BLK | 52 |
| CSF1R (FMS) | 60 |
| FGFR1 | 54 |
| FGFR2 | 48 |
| FGFR3 | 62 |
| FGFR3 K650E | 47 |
| FGR | 69 |
| FLT3 | 95 |
| FLT3 D835Y | 98 |
| FLT4 (VEGFR3) | 50 |
| KDR (VEGFR2) | 64 |
| KIT | 61 |
| LCK | 63 |
| LYN A | 57 |
| LYN B | 51 |
| MAP4K5 (KHS1) | 60 |
| NTRK1 (TRKA) | 89 |
| NTRK2 (TRKB) | 84 |
| NTRK3 (TRKC) | 76 |
| PHKG1 | 53 |
| RET | 81 |
| RET V804L | 79 |
| RET Y791F | 79 |
| SRC | 50 |
| SRC N1 | 52 |
| STK4 (MST1) | 59 |
| YES1 | 73 |

Example 13

In Vitro Cell Activity Assay

Human MV4-11 (FLT3-ITD) cell line was obtained from American Tissue Culture Collection (ATCC number: CRL-9591). The cell line was cultured with RPMI 1640 containing 10% fetal bovine serum, 1 mmol/L sodium pyruvate and 10 mmol/L HEPES (pH 7.4). The cell was grown and maintained in a humidified atmosphere at 37° C. and 5% carbon dioxide.

MV4-11 cell was plated in 96-well microtiter plates (10,000 cells per well) and serial dilutions of indicated compounds were added. At the end of the incubation period (72 hours at 37° C.), cell viability was determined by a tetrazolium dye, MTT (3-(4,5-dimethylthiazol-2-yl)-2,5-diphenyl tetrazolium bromide) (Promega, Madison, Wis.). The formazan crystals were dissolved by DMSO, and the absorbance at a wavelength of 600 nm was recorded using an ELISA plate reader. $IC_{50}$ values were calculated using nonlinear regression and defined as the concentration needed for a 50% reduction in absorbance of treated versus untreated control cells.

The inhibitory effects of azaazulene compounds of this invention against MV4-11 cell are summarized in following Table 6.

TABLE 6

Cell inhibitory activity of azaazulene compounds against MV4-11 cell

| Compound | IC$_{50}$ against MV4-11 (uM) |
| --- | --- |
| A1 | ≈1 |
| B1 | 1-5 |
| B2 | 1-5 |
| B3 | 1-5 |
| B4 | 1-5 |
| B5 | 1.3003 |
| B6 | 0.9162 |
| B7 | >5 |
| B8 | ≈0.5 |
| B9 | 1-5 |
| B10 | 1-5 |
| B11 | 1-5 |
| B12 | >5 |
| B13 | >5 |
| B14 | 1-5 |
| B15 | 1-5 |
| B16 | >5 |
| B17 | 1-5 |
| B19 | 1-5 |
| B20 | 1-5 |
| B21 | 0.4275 |
| B22 | 0.0429 |
| B23 | 0.0344 |
| B24 | 0.075 |
| B26 | 0.0211 |
| B27 | 0.375 |
| B28 | 0.0963 |
| B32 | 1-5 |
| B33 | 0.0542 |
| B34 | 0.1513 |
| B35 | 0.1591 |
| B36 | 0.1507 |
| B38 | 0.1185 |
| B39 | 0.0622 |
| B40 | 0.0723 |
| B43 | 1-5 |
| B44 | 0.1901 |
| B45 | 0.318 |
| B46 | 0.3142 |
| B47 | 0.3002 |
| B48 | 0.1485 |
| B49 | 0.2486 |
| B50 | 0.0507 |
| B51 | 0.0991 |
| B52 | 0.6351 |
| B54 | 0.0740 |
| B55 | 0.0938 |
| B57 | 0.1045 |
| B58 | 0.0672 |
| B59 | 0.1465 |
| B60 | 0.0059 |
| B61 | 0.2696 |
| B62 | >5 |
| B63 | 0.4732 |
| B64 | 0.2504 |
| B65 | 0.2784 |
| B66 | 0.4656 |
| B67 | 0.0778 |
| B68 | 0.2345 |
| B69 | 0.1-0.5 |
| B70 | ≈1 |
| B71 | 0.9567 |
| B72 | 0.05-0.1 |
| B73 | ≈1 |
| B74 | 0.1629 |
| B75 | ≈1 |
| B76 | 0.0256 |
| B77 | 0.0392 |
| B78 | 0.1-0.5 |
| B79 | 0.3458 |
| B80 | 0.7957 |
| B81 | 0.2082 |
| B82 | 0.0186 |
| B83 | 0.2274 |
| B85 | 0.1306 |
| B86 | 0.2527 |
| B87 | 0.0886 |
| B88 | 0.1444 |
| B89 | >5 |
| B90 | 0.5037 |
| B91 | 0.8759 |
| B92 | 0.9099 |
| B93 | 0.1293 |
| B94 | 0.8524 |
| B95 | 0.7706 |
| B96 | 1-5 |
| B97 | 0.1-0.5 |
| B98 | 0.4183 |
| B99 | 0.5996 |
| B100 | 1-5 |
| B101 | 0.0397 |
| B102 | 0.1154 |
| B103 | 0.042 |
| B104 | 0.0691 |
| B105 | 0.1769 |
| B106 | 0.3153 |
| B108 | 0.0891 |
| B109 | ≈1 |
| B111 | 0.1687 |
| B112 | 1-5 |
| B113 | 0.1-0.5 |
| B114 | 1-5 |
| B115 | 0.3063 |
| B118 | 0.0641 |
| B119 | 0.1-0.5 |
| B120 | 0.6757 |
| B121 | 0.1-0.5 |
| B122 | >5 |
| B123 | 1-5 |
| B124 | ≈5 |
| B125 | 0.6796 |
| B126 | >5 |
| B127 | ≈1 |
| B128 | 1-5 |
| B129 | >5 |
| B130 | 1-5 |
| B131 | 1-5 |
| B132 | 0.5802 |
| B133 | 0.1-0.5 |
| B134 | 0.6705 |
| B135 | 0.6261 |
| B136 | 1-5 |
| B137 | 0.05-0.1 |
| B138 | 0.718 |

Example 14

In Vitro Cell Assay

The procedures for establishing tumor xenografts and the dosing of B26 were carried out and accordance with ITRI institutional animal care and use committee in an IACUC. Female BALB/c nude mice (6 to 8 weeks old) were purchased from BioLASCO Co., Ltd. (Taipei, Taiwan). Female BALB/c nude mice were implanted subcutaneously in the right flank with $1\times10^7$ MV4-11 (FLT3-ITD) cells per mice. Treatments were initiated when tumors were 150 to 200 mm$^3$ in size. Mice were randomly assigned into cohorts (typically 4 mice per group for efficacy studies). B26 (50 and 150 mg/kg, bid.) and vehicle were given via oral gavage for 14 days from the 16$^{th}$ day after inoculation. Tumor volumes were assessed everyday and body weights were assessed two times weekly. Caliper measurements of tumors were converted into mean tumor volume using the formula: 0.5×[length×(width)$^2$].

In the MV4-11 (FLT3-ITD) subcutaneous tumor xenograft model in BALB/c nude mice, oral administration of B26 at 50 or 150 mg/kg bid for 14 days showed a potent and significant antitumor effect in a dose-dependent manner. B26 dosing at 50 and 150 mg/kg (bid) showed tumor complete regression of all mouse on day 9 and day 7, respectively. Referring to FIG. 1, no significant suppression of body weight gain or mortality was observed in the B26 treated group during the experiments. Compound B26 of this invention is a novel and potent FLT3 inhibitor with promising anti-tumor and anti-leukemia activity.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A compound of formula I or a geometric isomer, enantiomer, diastereomer, racemate or a pharmaceutically acceptable salt thereof:

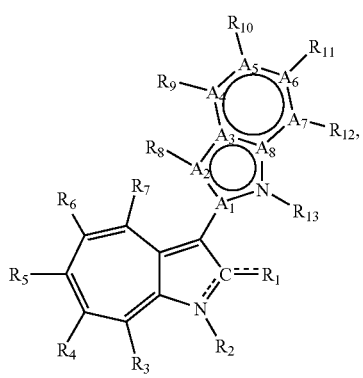

(I)

wherein
one of ===== is single bond and the other ===== is double bond;
each of $A_1$, $A_2$, $A_3$, $A_4$, $A_5$, $A_6$, $A_7$, and $A_8$, independently, is carbon or nitrogen;
$R_1$ is O, S, SR, $NH_2$, NRR', NH, or NR;
each of $R_2$, $R_3$, $R_4$, $R_5$, $R_6$, $R_7$, $R_8$, $R_9$, $R_{10}$, $R_{11}$, $R_{12}$, and $R_{13}$, independently, is null, H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, heterocycloalkyl heterocycle with 3-10 member ring structure containing 1-4 heteroatoms selected from the group consisting of nitrogen, oxygen and sulfur, heterocycloalkenyl with 3-10 member ring structure containing 1-4 heteroatoms selected from the group consisting of nitrogen, oxygen and sulfur and containing 1-3 isolated, conjugated or/and cumulated double bonds, aryl, heteroaryl with 5-15 member aromatic structure containing 1-4 heteroatoms selected from the group consisting of nitrogen, oxygen and sulfur, $NO_2$, NO, $N_3$, SCN, CN, OCN, OR, OC(O)R, OC(S)R, OC(S)OR, OC(O)SR, OC(S)SR, OC(O)NRR', OC(S)NRR", ONRR', OS(O)R, OS(O)$_2$R, SR, SC(O)R, SC(S)R, SC(S)OR, SC(O)SR, SC(S)SR, SC(O)NRR', SC(S)NRR', S(O)R, S(O)$_2$R, S(O)NRR', S(O)$_2$NRR', S(O)OR, S(O)$_2$OR, NCO, NCS, NRR', N(R)—C(O)R', N(R)—C(O)OR', N(R)—C(S)R', N(R)—C(S)OR', N(C(O)R)—C(O)R', N(R)—S(O)R', N(R)—S(O)OR', N(R)—S(O)$_2$R', N(R)—S(O)$_2$OR', N(R)—OR', N(OR)—C(O)R', N(OR)—C(O)OR', N(OR)—C(S)R', N(OR)—C(S)OR', N(OR)—C(S)SR', N(OR)—S(O)R', N(OR)—S(O)OR', N(OR)—S(O)$_2$R', N(OR)—S(O)$_2$OR', C(O)R, C(O)OR, C(O)NRR', C(O)SR, C(S)R, C(S)OR, C(S)NRR', C(S)SR, C(NR)—R', C(NR)—OR', C(NR)—NR'R", C(NR)—SR', C(NOR)—R', C(NOR)—OR', C(NOR)—NR'R", or C(NOR)—SR'; or $R_2$ and $R_3$, $R_3$ and $R_4$, $R_4$ and $R_5$, $R_5$ and $R_6$, $R_6$ and $R_7$, $R_8$ and $R_9$, $R_9$ and $R_{10}$, $R_{10}$ and $R_{11}$, $R_{11}$ and $R_{12}$, or $R_{12}$ and $R_{13}$ together with the atoms to which they are attached, are $C_3$-$C_{20}$ cycloalkyl, $C_3$-$C_{20}$ cycloalkenyl, heterocycle with 3-10 member ring structure containing 1-4 heteroatoms selected from the group consisting of nitrogen, oxygen and sulfur, heterocycloalkenyl with 3-10 member ring structure containing 1-4 heteroatoms selected from the group consisting of nitrogen, oxygen and sulfur and containing 1-3 isolated, conjugated or/and cumulated double bonds, aryl, or heteroaryl with 5-15 member aromatic structure containing 1-4 heteroatoms selected from the group consisting of nitrogen, oxygen and sulfur;

wherein each of R, R', and R", independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, heterocycle with 3-10 member ring structure containing 1-4 heteroatoms selected from the group consisting of nitrogen, oxygen and sulfur, heterocycloalkenyl with 3-10 member ring structure containing 1-4 heteroatoms selected from the group consisting of nitrogen, oxygen and sulfur and containing 1-3 isolated, conjugated or/and cumulated double bonds, aryl, or heteroaryl with 5-15 member aromatic structure containing 1-4 heteroatoms selected from the group consisting of nitrogen, oxygen and sulfur; or R and R', R and R" or R' and R" together with atoms to which they are attached, are heterocycle with 3-10 member ring structure containing 1-4 heteroatoms selected from the group consisting of nitrogen, oxygen and sulfur or heterocycloalkenyl with 3-10 member ring structure containing 1-4 heteroatoms selected from the group consisting of nitrogen, oxygen and sulfur and containing 1-3 isolated, conjugated or/and cumulated double bonds, and when each of $A_1$, $A_3$, $A_4$, $A_5$, $A_6$, $A_7$, and $A_8$ is carbon, $A_2$ is nitrogen, C===== N is C—N, and C===== $R_1$ is C=O, at least one $R_2$, $R_3$, $R_4$, $R_5$, $R_6$, $R_7$, $R_8$, $R_9$, $R_{10}$, $R_{11}$, and $R_{12}$ is not H, or when each of $A_1$, $A_3$, $A_4$, $A_5$, $A_6$, $A_7$, and $A_8$ is carbon, $A_2$ is nitrogen, C===== N is C=N, and C===== $R_1$ is C—$NH_2$, $R_2$ is null, at least one $R_3$, $R_4$, $R_5$, $R_6$, $R_7$, $R_8$, $R_9$, $R_{10}$, $R_{11}$, and $R_{12}$ is not H.

2. The compound as claimed in claim 1, wherein $A_2$ is nitrogen.

3. The compound as claimed in claim 1, wherein $A_1$, $A_3$, $A_4$, $A_5$, $A_6$, $A_7$, and $A_8$ are carbon.

4. The compound as claimed in claim 1, wherein C===== N is C—N.

5. The compound as claimed in claim 1, wherein C===== $R_1$ is C=$R_1$.

6. The compound as claimed in claim 5, wherein C=$R_1$ is C=O.

7. A compound selected from the compounds delineated in Table A or a geometric isomer, enantiomer, diastereomer, racemate or a pharmaceutically salt thereof:

TABLE A
| Compound No. | Structure |
|---|---|
| B1 | 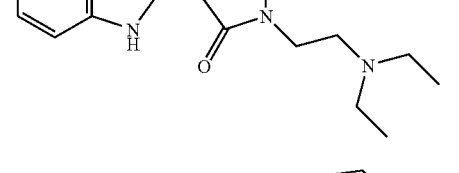 |
| B2 | 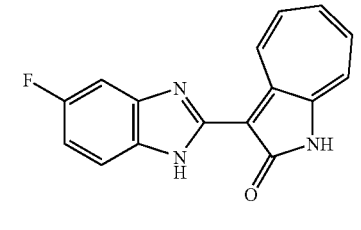 [SMILES: O=c1[nH]c2cccccc-2c1-c1nc2cc(F)ccc2[nH]1] |
| B3 | 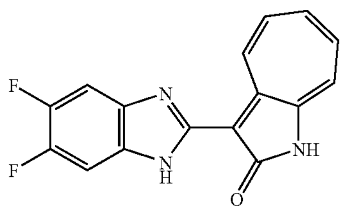 [SMILES: O=c1[nH]c2cccccc-2c1-c1nc2cc(F)c(F)cc2[nH]1] |
| B4 | 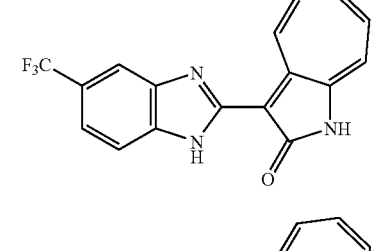 |
| B5 | 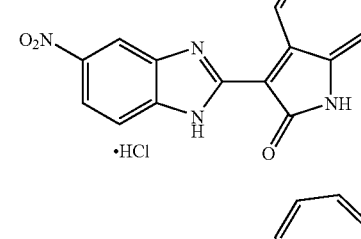 |
| B6 | 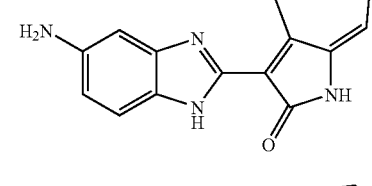 |
| B7 | 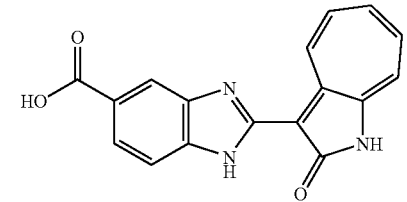 [SMILES: O=C(O)c1ccc2[nH]c(-c3c4cccccc-4[nH]c3=O)nc2c1] |

TABLE A-continued
| Compound No. | Structure |
| --- | --- |
| B8 | 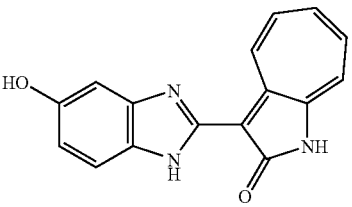 [SMILES: O=c1[nH]c2cccccc-2c1-c1nc2cc(O)ccc2[nH]1] |
| B9 | 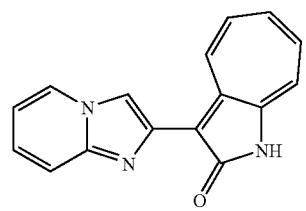 [SMILES: O=c1[nH]c2cccccc-2c1-c1cn2ccccc2n1] |
| B10 | 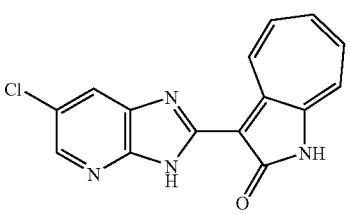 [SMILES: O=c1[nH]c2cccccc-2c1-c1nc2cc(Cl)cnc2[nH]1] |
| B11 | 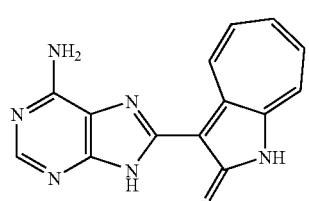 |
| B12 | 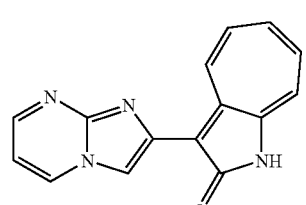 |
| B13 | 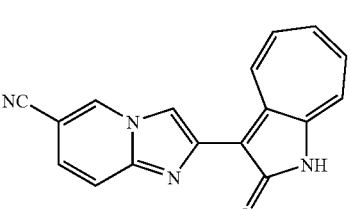 |
| B14 | 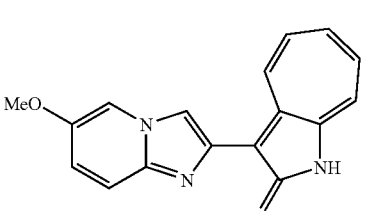 |

TABLE A-continued
| Compound No. | Structure |
|---|---|
| B15 | 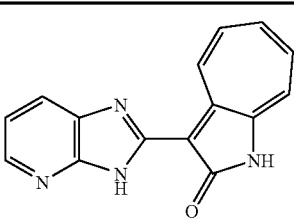 |
| B16 | 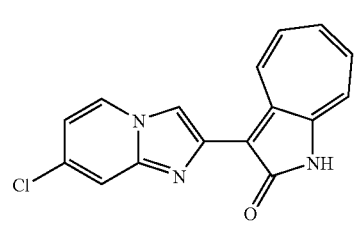 [SMILES: O=c1[nH]c2cccccc-2c1-c1cn2ccc(Cl)cc2n1] |
| B17 | 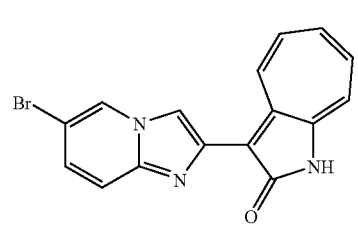 [SMILES: O=c1[nH]c2cccccc-2c1-c1cn2cc(Br)ccc2n1] |
| B18 | 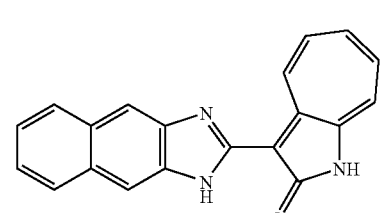 |
| B19 | 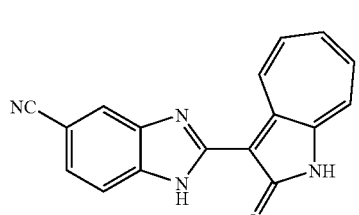 |
| B20 | 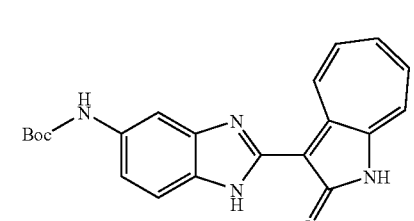 |
| B21 | 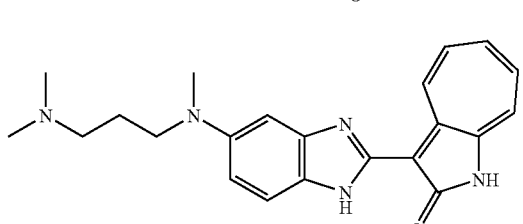 |

TABLE A-continued

| Compound No. | Structure |
| --- | --- |
| B22 | 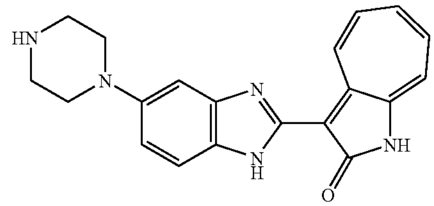 [SMILES: O=c1[nH]c2cccccc-2c1-c1nc2cc(N3CCNCC3)ccc2[nH]1] |
| B23 | 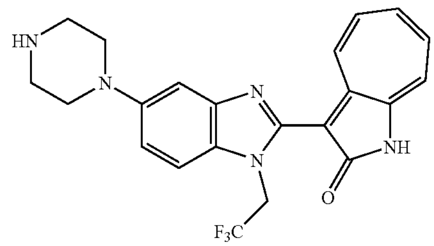 [SMILES: O=c1[nH]c2cccccc-2c1-c1nc2cc(N3CCNCC3)ccc2n1CC(F)(F)F] |
| B24 | 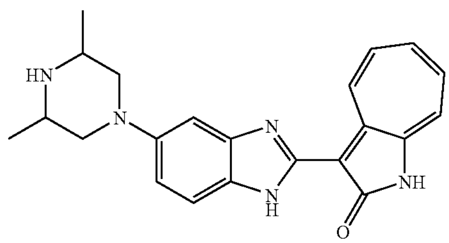 [SMILES: CC1CN(c2ccc3[nH]c(-c4c5cccccc-5[nH]c4=O)nc3c2)CC(C)N1] |
| B25 | 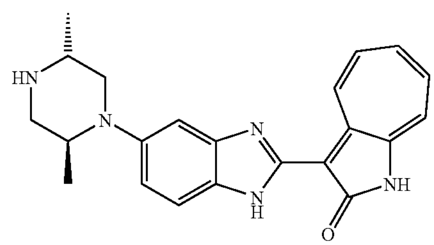 |
| B26 | 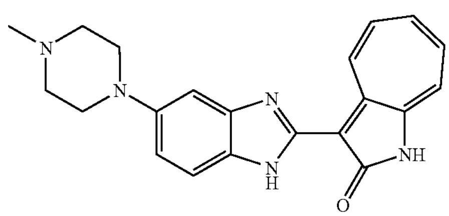 [SMILES: CN1CCN(c2ccc3[nH]c(-c4c5cccccc-5[nH]c4=O)nc3c2)CC1] |
| B27 | 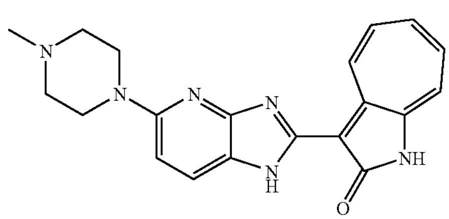 [SMILES: CN1CCN(c2ccc3[nH]c(-c4c5cccccc-5[nH]c4=O)nc3n2)CC1] |
| B28 | 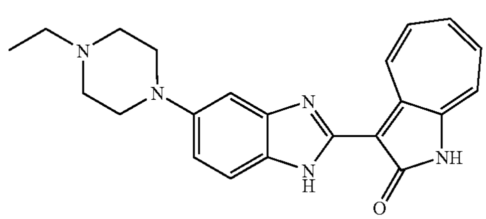 |

TABLE A-continued

| Compound No. | Structure |
| --- | --- |
| B29 | 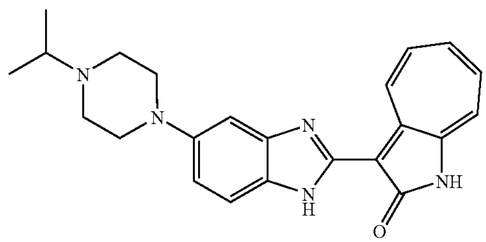 [SMILES: CC(C)N1CCN(c2ccc3[nH]c(-c4c5cccccc-5[nH]c4=O)nc3c2)CC1] |
| B30 | 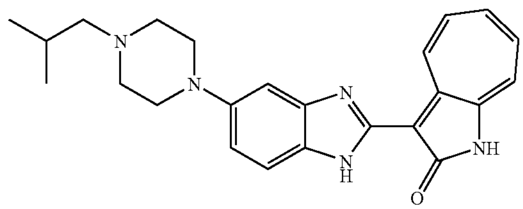 [SMILES: CC(C)CN1CCN(c2ccc3[nH]c(-c4c5cccccc-5[nH]c4=O)nc3c2)CC1] |
| B31 | 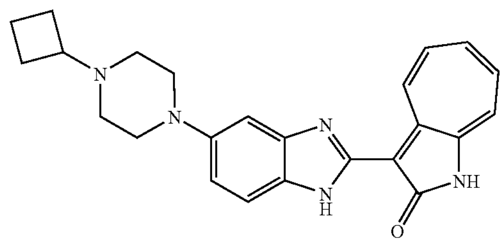 [SMILES: O=c1[nH]c2cccccc-2c1-c1nc2cc(N3CCN(C4CCC4)CC3)ccc2[nH]1] |
| B32 | 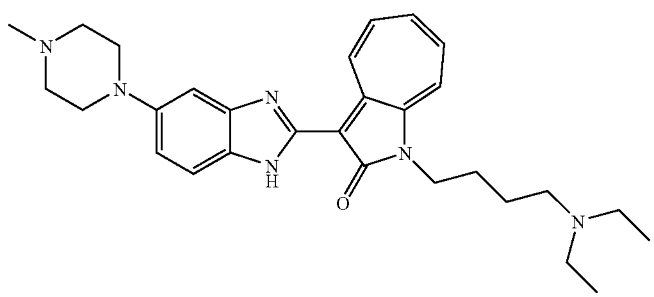 [SMILES: CCN(CC)CCCCn1c2cccccc-2c(-c2nc3cc(N4CCN(C)CC4)ccc3[nH]2)c1=O] |
| B33 | 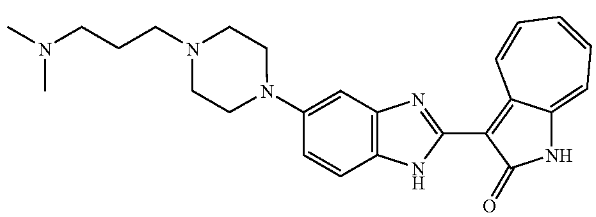 [SMILES: CN(C)CCCN1CCN(c2ccc3[nH]c(-c4c5cccccc-5[nH]c4=O)nc3c2)CC1] |
| B34 | 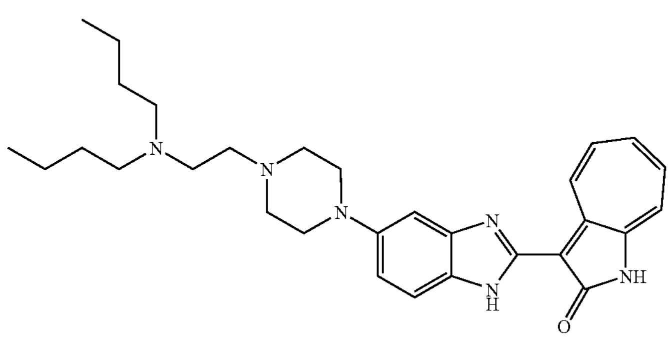 [SMILES: CCCCN(CCCC)CCN1CCN(c2ccc3[nH]c(-c4c5cccccc-5[nH]c4=O)nc3c2)CC1] |

TABLE A-continued

| Compound No. | Structure |
|---|---|
| B35 | 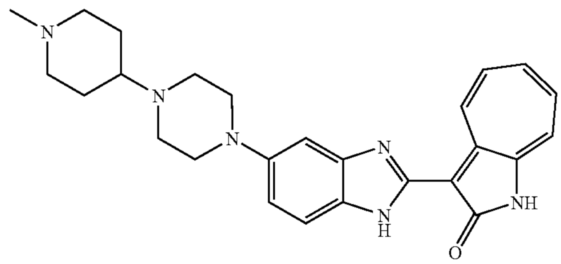 [SMILES: CN1CCC(N2CCN(c3ccc4[nH]c(-c5c6cccccc-6[nH]c5=O)nc4c3)CC2)CC1] |
| B36 | 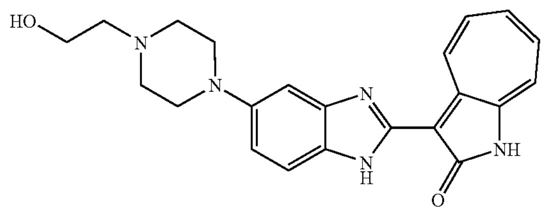 [SMILES: O=c1[nH]c2cccccc-2c1-c1nc2cc(N3CCN(CCO)CC3)ccc2[nH]1] |
| B37 | 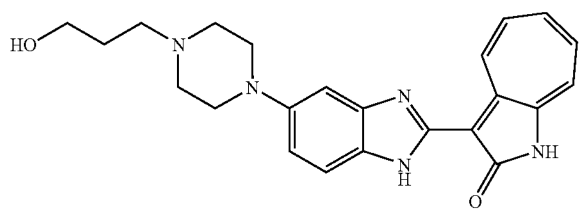 [SMILES: O=c1[nH]c2cccccc-2c1-c1nc2cc(N3CCN(CCCO)CC3)ccc2[nH]1] |
| B38 | 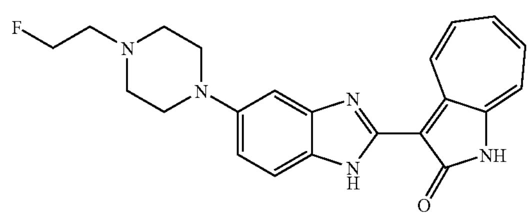 [SMILES: O=c1[nH]c2cccccc-2c1-c1nc2cc(N3CCN(CCF)CC3)ccc2[nH]1] |
| B39 | 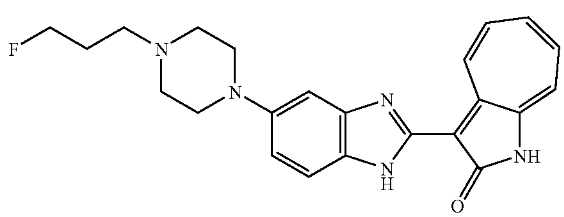 [SMILES: O=c1[nH]c2cccccc-2c1-c1nc2cc(N3CCN(CCCF)CC3)ccc2[nH]1] |
| B40 | 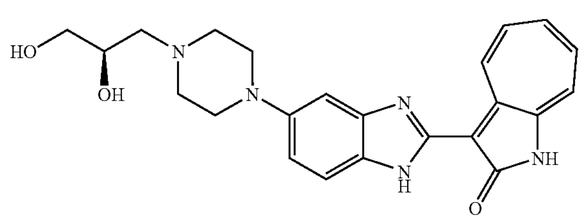 [SMILES: O=c1[nH]c2cccccc-2c1-c1nc2cc(N3CCN(C[C@@H](O)CO)CC3)ccc2[nH]1] |

TABLE A-continued
| Compound No. | Structure |
|---|---|
| B41 | 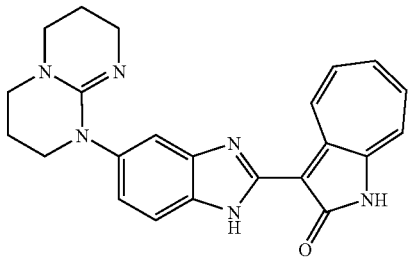 [SMILES: O=c1[nH]c2cccccc-2c1-c1nc2cc(N3CCCN4CCCN=C43)ccc2[nH]1] |
| B42 | 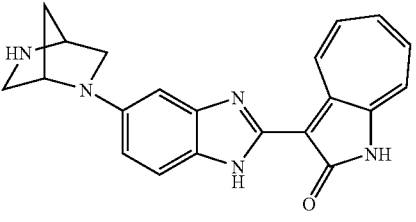 [SMILES: O=c1[nH]c2cccccc-2c1-c1nc2cc(N3CC4CC3CN4)ccc2[nH]1] |
| B43 | 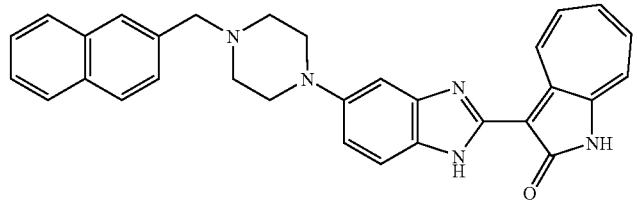 [SMILES: O=c1[nH]c2cccccc-2c1-c1nc2cc(N3CCN(Cc4ccc5ccccc5c4)CC3)ccc2[nH]1] |
| B44 | 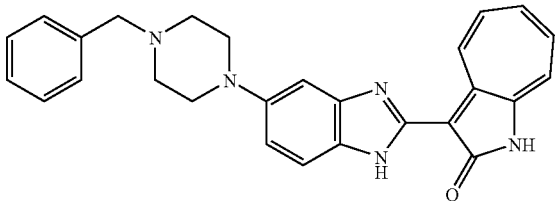 [SMILES: O=c1[nH]c2cccccc-2c1-c1nc2cc(N3CCN(Cc4ccccc4)CC3)ccc2[nH]1] |
| B45 | 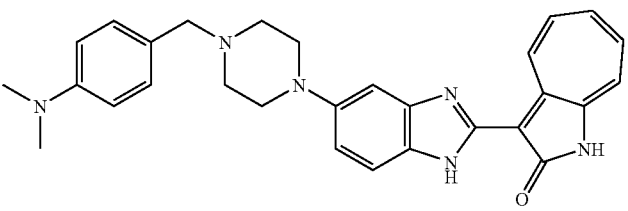 [SMILES: CN(C)c1ccc(CN2CCN(c3ccc4[nH]c(-c5c6cccccc-6[nH]c5=O)nc4c3)CC2)cc1] |
| B46 | 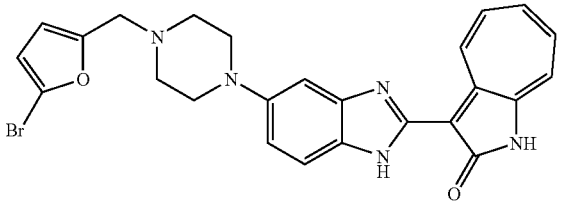 [SMILES: O=c1[nH]c2cccccc-2c1-c1nc2cc(N3CCN(Cc4ccc(Br)o4)CC3)ccc2[nH]1] |
| B47 | 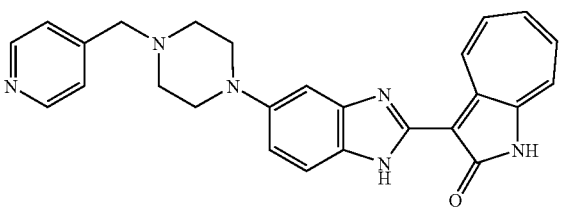 [SMILES: O=c1[nH]c2cccccc-2c1-c1nc2cc(N3CCN(Cc4ccncc4)CC3)ccc2[nH]1] |

TABLE A-continued

| Compound No. | Structure |
| --- | --- |
| B48 | 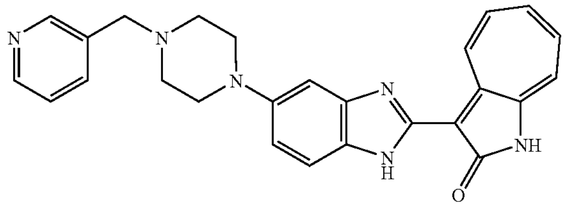 [SMILES: O=c1[nH]c2cccccc-2c1-c1nc2cc(N3CCN(Cc4cccnc4)CC3)ccc2[nH]1] |
| B49 | 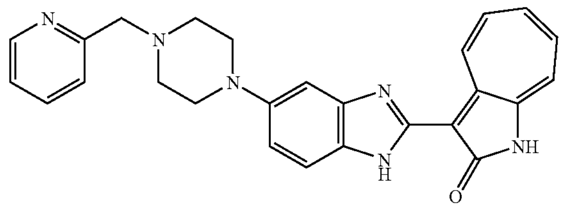 [SMILES: O=c1[nH]c2cccccc-2c1-c1nc2cc(N3CCN(Cc4ccccn4)CC3)ccc2[nH]1] |
| B50 | 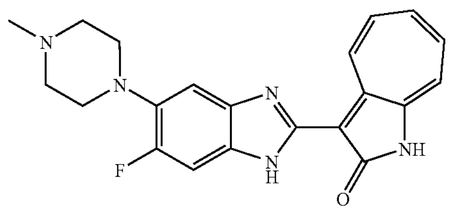 |
| B51 | 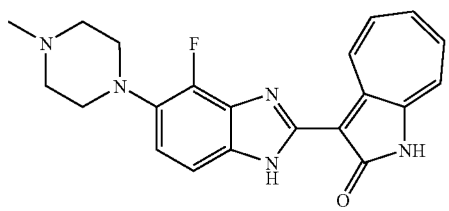 [SMILES: CN1CCN(c2ccc3[nH]c(-c4c5cccccc-5[nH]c4=O)nc3c2F)CC1] |
| B52 | 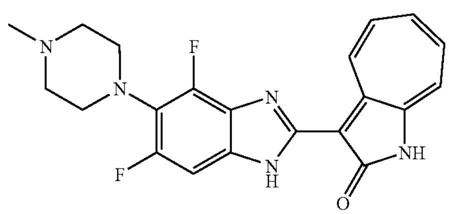 [SMILES: CN1CCN(c2c(F)cc3[nH]c(-c4c5cccccc-5[nH]c4=O)nc3c2F)CC1] |
| B53 | 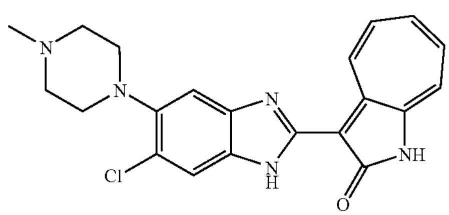 [SMILES: CN1CCN(c2cc3nc(-c4c5cccccc-5[nH]c4=O)[nH]c3cc2Cl)CC1] |
| B54 | 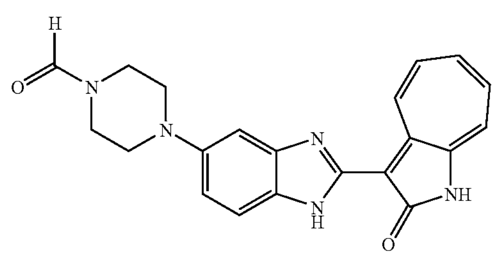 [SMILES: O=CN1CCN(c2ccc3[nH]c(-c4c5cccccc-5[nH]c4=O)nc3c2)CC1] |

TABLE A-continued

| Compound No. | Structure |
|---|---|
| B55 | 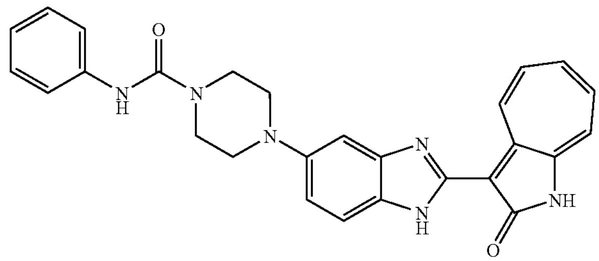 [SMILES: O=C(Nc1ccccc1)N1CCN(c2ccc3[nH]c(-c4c5cccccc-5[nH]c4=O)nc3c2)CC1] |
| B56 | 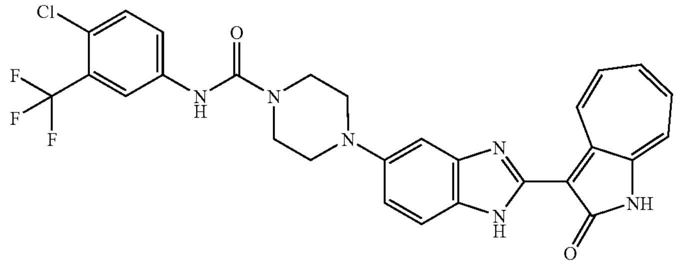 [SMILES: O=C(Nc1ccc(Cl)c(C(F)(F)F)c1)N1CCN(c2ccc3[nH]c(-c4c5cccccc-5[nH]c4=O)nc3c2)CC1] |
| B57 | 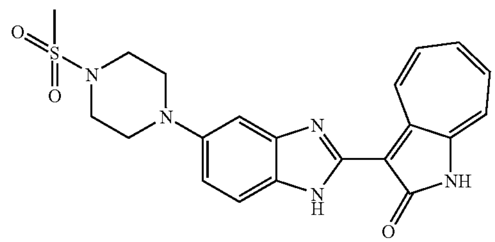 [SMILES: CS(=O)(=O)N1CCN(c2ccc3[nH]c(-c4c5cccccc-5[nH]c4=O)nc3c2)CC1] |
| B58 | 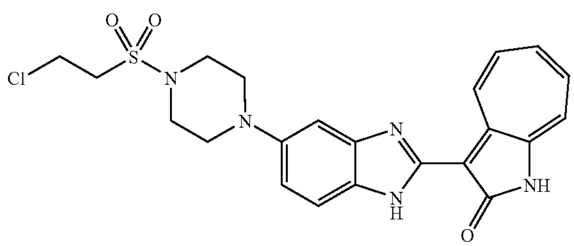 [SMILES: O=c1[nH]c2cccccc-2c1-c1nc2cc(N3CCN(S(=O)(=O)CCCl)CC3)ccc2[nH]1] |
| B59 | 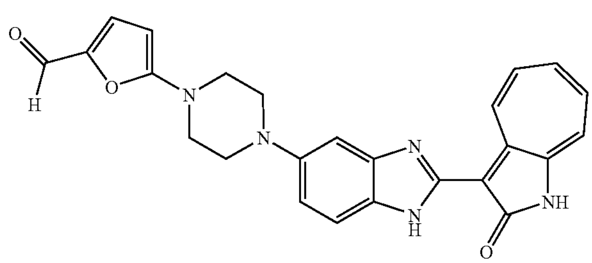 [SMILES: O=Cc1ccc(N2CCN(c3ccc4[nH]c(-c5c6cccccc-6[nH]c5=O)nc4c3)CC2)o1] |
| B60 | 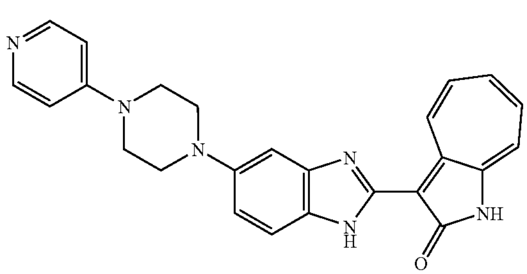 |

TABLE A-continued

| Compound No. | Structure |
|---|---|
| B61 | 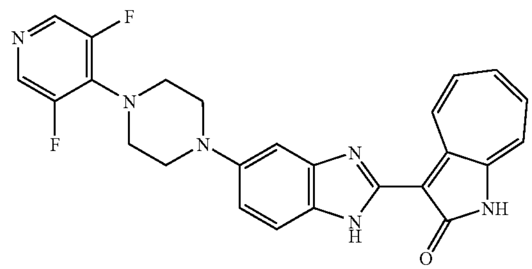 [SMILES: O=c1[nH]c2cccccc-2c1-c1nc2cc(N3CCN(c4c(F)cncc4F)CC3)ccc2[nH]1] |
| B62 | 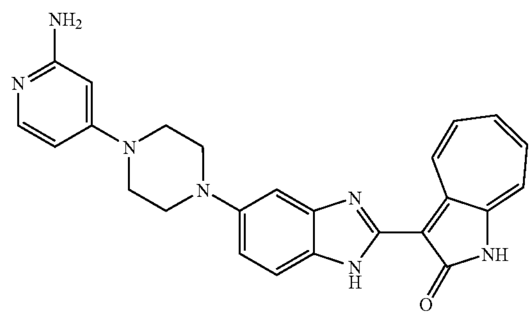 [SMILES: Nc1cc(N2CCN(c3ccc4[nH]c(-c5c6cccccc-6[nH]c5=O)nc4c3)CC2)ccn1] |
| B63 | 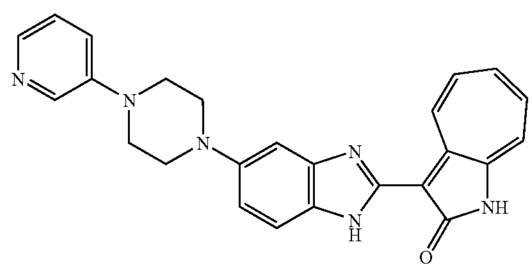 [SMILES: O=c1[nH]c2cccccc-2c1-c1nc2cc(N3CCN(c4cccnc4)CC3)ccc2[nH]1] |
| B64 | 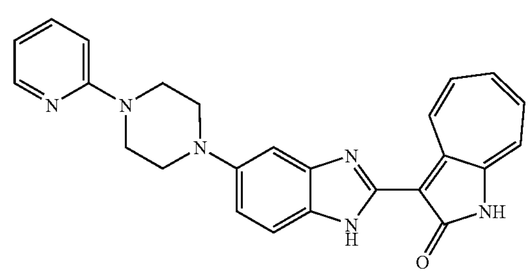 [SMILES: O=c1[nH]c2cccccc-2c1-c1nc2cc(N3CCN(c4ccccn4)CC3)ccc2[nH]1] |
| B65 | 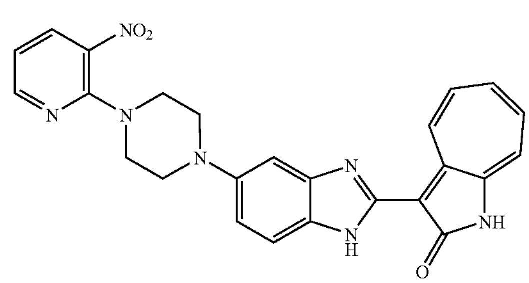 [SMILES: O=c1[nH]c2cccccc-2c1-c1nc2cc(N3CCN(c4ncccc4[N+](=O)[O-])CC3)ccc2[nH]1] |

TABLE A-continued

| Compound No. | Structure |
| --- | --- |
| B66 | 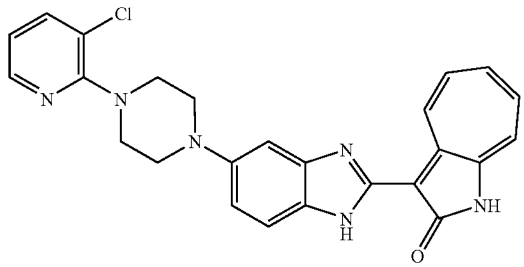 [SMILES: O=c1[nH]c2cccccc-2c1-c1nc2cc(N3CCN(c4ncccc4Cl)CC3)ccc2[nH]1] |
| B67 | 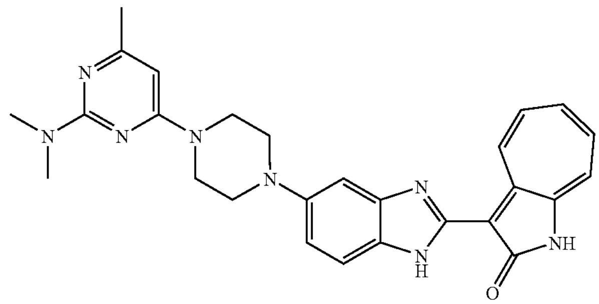 [SMILES: Cc1cc(N2CCN(c3ccc4[nH]c(-c5c6cccccc-6[nH]c5=O)nc4c3)CC2)nc(N(C)C)n1] |
| B68 | 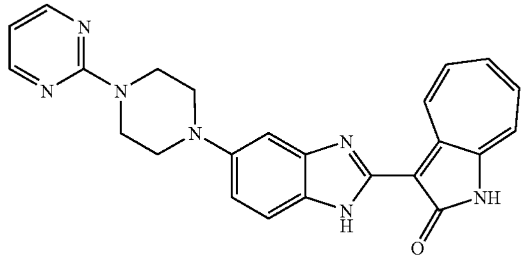 |
| B69 | 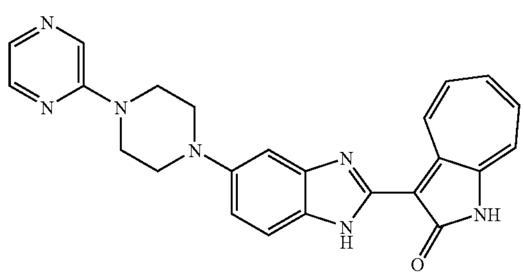 [SMILES: O=c1[nH]c2cccccc-2c1-c1nc2cc(N3CCN(c4cnccn4)CC3)ccc2[nH]1] |
| B70 | 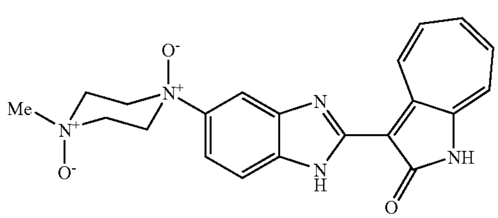 [SMILES: C[N+]1([O-])CC[N+]([O-])(c2ccc3[nH]c(-c4c5cccccc-5[nH]c4=O)nc3c2)CC1] |
| B71 | 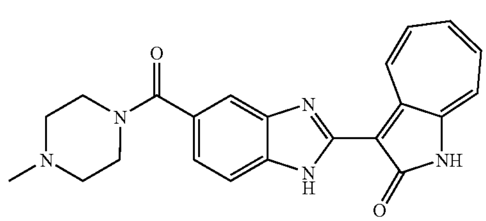 [SMILES: CN1CCN(C(=O)c2ccc3[nH]c(-c4c5cccccc-5[nH]c4=O)nc3c2)CC1] |

TABLE A-continued
| Compound No. | Structure |
|---|---|
| B72 | 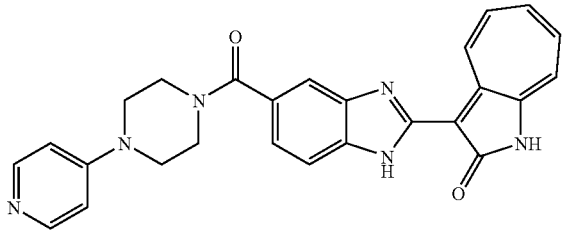 [SMILES: O=C(c1ccc2[nH]c(-c3c4cccccc-4[nH]c3=O)nc2c1)N1CCN(c2ccncc2)CC1] |
| B73 | 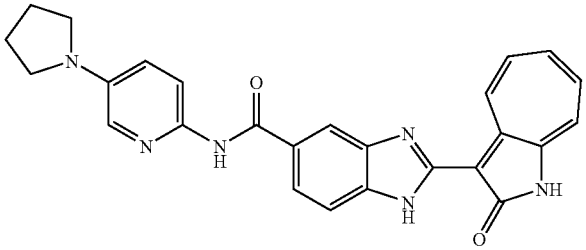 [SMILES: O=C(Nc1ccc(N2CCCC2)cn1)c1ccc2[nH]c(-c3c4cccccc-4[nH]c3=O)nc2c1] |
| B74 | 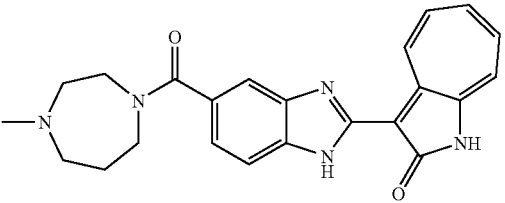 [SMILES: CN1CCCN(C(=O)c2ccc3[nH]c(-c4c5cccccc-5[nH]c4=O)nc3c2)CC1] |
| B75 | 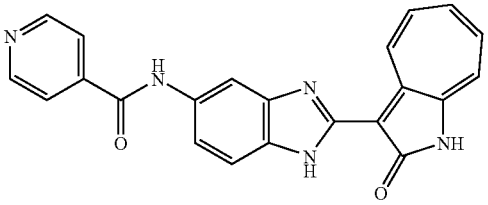 [SMILES: O=C(Nc1ccc2[nH]c(-c3c4cccccc-4[nH]c3=O)nc2c1)c1ccncc1] |
| B76 | 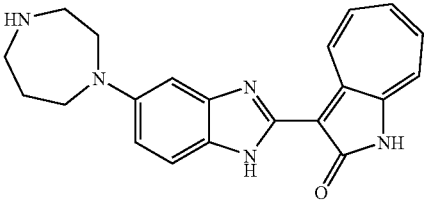 [SMILES: O=c1[nH]c2cccccc-2c1-c1nc2cc(N3CCCNCC3)ccc2[nH]1] |
| B77 | 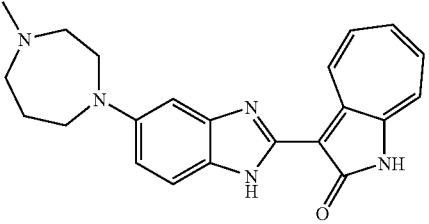 |

TABLE A-continued

| Compound No. | Structure |
| --- | --- |
| B78 | 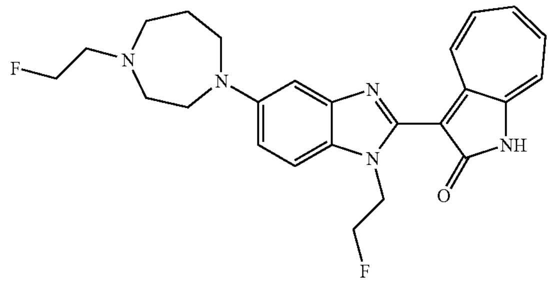 [SMILES: O=c1[nH]c2cccccc-2c1-c1nc2cc(N3CCCN(CCF)CC3)ccc2n1CCF] |
| B79 | 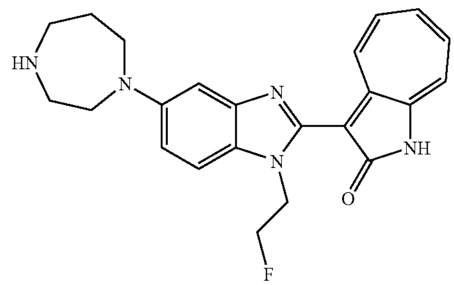 [SMILES: O=c1[nH]c2cccccc-2c1-c1nc2cc(N3CCCNCC3)ccc2n1CCF] |
| B80 | 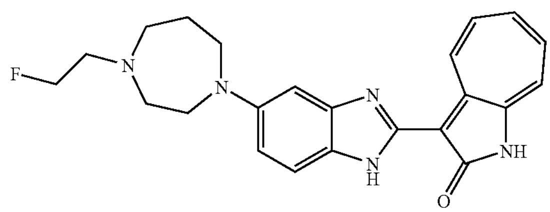 [SMILES: O=c1[nH]c2cccccc-2c1-c1nc2cc(N3CCCN(CCF)CC3)ccc2[nH]1] |
| B81 | 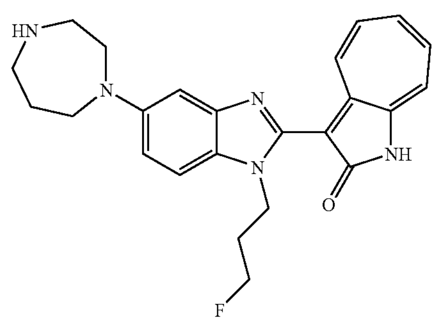 [SMILES: O=c1[nH]c2cccccc-2c1-c1nc2cc(N3CCCNCC3)ccc2n1CCCF] |
| B82 | 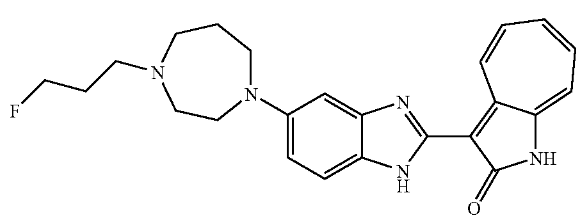 [SMILES: O=c1[nH]c2cccccc-2c1-c1nc2cc(N3CCCN(CCCF)CC3)ccc2[nH]1] |

TABLE A-continued
| Compound No. | Structure |
|---|---|
| B83 | 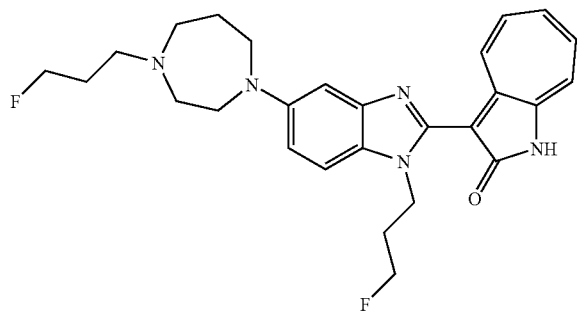 [SMILES: O=c1[nH]c2cccccc-2c1-c1nc2cc(N3CCCN(CCCF)CC3)ccc2n1CCCF] |
| B84 | 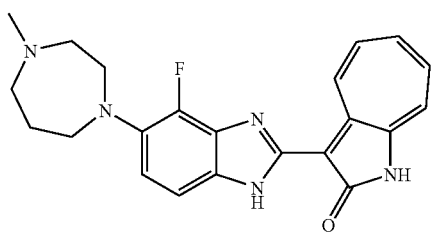 [SMILES: CN1CCCN(c2ccc3[nH]c(-c4c5cccccc-5[nH]c4=O)nc3c2F)CC1] |
| B85 | 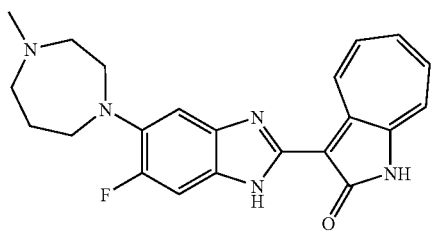 [SMILES: CN1CCCN(c2cc3nc(-c4c5cccccc-5[nH]c4=O)[nH]c3cc2F)CC1] |
| B86 | 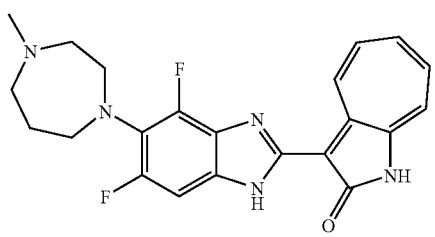 [SMILES: CN1CCCN(c2c(F)cc3[nH]c(-c4c5cccccc-5[nH]c4=O)nc3c2F)CC1] |
| B87 | 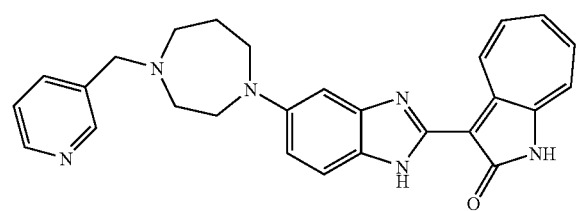 [SMILES: O=c1[nH]c2cccccc-2c1-c1nc2cc(N3CCCN(Cc4cccnc4)CC3)ccc2[nH]1] |
| B88 | 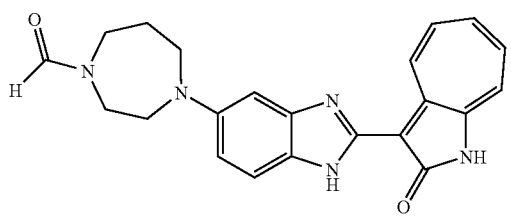 [SMILES: O=CN1CCCN(c2ccc3[nH]c(-c4c5cccccc-5[nH]c4=O)nc3c2)CC1] |

… TABLE A-continued
| Compound No. | Structure |
|---|---|
| B89 | 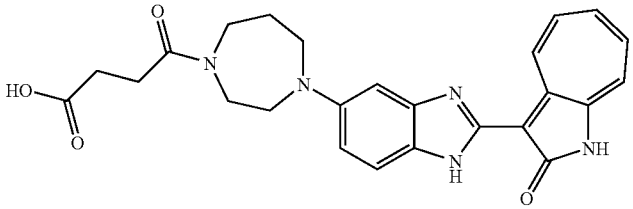 [SMILES: O=C(O)CCC(=O)N1CCCN(c2ccc3[nH]c(-c4c5cccccc-5[nH]c4=O)nc3c2)CC1] |
| B90 | 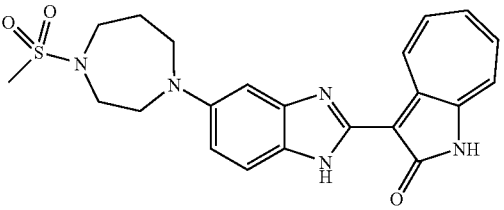 [SMILES: CS(=O)(=O)N1CCCN(c2ccc3[nH]c(-c4c5cccccc-5[nH]c4=O)nc3c2)CC1] |
| B91 | 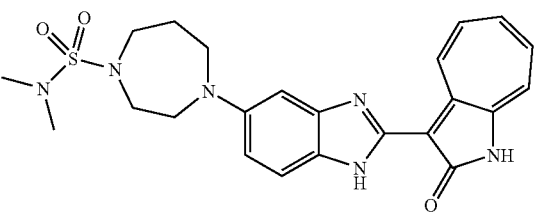 [SMILES: CN(C)S(=O)(=O)N1CCCN(c2ccc3[nH]c(-c4c5cccccc-5[nH]c4=O)nc3c2)CC1] |
| B92 | 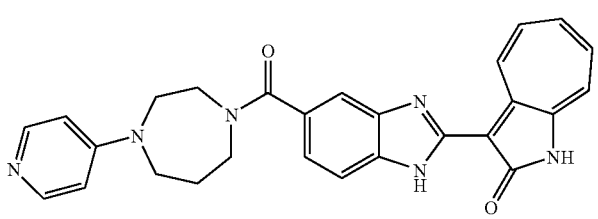 [SMILES: O=C(c1ccc2[nH]c(-c3c4cccccc-4[nH]c3=O)nc2c1)N1CCCN(c2ccncc2)CC1] |
| B93 | 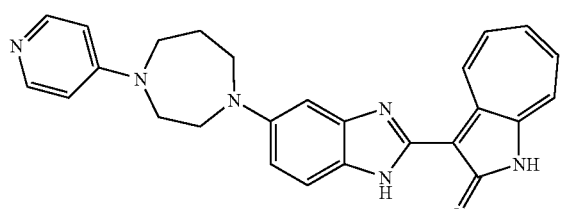 |
| B94 | 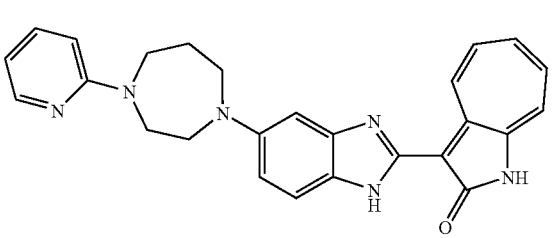 [SMILES: O=c1[nH]c2cccccc-2c1-c1nc2cc(N3CCCN(c4ccccn4)CC3)ccc2[nH]1] |
| B95 | 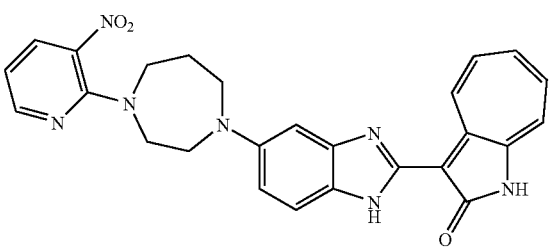 [SMILES: O=c1[nH]c2cccccc-2c1-c1nc2cc(N3CCCN(c4ncccc4[N+](=O)[O-])CC3)ccc2[nH]1] |

TABLE A-continued
| Compound No. | Structure |
| --- | --- |
| B96 | 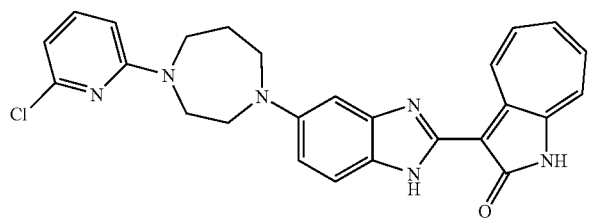 [SMILES: O=c1[nH]c2cccccc-2c1-c1nc2cc(N3CCCN(c4cccc(Cl)n4)CC3)ccc2[nH]1] |
| B97 | 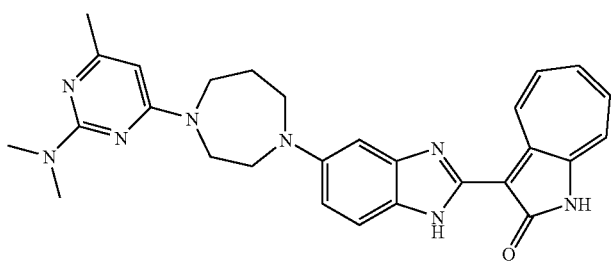 [SMILES: Cc1cc(N2CCCN(c3ccc4[nH]c(-c5c6cccccc-6[nH]c5=O)nc4c3)CC2)nc(N(C)C)n1] |
| B98 | 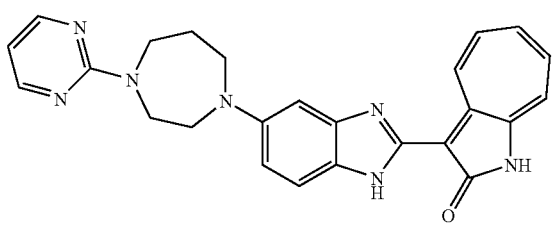 [SMILES: O=c1[nH]c2cccccc-2c1-c1nc2cc(N3CCCN(c4ncccn4)CC3)ccc2[nH]1] |
| B99 | 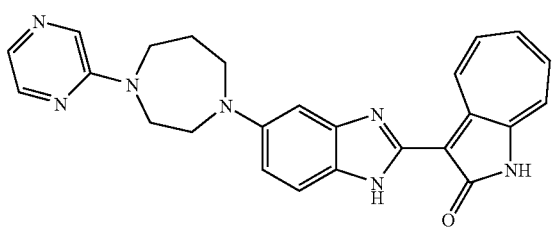 [SMILES: O=c1[nH]c2cccccc-2c1-c1nc2cc(N3CCCN(c4cnccn4)CC3)ccc2[nH]1] |
| B100 | 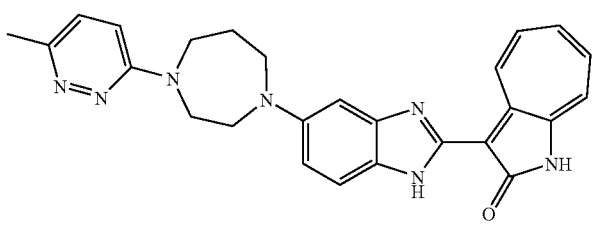 [SMILES: Cc1ccc(N2CCCN(c3ccc4[nH]c(-c5c6cccccc-6[nH]c5=O)nc4c3)CC2)nn1] |
| B101 | 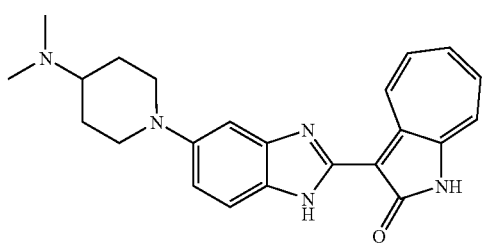 |

TABLE A-continued

| Compound No. | Structure |
| --- | --- |
| B102 | 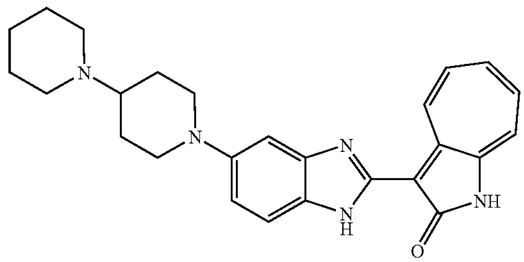 [SMILES: O=c1[nH]c2cccccc-2c1-c1nc2cc(N3CCC(N4CCCCC4)CC3)ccc2[nH]1] |
| B103 | 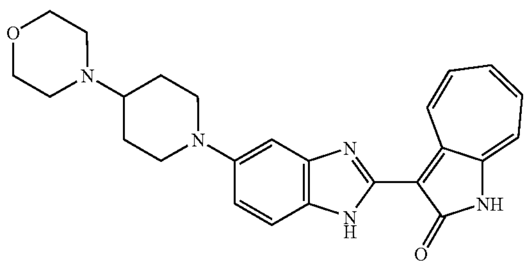 [SMILES: O=c1[nH]c2cccccc-2c1-c1nc2cc(N3CCC(N4CCOCC4)CC3)ccc2[nH]1] |
| B104 | 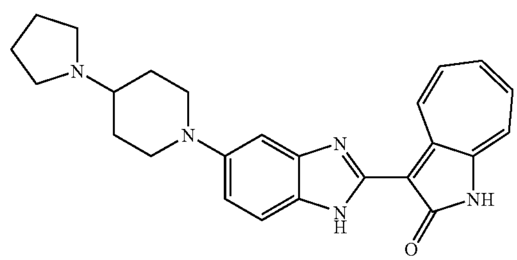 [SMILES: O=c1[nH]c2cccccc-2c1-c1nc2cc(N3CCC(N4CCCC4)CC3)ccc2[nH]1] |
| B105 | 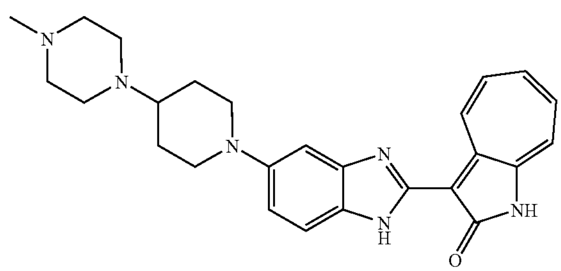 [SMILES: CN1CCN(C2CCN(c3ccc4[nH]c(-c5c6cccccc-6[nH]c5=O)nc4c3)CC2)CC1] |
| B106 | 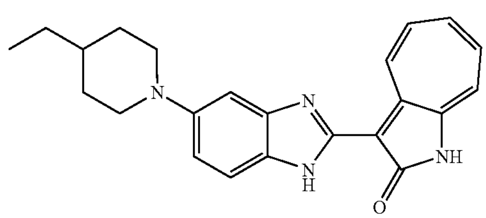 [SMILES: CCC1CCN(c2ccc3[nH]c(-c4c5cccccc-5[nH]c4=O)nc3c2)CC1] |
| B107 | 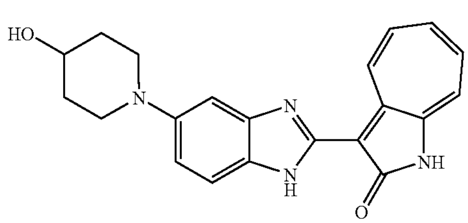 [SMILES: O=c1[nH]c2cccccc-2c1-c1nc2cc(N3CCC(O)CC3)ccc2[nH]1] |

TABLE A-continued

| Compound No. | Structure |
|---|---|
| B108 | 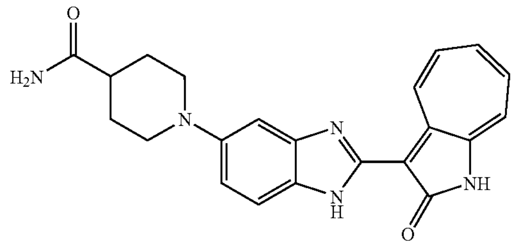 [SMILES: NC(=O)C1CCN(c2ccc3[nH]c(-c4c5cccccc-5[nH]c4=O)nc3c2)CC1] |
| B109 | 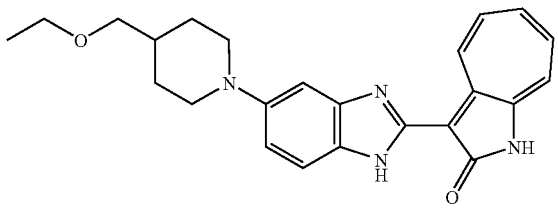 [SMILES: CCOCC1CCN(c2ccc3[nH]c(-c4c5cccccc-5[nH]c4=O)nc3c2)CC1] |
| B110 | 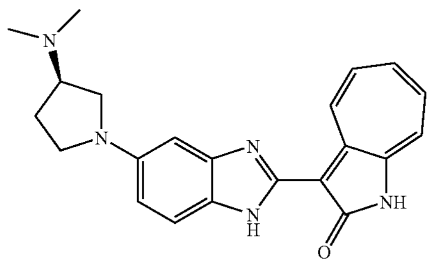 [SMILES: CN(C)[C@@H]1CCN(c2ccc3[nH]c(-c4c5cccccc-5[nH]c4=O)nc3c2)C1] |
| B111 | 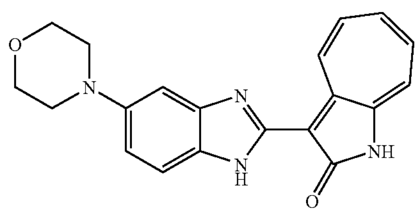 [SMILES: O=c1[nH]c2cccccc-2c1-c1nc2cc(N3CCOCC3)ccc2[nH]1] |
| B112 | 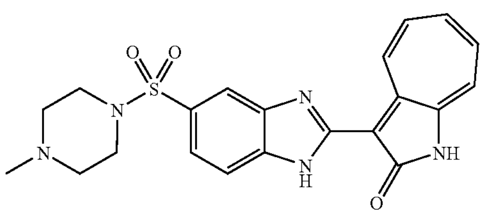 [SMILES: CN1CCN(S(=O)(=O)c2ccc3[nH]c(-c4c5cccccc-5[nH]c4=O)nc3c2)CC1] |
| B113 | 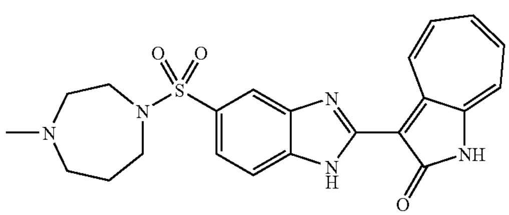 [SMILES: CN1CCCN(S(=O)(=O)c2ccc3[nH]c(-c4c5cccccc-5[nH]c4=O)nc3c2)CC1] |
| B114 | 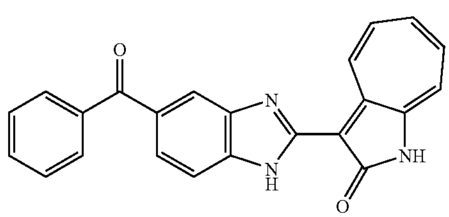 [SMILES: O=C(c1ccccc1)c1ccc2[nH]c(-c3c4cccccc-4[nH]c3=O)nc2c1] |

TABLE A-continued

| Compound No. | Structure |
| --- | --- |
| B115 | 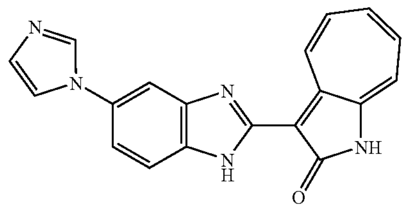 [SMILES: O=c1[nH]c2cccccc-2c1-c1nc2cc(-n3ccnc3)ccc2[nH]1] |
| B116 | 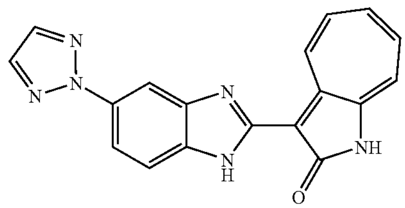 [SMILES: O=c1[nH]c2cccccc-2c1-c1nc2cc(-n3nccn3)ccc2[nH]1] |
| B117 | 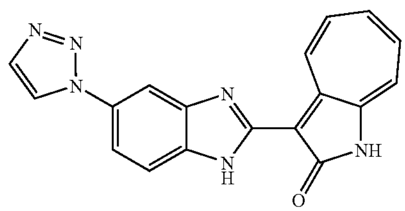 [SMILES: O=c1[nH]c2cccccc-2c1-c1nc2cc(-n3ccnn3)ccc2[nH]1] |
| B118 | 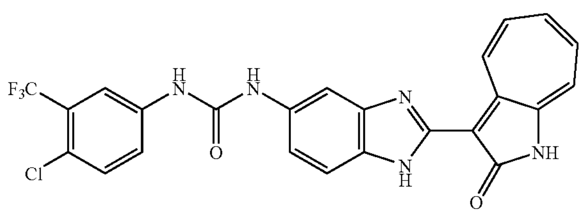 [SMILES: O=C(Nc1ccc(Cl)c(C(F)(F)F)c1)Nc1ccc2[nH]c(-c3c4cccccc-4[nH]c3=O)nc2c1] |
| B119 | 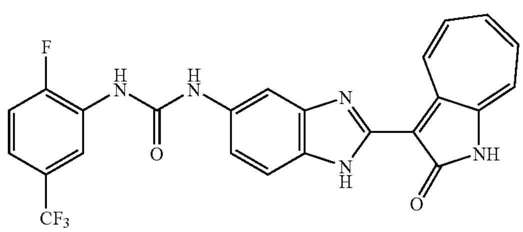 [SMILES: O=C(Nc1ccc2[nH]c(-c3c4cccccc-4[nH]c3=O)nc2c1)Nc1cc(C(F)(F)F)ccc1F] |
| B120 | 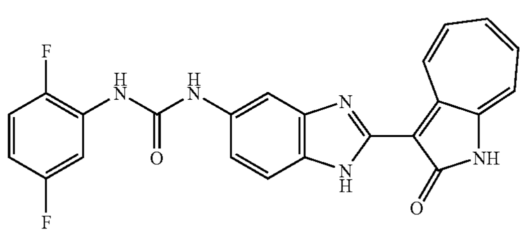 [SMILES: O=C(Nc1ccc2[nH]c(-c3c4cccccc-4[nH]c3=O)nc2c1)Nc1cc(F)ccc1F] |
| B121 | 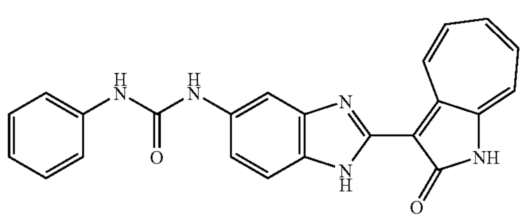 [SMILES: O=C(Nc1ccccc1)Nc1ccc2[nH]c(-c3c4cccccc-4[nH]c3=O)nc2c1] |

TABLE A-continued

| Compound No. | Structure |
| --- | --- |
| B122 | 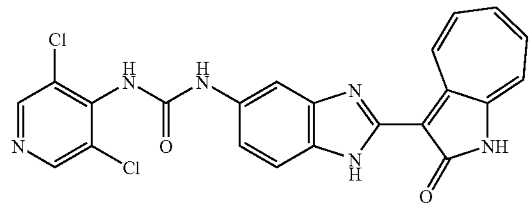 [SMILES: O=C(Nc1ccc2[nH]c(-c3c4cccccc-4[nH]c3=O)nc2c1)Nc1c(Cl)cncc1Cl] |
| B123 | 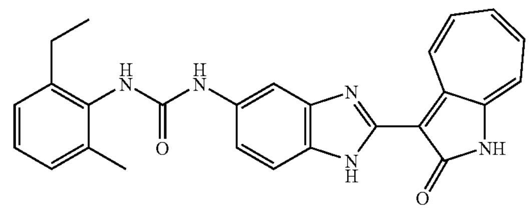 [SMILES: CCc1cccc(C)c1NC(=O)Nc1ccc2[nH]c(-c3c4cccccc-4[nH]c3=O)nc2c1] |
| B124 | 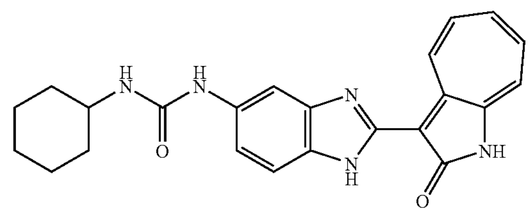 [SMILES: O=C(Nc1ccc2[nH]c(-c3c4cccccc-4[nH]c3=O)nc2c1)NC1CCCCC1] |
| B125 | 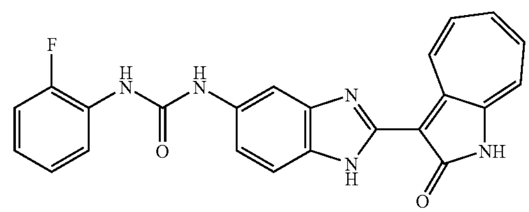 [SMILES: O=C(Nc1ccc2[nH]c(-c3c4cccccc-4[nH]c3=O)nc2c1)Nc1ccccc1F] |
| B126 | 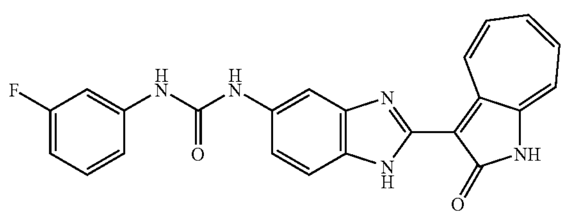 [SMILES: O=C(Nc1cccc(F)c1)Nc1ccc2[nH]c(-c3c4cccccc-4[nH]c3=O)nc2c1] |
| B127 | 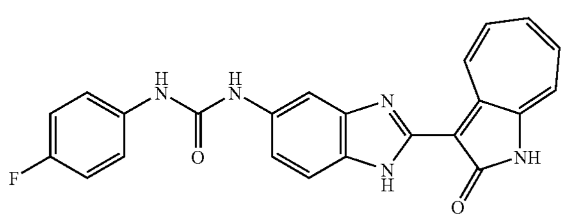 [SMILES: O=C(Nc1ccc(F)cc1)Nc1ccc2[nH]c(-c3c4cccccc-4[nH]c3=O)nc2c1] |
| B128 | 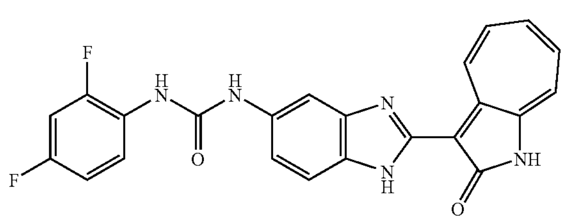 |

TABLE A-continued

| Compound No. | Structure |
|---|---|
| B129 | 1-(2,6-difluorophenyl)-3-(2-(2-oxo-2,3-dihydro-1H-indol-3-yl)-1H-benzo[d]imidazol-5-yl)urea |
| B130 | 1-(3-chloro-4-fluorophenyl)-3-(2-(2-oxo-2,3-dihydro-1H-indol-3-yl)-1H-benzo[d]imidazol-5-yl)urea |
| B131 | 1-(2-(2-oxo-2,3-dihydro-1H-indol-3-yl)-1H-benzo[d]imidazol-5-yl)-3-(2-(trifluoromethyl)phenyl)urea |
| B132 | 1-(2-(2-oxo-2,3-dihydro-1H-indol-3-yl)-1H-benzo[d]imidazol-5-yl)-3-(3-(trifluoromethyl)phenyl)urea |
| B133 | 1-(2-(2-oxo-2,3-dihydro-1H-indol-3-yl)-1H-benzo[d]imidazol-5-yl)-3-(4-(trifluoromethyl)phenyl)urea |
| B134 | 1-(3,5-bis(trifluoromethyl)phenyl)-3-(2-(2-oxo-2,3-dihydro-1H-indol-3-yl)-1H-benzo[d]imidazol-5-yl)urea |

TABLE A-continued

| Compound No. | Structure |
| --- | --- |
| B135 | 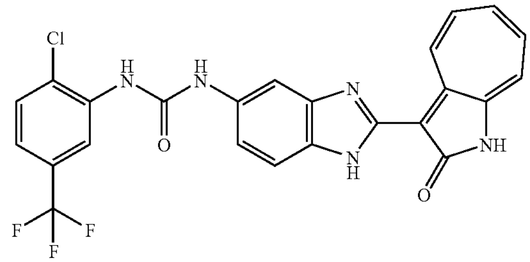 [SMILES: O=C(Nc1ccc2[nH]c(-c3c4cccccc-4[nH]c3=O)nc2c1)Nc1cc(C(F)(F)F)ccc1Cl] |
| B136 | 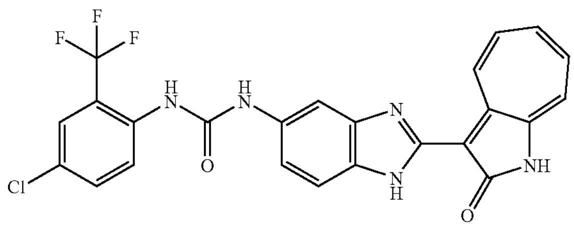 [SMILES: O=C(Nc1ccc2[nH]c(-c3c4cccccc-4[nH]c3=O)nc2c1)Nc1ccc(Cl)cc1C(F)(F)F] |
| B137 | 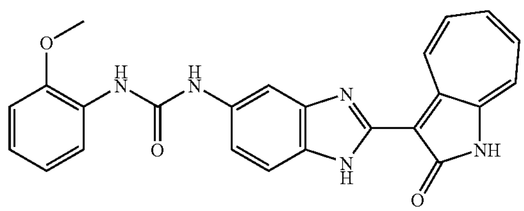 [SMILES: COc1ccccc1NC(=O)Nc1ccc2[nH]c(-c3c4cccccc-4[nH]c3=O)nc2c1] |
| B138 | 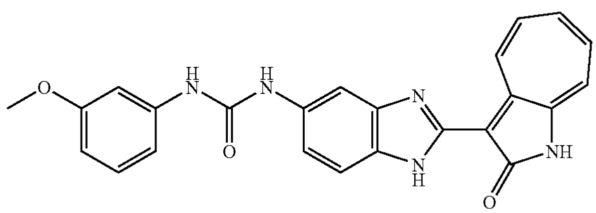 [SMILES: COc1cccc(NC(=O)Nc2ccc3[nH]c(-c4c5cccccc-5[nH]c4=O)nc3c2)c1] |
| B139 | 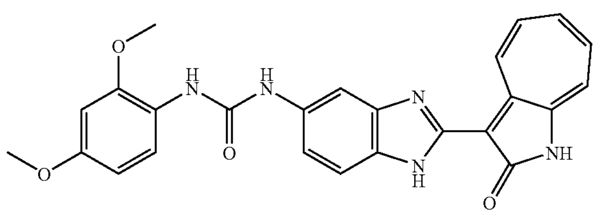 [SMILES: COc1ccc(NC(=O)Nc2ccc3[nH]c(-c4c5cccccc-5[nH]c4=O)nc3c2)c(OC)c1] |
| B140 | 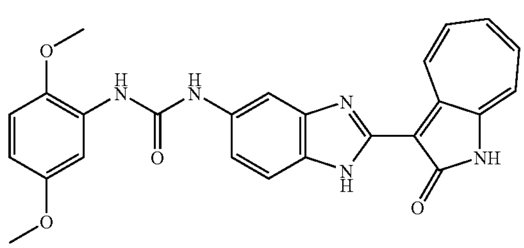 [SMILES: COc1ccc(OC)c(NC(=O)Nc2ccc3[nH]c(-c4c5cccccc-5[nH]c4=O)nc3c2)c1] |
| B141 | 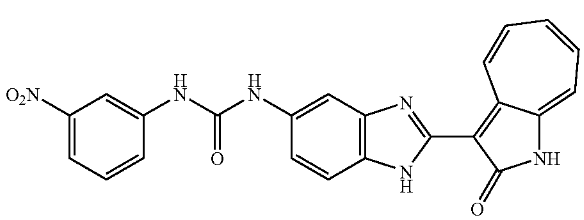 [SMILES: O=C(Nc1cccc([N+](=O)[O-])c1)Nc1ccc2[nH]c(-c3c4cccccc-4[nH]c3=O)nc2c1] |

TABLE A-continued

| Compound No. | Structure |
|---|---|
| B142 | 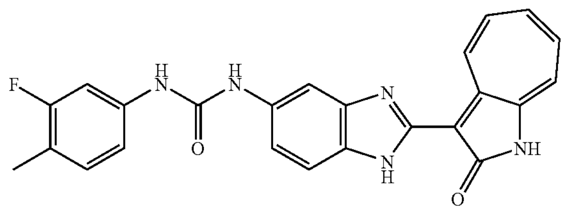 [SMILES: Cc1ccc(NC(=O)Nc2ccc3[nH]c(-c4c5cccccc-5[nH]c4=O)nc3c2)cc1F] |
| B143 | 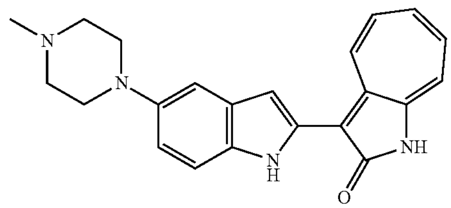 |

8. A pharmaceutical composition comprising a therapeutically effective amount of the compound of claim 1 and a pharmaceutical acceptable carrier.

9. A method of treating a subject in need of treatment for a cancer chosen from acute myeloid leukemia (AML), colon, breast, pancreas, and non-small-cell lung cancers, comprising administrating to the subject a therapeutically effective amount of the pharmaceutical composition of claim 8.

10. The method as claimed in claim 9, wherein the subject is a mammal.

11. The method as claimed in claim 9, wherein the subject is a human.

12. A pharmaceutical composition comprising a therapeutically effective amount of the compound of claim 7 and a pharmaceutical acceptable carrier.

13. A method of treating a subject in need of treatment for a cancer chosen from acute myeloid leukemia (AML), colon, breast, pancreas, and non-small-cell lung cancers, comprising administrating to the subject a therapeutically effective amount of the pharmaceutical composition of claim 12.

* * * * *